(12) United States Patent
Marchesi et al.

(10) Patent No.: US 12,397,045 B2
(45) Date of Patent: Aug. 26, 2025

(54) CLOSTRIDIOIDES DIFFICILE

(71) Applicant: IMPERIAL COLLEGE OF SCIENCE, TECHNOLOGY AND MEDICINE, London (GB)

(72) Inventors: Julian Marchesi, London (GB); Julie Mcdonald, London (GB); Benjamin Mullish, London (GB)

(73) Assignee: IMPERIAL COLLEGE OF SCIENCE, TECHNOLOGY AND MEDICINE, London (GB)

( * ) Notice: Subject to any disclaimer, the term of this patent is extended or adjusted under 35 U.S.C. 154(b) by 1020 days.

(21) Appl. No.: 17/046,700

(22) PCT Filed: Apr. 11, 2019

(86) PCT No.: PCT/GB2019/051052
§ 371 (c)(1),
(2) Date: Oct. 9, 2020

(87) PCT Pub. No.: WO2019/197836
PCT Pub. Date: Oct. 17, 2019

(65) Prior Publication Data
US 2021/0113671 A1  Apr. 22, 2021

(30) Foreign Application Priority Data
Apr. 13, 2018 (GB) .................................... 1806105

(51) Int. Cl.
| | | |
|---|---|---|
| *A61K 39/08* | (2006.01) | |
| *A61K 31/19* | (2006.01) | |
| *A61K 31/215* | (2006.01) | |
| *A61K 38/50* | (2006.01) | |
| *C12Q 1/34* | (2006.01) | |

(52) U.S. Cl.
CPC .............. *A61K 38/50* (2013.01); *A61K 31/19* (2013.01); *A61K 31/215* (2013.01); *C12Q 1/34* (2013.01); *C12Y 305/01024* (2013.01)

(58) Field of Classification Search
CPC ... A01N 37/02; A01P 1/00; A61P 1/00; A61P 31/04
USPC ....................................................... 424/184.1
See application file for complete search history.

(56) References Cited

FOREIGN PATENT DOCUMENTS

| WO | 2009087474 A2 | 7/2009 |
|---|---|---|
| WO | 2011002298 | 1/2011 |
| WO | 2016159853 A1 | 10/2016 |
| WO | 2017091783 A2 | 6/2017 |
| WO | 2017123592 A1 | 7/2017 |
| WO | 2018006088 A1 | 1/2018 |
| WO | 2018014833 A1 | 1/2018 |
| WO | 2019197836 A1 | 10/2019 |

OTHER PUBLICATIONS

International Search Report and Written Opinion for PCT/GB2019/051052 dated Sep. 13, 2019, 21 pages.
Shilling et al., Antimicrobial Effects of Virgin Coconut Oil and Its Medium-Chain Fatty Acids on Clostridium difficile, Journal of Medicinal Food, 2013, vol. 16(12), pp. 1079-1085.
GB Search Report for 1806105.1 dated Jan. 21, 2019, 6 pages.
Yoon et al., Bile salt hydrolase-mediated inhibitory effect of Bacteroides ovatus on growth of Clostridium difficile, 2017, vol. 55(11), pp. 892-899.

*Primary Examiner* — Tekchand Saidha
*Assistant Examiner* — Mohammad Y Meah
(74) *Attorney, Agent, or Firm* — Linda B. Huber; Nixon Peabody LLP

(57) ABSTRACT

The invention relates to *Clostridioides difficile*, and in particular to compounds, polypeptides and mixtures for the treatment of *C. difficile* infections. The invention also relates to nucleic acids, vectors comprising these nucleic acids and microorganisms for the treatment of *C. difficile* infections, and to methods of identifying and matching faecal microbiota transplant (FMT) donors to FMT recipients.

7 Claims, 62 Drawing Sheets
Specification includes a Sequence Listing.

Run 1 VA (saline-treated cultures)

Run 2 VA (saline-treated cultures)

Run 3 VA (saline-treated cultures)

Amended

Amended

B

C

Proposed pathway of 5-aminovalerate fermentation by C. viride (pathway 5).

CLOSTRIDIOIDES DIFFICILE

CROSS-REFERENCE TO RELATED APPLICATIONS

This application is a National Phase of International Application No. PCT/GB2019/051052, filed Apr. 11, 2019, which designated the U.S. and that International Application was published under PCT Article 21 (2) in English. This application also includes a claim of priority under 35 U.S.C. § 119 (a) and § 365 (b) to British patent application No. GB 1806105.1, filed Apr. 13, 2018, the contents of which are herein incorporated by reference in their entirety.

The present invention relates to *Clostridioides difficile*, and in particular to compounds, polypeptides and mixtures for the treatment of *C. difficile* infections. The invention also relates to nucleic acids, vectors comprising these nucleic acids and microorganisms for the treatment of *C. difficile* infections, and to methods of identifying and matching faecal microbiota transplant (FMT) donors to FMT recipients.

*Clostridioides difficile* (formerly *Clostridium difficile*) is an anaerobic, spore-forming, Gram-positive bacterium that causes opportunistic infections in the human colon, usually after antibiotic exposure. *C. difficile* infection (CDI) can lead to diarrhoea, pseudomembranous colitis, toxic megacolon, intestinal perforation, multi-organ failure, and death.[1] A recent study showed that the incidence of recurrent CDI has disproportionately increased relative to CDI, therefore the demand for recurrent CDI therapies may be rising.[2]

The principle behind faecal microbiota transplant (FMT) is to use stool from a healthy donor to replace the microorganisms and ecosystem functions that are depleted in the gut of recurrent CDI patients. While FMT is highly effective at treating recurrent CDI,[3] it lacks a detailed mechanism of action and it is unclear whether all the microbes included in the preparations are required to resolve disease. There are concerns regarding the long-term safety, reproducibility, composition, and stability of FMT preparations,[4] and potential risks include transmission of infections, invasive administration routes, and concerns treating high-risk individuals (frail/elderly or immunosuppressed patients). In addition, as more studies describe the role of the gut microbiota in disease, it is unclear whether FMT could result in the transfer of a gut microbiota which later contributes to disease (e.g. colorectal cancer, obesity, inflammatory bowel disease, etc.).

Therefore, there is a risk that some FMT donations could, themselves, provide negative outcomes for the recipient, and, as such, there is a need to provide improved screening methods for FMT, both in terms of the donor and the recipient, to evaluate when FMT may be suitable or unsuitable. However, it is generally considered beneficial that FMT should be avoided if at all possible, and so there is a need to provide an improved means of treating CDI, ideally which do not involve the use of FMT.

*C. difficile* causes disease after germination, where cells change from their dormant spore state to their active vegetative state.[5] Previous studies have suggested that exposure to antibiotics alters the composition and functionality of the gut microbiota, changing the global metabolic profile to an environment that supports *C. difficile* germination and vegetative growth.[6]

Mechanistic studies are challenging to conduct in vivo due to the wide variety of factors which influence the composition and functionality of the gut microbiota. Firstly, samples from recurrent CDI patients prior to FMT are usually collected while they are still on suppressive vancomycin. Therefore, it is difficult to determine whether changes in specific bacteria or metabolites following FMT are due to the FMT administration, or whether these changes could have occurred in the absence of FMT due to recovery of the gut microbiota following cessation of antibiotic treatment. Changes in diet can also cause profound changes in the composition and functionality of the gut microbiota, especially short chain fatty acid (SCFA) production,[10] and diet is especially difficult to control in human studies. Recurrent CDI patients may eat differently before and after receiving FMT, and may eat differently from healthy controls. Studies on diet, the gut microbiota, and SCFA production have often relied on fermentation data in vitro and animal data due to the challenges associated with human studies.[11] Therefore, human studies could lead to "false positives" for mechanisms of *C. difficile* pathogenesis.

Data collected from chemostat studies can be used to complement microbiome data collected from human and animal studies to more easily determine a mechanism of action for specific disease states or interventions.[12] Chemostat models are artificial systems that mimic some of the spatial, temporal, and environmental conditions found in the human gut.[13] Chemostats have many advantages over human and animal studies, which have been discussed in detail previously.[12] Bacterial communities cultured in these models are highly reproducible, stable, complex, and representative of the bacterial communities found in vivo.[14,15] This means researchers can perform longitudinal studies in these systems that can directly link changes in the gut microbiota structure and function to an experimental intervention. Chemostats have previously been used to model CDI and test the effects of several treatments on *C. difficile* growth and pathogenesis (e.g. antibiotics,[16-19] bacteriophages,[20] and lactoferrin[21]).

The inventors used a twin-vessel single-stage distal gut chemostat model as a tool to study CDI and the effects of FMT under tightly-controlled conditions in vitro. Without wishing to be bound to any particular theory, the inventors hypothesize that exposure to antibiotics kills bacteria that perform important functions in the gut microbial ecosystem, resulting in a "metabolic dysbiosis" where the loss or reduction of specific microbial metabolic pathways creates an environment that promotes *C. difficile* germination and growth. Using their chemostat model and batch model, the inventors have surprisingly identified and characterised a number of biochemical compounds and metabolites, such as short or medium chain fatty acids, including butyrate, valerate, hexanoate and heptanoate, and bile salt hydrolases (BSH), that they believe are useful for therapeutically treat recurrent CDI that are well-defined, effective, and safe. They negate the need to use live microorganisms and circumvent the difficulties associated with FMT.

Hence, according to a first aspect of the invention, there is provided a compound of Formula (I):

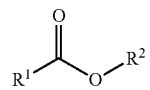

Formula (I)

wherein $R^1$ is a $C_2$ to $C_{10}$ alkyl or halogenated alkyl; and $R^2$ is hydrogen or a $C_1$ to $C_4$ alkyl or halogenated alkyl, and the $C_1$ to $C_4$ alkyl or halogenated alkyl is optionally substituted with between 1 and 5 substituents, wherein each substituent has the formula:

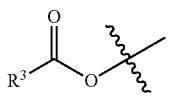

wherein each $R^3$ is independently a $C_2$ to $C_{10}$ alkyl or halogenated alkyl;
or a pharmaceutically acceptable salt, solvate, tautomeric form or polymorphic form thereof, for use in treating, preventing or ameliorating a *Clostridioides difficile* infection.

In one embodiment, $R^2$ is an unsubstituted $C_1$ to $C_4$ alkyl or halogenated alkyl.

Accordingly, the compound of Formula (I) may be a compound of Formula (Ia):

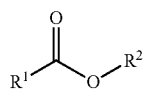

Formula (Ia)

wherein $R^1$ is a $C_2$ to $C_{10}$ alkyl or halogenated alkyl; and $R^2$ is hydrogen or a $C_1$ to $C_4$ alkyl or halogenated alkyl;
or a pharmaceutically acceptable salt, solvate, tautomeric form or polymorphic form thereof.

It may be appreciated that a halogenated alkyl is an alkyl where one or more hydrogen atoms have been replaced with a halogen. The halogen could be fluorine, chlorine, brome or iodine. Preferably, the halogen is fluorine. Accordingly, $R^1$ may be a $C_2$ to $C_{10}$ alkyl or fluorinated alkyl; and $R^2$ may be hydrogen or a $C_1$ to $C_4$ alkyl or fluorinated alkyl, optionally substituted with between 1 and 5 substituents, wherein the substituents are as defined above. Similarly, the or each $R^3$, in embodiments where it is present, may be a $C_2$ to $C_{10}$ alkyl or fluorinated alkyl.

$R^1$ may be ethyl, propyl, butyl, pentyl, hexyl, heptyl, octyl, nonyl or decyl or a fluorinated ethyl, propyl, butyl, pentyl, hexyl, heptyl, octyl, nonyl or decyl. The alkyl or halogenated alkyl is preferably a straight chain alkyl. Accordingly, most preferably, $R^1$ is ethyl, n-propyl, n-butyl, n-pentyl, n-hexyl, n-heptyl, n-octyl, n-nonyl or n-decyl or a fluorinated ethyl, n-propyl, n-butyl, n-pentyl, n-hexyl, n-heptyl, n-octyl, n-nonyl or n-decyl.

In embodiments where it is present, the or each $R^3$ may be ethyl, propyl, butyl, pentyl, hexyl, heptyl, octyl, nonyl or decyl or a fluorinated ethyl, propyl, butyl, pentyl, hexyl, heptyl, octyl, nonyl or decyl. The alkyl or halogenated alkyl is preferably a straight chain alkyl. Accordingly, most preferably, the or each $R^3$ is ethyl, n-propyl, n-butyl, n-pentyl, n-hexyl, n-heptyl, n-octyl, n-nonyl or n-decyl or a fluorinated ethyl, n-propyl, n-butyl, n-pentyl, n-hexyl, n-heptyl, n-octyl, n-nonyl or n-decyl.

$R^1$ may be $C_4$ to $C_{10}$ alkyl or halogenated alkyl. $R^1$ may be $C_4$ to $C_8$ alkyl or halogenated alkyl. Preferably, the halogenated alkyl is a fluorinated alkyl.

Preferably, $R^1$ is $C_4$ to $C_6$ alkyl or halogenated alkyl. Preferably, the halogenated alkyl is a fluorinated alkyl.

Preferably, $R^1$ is butyl or a fluorinated butyl. The butyl or fluorinated butyl may be linear, i.e. n-butyl. Most preferably, $R^1$ is n-butyl.

Preferably, $R^1$ is pentyl or a fluorinated pentyl. The pentyl or fluorinated pentyl may be linear, i.e. n-pentyl. Most preferably, $R^1$ is n-pentyl.

Preferably, $R^1$ is hexyl or a fluorinated hexyl. The hexyl or fluorinated hexyl may be linear, i.e. n-hexyl. Most preferably, $R^1$ is n-hexyl.

In embodiments where it is present, the or each $R^3$ may be $C_4$ to $C_{10}$ alkyl or halogenated alkyl. The or each $R^3$ may be $C_4$ to $C_8$ alkyl or halogenated alkyl. Preferably, the halogenated alkyl is a fluorinated alkyl. More preferably, the or each $R^3$ is $C_4$ to $C_6$ alkyl or halogenated alkyl. Preferably, the halogenated alkyl is a fluorinated alkyl.

Preferably, the or each $R^3$ is butyl or a fluorinated butyl. The butyl or fluorinated butyl may be linear, i.e. n-butyl. Most preferably, the or each $R^3$ is n-butyl.

Preferably, the or each $R^3$ is pentyl or a fluorinated pentyl. The pentyl or fluorinated pentyl may be linear, i.e. n-pentyl. Most preferably, the or each $R^3$ is n-pentyl.

Preferably, the or each $R^3$ is hexyl or a fluorinated hexyl. The hexyl or fluorinated hexyl may be linear, i.e. n-hexyl. Most preferably, the or each $R^3$ is n-hexyl.

It may be appreciated that a $C_1$ to $C_4$ alkyl may be methyl, ethyl, n-propyl, i-propyl, n-butyl or t-butyl. Similarly, a $C_1$ to $C_4$ fluorinated alkyl may be any of the aforementioned alkyl groups where one or more hydrogen atoms have been replaced with a halogen. Any of these groups may be substituted with between 1 and 5 substituents, wherein the or each substituent is as defined above. In a preferred embodiment, $R^2$ is hydrogen.

As described in the Examples, the inventors have surprisingly shown that valerate concentrations are decreased after treatment with clindamycin, which results in an increase in *C. difficile* total viable counts. The inventors have evaluated valerate concentrations following FMT, and also surprisingly found that the concentrations of valerate were increased and valerate precursors were decreased. In human stool, valerate was depleted before FMT, but restored at all time points measured (between one week and twelve weeks) after FMT. In addition, the inventors have also shown, using *C. difficile* batch cultures, that valerate decreases vegetative growth. The inventors have also tested other short or medium chain fatty acids such as hexanoate and heptanoate, and have shown that, surprisingly, they are also potent inhibitors of vegetative growth of *C. difficile*. Thus, the inventors have clearly identified that valerate, hexanoate, heptanoate salts, solvates, tautomers and polymorphs thereof, are highly effective at treating *C. difficile* infections.

Therefore, preferably valerate (pentanoate) or valeric acid (pentanoic acid) is used in treating, preventing or ameliorating a *Clostridioides difficile* infection.

The skilled person will be aware that valerate may also be referred to as pentanoate. In one embodiment, valeric acid, which may also be referred to as pentatonic acid, is provided herein as Formula (II), as follows:

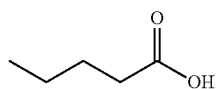

[Formula II]

In another embodiment, hexanoate (caproate) or hexanoic acid (caproic acid) is used in treating, preventing or ameliorating a *Clostridioides difficile* infection.

In one embodiment, hexanoic acid is provided herein as Formula (III), as follows:

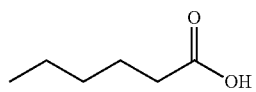

[Formula III]

In another embodiment, heptanoate (enanthate) or heptanoic acid (enanthic acid) is used in treating, preventing or ameliorating a *Clostridioides difficile* infection.

In one embodiment, heptanoic acid is provided herein as Formula (IV), as follows:

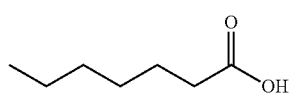

[Formula IV]

The invention also extends to other medium chain fatty acids. Accordingly, in another embodiment, octanoate (caprylate) or octanoic acid (caprylic acid) is used in treating, preventing or ameliorating a *Clostridioides difficile* infection.

In one embodiment, octanoic acid is provided herein as Formula (V), as follows:

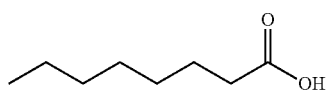

[Formula V]

In another embodiment, pelargonate (nonanoate) or pelargonic acid (nonanoic acid) is used in treating, preventing or ameliorating a *Clostridioides difficile* infection.

In one embodiment, pelargonic acid is provided herein as Formula (VI), as follows:

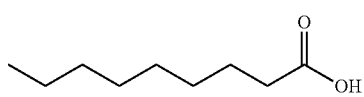

[Formula VI]

In an alternative embodiment, $R^2$ is a $C_1$ to $C_4$ alkyl or halogenated alkyl, and the $C_1$ to $C_4$ alkyl or halogenated alkyl is substituted with between 1 and 5 substituents.

Preferably, $R^2$ is a $C_1$ to $C_4$ alkyl or halogenated alkyl, and the $C_1$ to $C_4$ alkyl or halogenated alkyl is substituted with between 1 and 4 substituents or between 2 and 3 substituents. Most preferably, $R^2$ is a $C_1$ to $C_4$ alkyl or halogenated alkyl, and the $C_1$ to $C_4$ alkyl or halogenated alkyl is substituted with 2 substituents.

Accordingly, the compound may be a compound of Formula (VII):

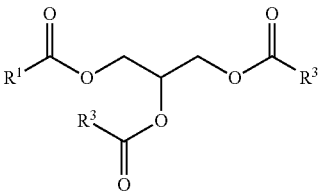

[Formula VII]

In some embodiments, $R^1$ and each $R^3$ may be identical.

In one embodiment, $R^1$ and each $R^3$ may be butyl or a fluorinated butyl. The butyl or fluorinated butyl may be linear, i.e. n-butyl. Most preferably, $R^1$ and each $R^3$ are n-butyl. The skilled person will understand trivalerin or trivalerate (Glycerol trivalerate; 1,3-bis(pentanoyloxy)propan-2-yl pentanoate) may be referred to as the glycerol ester of either pentanoic acid/pentanoate or valeric acid/valerate, and is provided herein as Formula (VII), as follows.

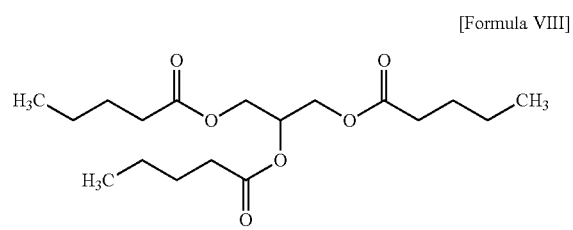

[Formula VIII]

In an alternative embodiment, $R^1$ and each $R^3$ may be pentyl or a fluorinated pentyl. The pentyl or fluorinated pentyl may be linear, i.e. n-pentyl. Most preferably, $R^1$ and each $R^3$ are n-pentyl. Accordingly, the compound of Formula (VII) may be trihexanoin, which may be referred to as 2,3-di(hexanoyloxy)propyl hexanoate or glycerol trihexanoate.

In an alternative embodiment, $R^1$ and each $R^3$ may be hexyl or a fluorinated hexyl. The hexyl or fluorinated hexyl may be linear, i.e. n-hexyl. Most preferably, $R^1$ and each $R^3$ are n-hexyl. Accordingly, the compound of Formula (VII) may be triheptanoin, which may be referred to as propane-1,2,3-triyl triheptanoate or glycerol triheptanoate.

In an alternative embodiment, $R^1$ and each $R^3$ may be heptyl or a fluorinated heptyl. The hexyl or fluorinated heptyl may be linear, i.e. n-heptyl. Most preferably, $R^1$ and each $R^3$ are n-heptyl. Accordingly, the compound of Formula (VII) may be trioctanoin, which may be referred to as glycerol trioctanoate.

In an alternative embodiment, $R^1$ and each $R^3$ may be octyl or a fluorinated octyl. The hexyl or fluorinated octyl may be linear, i.e. n-octyl. Most preferably, $R^1$ and each $R^3$ are n-octyl. Accordingly, the compound of Formula (VII) may be tripelargonin, which may be referred to as glyceryl pelargonate.

Pharmaceutically acceptable salts include any salt of the compound of Formula (I to (VIII) provided herein which retains its biological properties and which is not toxic or otherwise undesirable for pharmaceutical use. The pharmaceutically acceptable salt may be derived from a variety of organic and inorganic counter-ions well known in the art.

The pharmaceutically acceptable salt may comprise an acid addition salt formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids. Alternatively, the pharmaceutically acceptable salt may comprise a base addition salt formed when an acidic proton present in the parent compound is either replaced by a metal ion, e.g., an alkali metal ion, an alkaline earth ion, an aluminium ion, alkali metal or alkaline earth metal hydroxides, such as sodium, potassium, calcium, magnesium, aluminium, lithium, zinc, and barium hydroxide, or coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

A pharmaceutically acceptable solvate refers to a compound of Formula (I to (VIII) provided herein, or a salt thereof, that further includes a stoichiometric or non-stoichiometric amount of solvent bound by non-covalent intermolecular forces. Where the solvent is water, the solvate is a hydrate.

The compound of Formula (I) to (VIII) provided or a pharmaceutically acceptable salt, solvate, tautomeric form or polymorphic form thereof, may be modified to aid delivery to the site of treatment, for example the gut. In one embodiment, the compound of Formula (I) to (VIII) provided herein may be modified to comprise an inulin ester. In another embodiment, the compound of Formula (I) to (VIII) may be modified to trivalerin, trihexanoin, triheptanoin, trioctanoin or tripelargonin.

The inventors have also considered other biochemical molecules and metabolites that may be used to treat $C.$ difficile infections. Without wishing to be bound to any particular theory, the inventors have also shown that a key vulnerability to CDI is a loss of gut microbiota members which produce BSH and 7-α-dehydroxylase (i.e. secondary to antibiotic use), and the consequent enrichment in taurocholic acid (TCA) (promoting $C.$ difficile germination) and loss of deoxycholic acid (DCA) (permitting vegetative growth). They further hypothesised that successful FMT reconstitutes the gut microbiota with BSH- and 7-α-dehydroxylase-producing organisms, and restores the normal bile acid milieu of the gut.

For example, and without wishing to be bound to any particular hypothesis, bile salt hydrolase (BSH) enzymes can be used to degrade taurocholic acid and prevent $C.$ difficile spore germination. To prevent CDI initiation and relapse following the cessation of antibiotics, it is important to maintain low levels of TCA in the gut. One way to accomplish this would be to ensure the maintenance of bile salt hydrolase (BSH) enzymes during and after antibiotic exposure. These enzymes are produced by commensal gut bacteria and are responsible for deconjugating tauro- and glyco-conjugated bile acids. Antibiotics may kill BSH-producing bacteria, resulting in the accumulation of TCA in the gut. Therefore, re-inoculation of BSH-producing bacteria with FMT may be responsible for degrading TCA present following the cessation of antibiotics, and prevent the germination of $C.$ difficile spores.

However, a safer way of restoring BSH activity in the gut microbiomes of CDI patients would be to administer purified BSH enzyme preparations to avoid the administration of live microorganisms. Furthermore, while DCA can inhibit $C.$ difficile vegetative growth, it appears that DCA can also encourage spore germination at specified concentrations.[30]. Thus, a better strategy to prevent CDI prior to antibiotic exposure would be to prevent germination altogether by degrading TCA, a potent pro-germinant, using BSH enzymes, subsequently removes key triggers for $C.$ difficile germination and vegetative growth.

Preferably, the compound of formula (I) may be used in combination with a bile salt hydrolase (BSH) or an active variant thereof. The inventors believe that a bile salt hydrolase (BSH) or an active variant thereof on its own can be used to treat a CDI.

Accordingly, in a second aspect of the invention, there is provided a bile salt hydrolase (BSH) or an active variant thereof, for use in treating, preventing or ameliorating a *Clostridioides difficile* infection.

Preferably, the bile salt hydrolase or active variant thereof metabolises taurocholic acid.

Preferably, the bile salt hydrolase or active variant thereof is selected from a group consisting of *Ruminococcus gnavus* BSH, *Roseburia inulinivorans* BSH, *Ruminococcus lactaris* BSH, *Bacteroides pectinophilus* BSH, *Roseburia intestinalis* BSH, *Bacteroides plebius* BSH, *Bacteroides ovatus* BSH, *Bacteroides intestinalis* BSH, *Bacteroides eggerthi* BSH, *Alistipes putredinis* BSH, *Bacteroides coprophilus* BSH, *Bacteroides dorei* BSH, *Bacteroides coprocola* BSH, *Parabacteroides distasonis* BSH, *Bifidobacterium pseudocatenulatum* BSH, *Bifidobacterium kashiwanohense* BSH, *Bifidobacterium catenulatum* BSH, *Bifidobacterium bifdum* BSH, *Bifidobacterium longum* BSH, *Bifidobacetrium merycicum* BSH, *Bifidobacterium angulatum* BSH, *Collinesella bouchesdurhonensis* BSH, *Bifidobacterium thermacidophilum* BSH, *Bifidobacterium thermophilum* BSH, *Bifidobacterium adolescentis* BSH, *Enterococcus faecium* BSH, *Enterococcus faecalis* BSH, *Enterococcus gallinarum* BSH, *Listeria monocytogenes* BSH, *Lactobacillus planturum* BSH, *Clostridium perfringens* BSH, *Enterococcus casseliflavus* BSH, *Methanosphaera stadtmaniae* BSH, *Methanobrevibacter smithii* BSH, *Lactobacillus acidophilus* BSH, *Lactobacillus reuteri* BSH, *Lactobacillus crispatus* BSH, *Lactobacillus ultunensis* BSH, *Lactobacillus salivarius* BSH, *Slackia heliotrinireducens* BSH, *Clostridium bolteae* BSH, *Butyriovibrio crossotus* BSH, *Blatia obeum* BSH, *Eubacterium rectale* BSH, *Faecalibacterium prausnitzii* BSH, and *Bacteroides vulgatus* BSH.

More preferably, the bile salt hydrolase or active variant thereof is *Bifidobacterium adolescentis* BSH.

In a preferred embodiment, the bile salt hydrolase has the amino acid sequence provided herein as SEQ ID NO: 1, as follows:

[SEQ ID NO: 1]
MCTGVRFSDEEGNMYFGRNLDWSFSYGESILATPRGYHYDNVFGASGKAT

PNAVIGVGVVMADRPMYFDCANEHGLAIAGLNFPGYAEFVHEPVEGTDN

VATFEFPLWVARNFDSVDEVEKALKNVTIVSQIVPGQQESLLHWIIGDSER

-continued

SIVVEQMADGMHVHHDDVDVLTNQPTFGFHMENLRNYMCVGNEMAEP

ATWGKASLSAWGAGVSMHGIPGDVSSPSRFVRVAYANTHYPQQEGEAA

NVSRLFHTLGSVQMVDGMAKMGNGQFERTLFTSGYSSKTNTYYMNTYDD

PAIRSYAMADFDMDSSELITAA

Hence, in a preferred embodiment, the bile salt hydrolase or active variant thereof comprises an amino acid sequence substantially as set out in SEQ ID NO: 1, or a functional fragment or variant thereof.

In another embodiment, the bile salt hydrolase is encoded by a nucleotide sequence (*Bifidobacterium adolescentis* WP_085380359.1), which is provided herein as SEQ ID NO: 2, as follows:

[SEQ ID NO: 2]
ATGTGTACCGGTGTTCGTTTTAGTGATGAAGAGGGCAATATGTATTTTG

GTCGTAATCTGGATTGGAGCTTTAGCTATGGTGAAAGCATTCTGGCAAC

ACCGCGTGGTTATCACTATGATAATGTTTTTGGTGCAAGCGGTAAAGCA

ACCCCGAATGCAGTTATTGGTGTTGGTGTTGTTATGGCAGATCGTCCGA

TGTATTTCGATTGTGCAAATGAACATGGTCTGGCAATTGCAGGTCTGAA

TTTTCCGGGTTATGCAGAATTTGTGCATGAACCGGTTGAAGGCACCGAT

AATGTTGCAACCTTTGAATTTCCGCTGTGGGTTGCACGTAATTTTGATA

GCGTTGATGAAGTTGAGAAAGCCCTGAAAAATGTTACCATTGTGAGCCA

GATTGTTCCGGGTCAGCAAGAAAGCCTGCTGCATTGGATTATTGGTGAT

AGCGAACGTAGCATTGTTGTTGAGCAGATGGCAGATGGTATGCATGTTC

ATCACGATGATGTTGATGTTCTGACCAATCAGCCGACCTTTGGTTTTCA

TATGGAAAATCTGCGCAACTATATGTGCGTGGGTAATGAAATGGCAGAA

CCGGCAACCTGGGGTAAAGCCAGCCTGAGCGCATGGGGTGCCGGTGTTA

GCATGCATGGTATTCCGGGTGATGTTAGCAGCCCGAGCCGTTTTGTTCG

TGTTGCCTATGCAAATACCCATTATCCGCAGCAAGAGGGTGAAGCAGCA

AATGTTAGCCGTCTGTTTCATACCCTGGGTAGCGTTCAGATGGTTGATG

GCATGGCAAAAATGGGTAATGGTCAGTTTGAACGTACCCTGTTTACCAG

CGGTTATAGCAGCAAAACCAACACCTATTATATGAACACCTATGACGAT

CCGGCAATTCGTAGCTATGCAATGGCAGATTTTGATATGGATAGCAGCG

AACTGATTACCGCAGCA

Hence, in a preferred embodiment, the bile salt hydrolase or active variant thereof is encoded by a nucleotide sequence substantially as set out in SEQ ID NO: 2, or a functional fragment or variant thereof.

The compounds (i.e. a compound of any one of Formulae (I) to (VIII) and bile salt hydrolase (BSH) or an active variant thereof), for use in the first and second aspect of the invention may be used in combination to provide a particularly effective means of treating *C. difficile* infections.

Preferably, therefore the bile salt hydrolase (BSH) or an active variant thereof may be used in combination with the compound of formula (I).

Accordingly, in a third aspect of the invention there is provided: (i) a bile salt hydrolase (BSH) or an active variant thereof, and (ii) a compound of Formula (I):

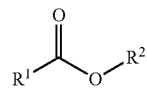
Formula (I)

wherein $R^1$ is a $C_2$ to $C_{10}$ alkyl or halogenated alkyl; and $R^2$ is hydrogen or a $C_1$ to $C_4$ alkyl or halogenated alkyl, and the $C_1$ to $C_4$ alkyl or halogenated alkyl is optionally substituted with between 1 and 5 substituents, wherein each substituent has the formula:

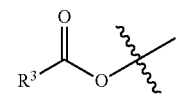

wherein each $R^3$ is independently a $C_2$ to $C_{10}$ alkyl or halogenated alkyl;

or a pharmaceutically acceptable salt, solvate, tautomeric form or polymorphic form thereof, for use in treating, preventing or ameliorating a *Clostridioides difficile* infection.

Preferably, the compound of Formula (I), or a pharmaceutically acceptable salt, solvate, tautomeric form or polymorphic form thereof is as described in the first aspect.

Preferably, the bile salt hydrolase (BSH) or an active variant thereof is as described in the second aspect.

As described in the Examples, the inventors have found that succinate is transiently increased in chemostat cultures with clindamycin dosing, but is negatively correlated with *C. difficile* total viable counts (TVC). While not wishing to be bound to any theory, the inventors believe that the negative correlation between *C. difficile* TVC and succinate is because *C. difficile* uses succinate for growth. Accordingly, another strategy to treat *C. difficile* infection is to give *C. difficile* vegetative cells a competitive disadvantage by maintaining succinate metabolism during antibiotic exposure by administering succinate-metabolising enzymes, so that succinate is no longer available for *C. difficile* growth.

Accordingly, in a fourth aspect of the invention there is provided: (i) a succinate-metabolising enzyme or an active variant thereof; and (ii) a bile salt hydrolase (BSH) or an active variant thereof, and/or (iii) a compound of Formula (I):

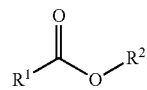
Formula (I)

wherein $R^1$ is a $C_2$ to $C_{10}$ alkyl or halogenated alkyl; and $R^2$ is hydrogen or a $C_1$ to $C_4$ alkyl or halogenated alkyl, and the $C_1$ to $C_4$ alkyl or halogenated alkyl is optionally substituted with between 1 and 5 substituents, wherein each substituent has the formula:

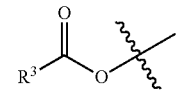

wherein each $R^3$ is independently a $C_2$ to $C_{10}$ alkyl or halogenated alkyl;
or a pharmaceutically acceptable salt, solvate, tautomeric form or polymorphic form thereof, for use in treating, preventing or ameliorating a *Clostridioides difficile* infection.

Preferably, the compound of Formula (I), or a pharmaceutically acceptable salt, solvate, tautomeric form or polymorphic form thereof is as defined in the first aspect.

Preferably, the bile salt hydrolase (BSH) or an active variant thereof is as defined in the second aspect.

The skilled person will be aware of suitable succinate-metabolising enzymes.

The succinate may be metabolised by the action of acyl-CoA transferase, which catalyses the reaction:
succinate+propionyl-CoA→succinyl-CoA+propionate, as described in Macy et al. (1978). Pathway of Succinate and Propionate Formation in *Bacteroides fragilis*. Journal of Bacteriology, 134(1):84-91.

Thus, preferably the succinate-metabolising enzyme is acyl-CoA transferase.

The succinate may be metabolised by the action of CoA-transferase, which converts succinate to succinyl-CoA, as described in Buckel et al. (2001) Unusual enzymes involved in five pathways of glutamate fermentation. Applied Microbiology and Biotechnology, 57(3):263-273.

Thus, preferably the succinate-metabolising enzyme is CoA-transferase.

The succinate may be metabolilsed to two acetates in the presence of ethanol, as described in Kenealy et al. (1985) Studies on the substrate range of *Clostridium kluyveri*; the use of propanol and succinate. Archives of Microbiology, 141(3):187-194.

Thus, in one embodiment, and while not wishing to be bound to any particular theory, uses of the invention may comprise a combinatorial therapy comprising: 1) directly supplementing the gut with a compound of Formula (I):

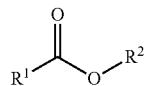

Formula (I)

wherein $R^1$ is a $C_2$ to $C_{10}$ alkyl or halogenated alkyl; and $R^2$ is hydrogen or a $C_1$ to $C_4$ alkyl or halogenated alkyl, and the $C_1$ to $C_4$ alkyl or halogenated alkyl is optionally substituted with between 1 and 5 substituents, wherein each substituent has the formula:

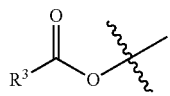

wherein each $R^3$ is independently a $C_2$ to $C_{10}$ alkyl or halogenated alkyl;
or a pharmaceutically acceptable salt, solvate, tautomeric form or polymorphic form thereof (to inhibit *C. difficile* vegetative growth);
2) directly supplementing the gut with bile salt hydrolase (BSH) enzymes or active variants thereof (to degrade taurocholic acid and prevent *C. difficile* spore germination); and
3) directly supplementing the gut with a succinate-metabolising enzyme (to degrade succinate and give *C. difficile* vegetative cells a competitive disadvantage).

The skilled person would also consider providing 7-α-dehydroxylase in combination with the compounds, polypeptides and mixtures of the first to fourth aspects of the invention.

The skilled person would also consider the use of nucleic acids encoding polypeptides of the present invention, and vectors comprising nucleic acids encoding polypeptides of the present invention.

Accordingly, in a fifth aspect of the invention there is provided a vector comprising a nucleic acid sequence encoding a bile salt hydrolase (BSH) or an active variant thereof, for use in treating, preventing or ameliorating a *Clostridioides difficile* infection.

The vector may comprise a nucleic acid encoding any bile salt hydrolase (BSH) or an active variant thereof as defined in the second aspect.

The vector may further comprise a nucleic acid sequence encoding a succinate-metabolising enzyme or active variant thereof, and preferably a succinate-metabolising enzyme as defined in the fourth aspect.

The vector of the fifth aspect may be used in combination with a compound of formula (I), or a pharmaceutically acceptable salt, solvate, tautomeric form or polymorphic form thereof as defined in the first aspect and/or a succinate-metabolising enzyme or active variant thereof as defined in the fourth aspect.

The vector may for example be a plasmid, cosmid or phage and/or be a viral vector. Such recombinant vectors are highly useful in the delivery systems of the invention for transforming cells with the nucleic acid molecule. The nucleic acid sequence may preferably be a DNA sequence.

Preferably, the vector of the fifth aspect is recombinant. Recombinant vectors may also include other functional elements. For example, they may further comprise a variety of other functional elements including a suitable promoter for initiating transgene expression upon introduction of the vector in a host cell. For instance, the vector is preferably capable of autonomously replicating in the nucleus of the host cell. In this case, elements which induce or regulate DNA replication may be required in the recombinant vector. Alternatively, the recombinant vector may be designed such that it integrates into the genome of a host cell. In this case, DNA sequences which favour targeted integration (e.g. by homologous recombination) are envisaged. Suitable promoters may include the SV40 promoter, CMV, EF1a, PGK, viral long terminal repeats, as well as inducible promoters, such as the Tetracycline inducible system, as examples. The cassette or vector may also comprise a terminator, such as the Beta globin, SV40 polyadenylation sequences or synthetic polyadenylation sequences. The recombinant vector may also comprise a promoter or regulator or enhancer to control expression of the nucleic acid as required. Tissue specific promoter/enhancer elements may be used to regulate expression of the nucleic acid in specific cell types, for example, gut cells. The promoter may be constitutive or inducible.

The vector may also comprise DNA coding for a gene that may be used as a selectable marker in the cloning process, i.e. to enable selection of cells that have been transfected or transformed, and to enable the selection of cells harbouring vectors incorporating heterologous DNA. For example, ampicillin, neomycin, puromycin or chloramphenicol resistance is envisaged. Alternatively, the selectable marker gene may be in a different vector to be used simultaneously with the vector containing the transgene. The cassette or vector may also comprise DNA involved with regulating expression of the transgene, or for targeting the expressed polypeptide to a certain part of the host cell.

Purified vector may be inserted directly into a host cell by suitable means, e.g. direct endocytotic uptake. The vector may be introduced directly into cells of a host subject (e.g. a eukaryotic or prokaryotic cell) by transfection, infection, electroporation, microinjection, cell fusion, protoplast fusion or ballistic bombardment. Alternatively, vectors of the invention may be introduced directly into a host cell using a particle gun.

The nucleic acid molecule may (but not necessarily) be one, which becomes incorporated in the DNA of cells of the subject being treated. Undifferentiated cells may be stably transformed leading to the production of genetically modified daughter cells (in which case regulation of expression in the subject may be required e.g. with specific transcription factors or gene activators). Alternatively, the delivery system may be designed to favour unstable or transient transformation of differentiated cells in the subject being treated. When this is the case, regulation of expression may be less important because expression of the DNA molecule will stop when the transformed cells die or stop expressing the protein (ideally when the required therapeutic effect has been achieved).

The nucleic acid molecule may be transferred to the cells of a subject to be treated by transfection, infection, microinjection, cell fusion, protoplast fusion or ballistic bombardment. For example, transfer may be by ballistic transfection with coated gold particles, liposomes containing the nucleic acid molecule, viral vectors (e.g. adenovirus) and means of providing direct nucleic acid uptake (e.g. endocytosis) by application of the nucleic acid molecule directly.

Preferably, the vector is introduced into a microorganism, such that the microorganism is capable of producing the bile salt hydrolase (BSH) or an active variant thereof, and can be introduced into a subject's gut to catalyse degradation of bile salts.

Accordingly, in a sixth aspect of the invention there is provided a microorganism expressing a bile salt hydrolase (BSH) or an active variant thereof, for use in the prevention, treatment or amelioration of a *Clostridioides difficile* infection.

Preferably, the bile salt hydrolase (BSH) or an active variant thereof is as defined in the second aspect of the invention.

The microorganism may be a bacterium, yeast or fungus. Preferably, the microorganism is a bacterium. The bacterium may be a gram-positive or gram-negative bacterium.

Preferably, the microorganism is selected from a group consisting of *Ruminococcus gnavus, Roseburia inulinivorans* BSH, *Ruminococcus lactaris, Bacteroides pectinophilus, Roseburia intestinalis, Bacteroides plebius, Bacteroides ovatus, Bacteroides intestinalis, Bacteroides eggerthi, Alistipes putredinis, Bacteroides coprophilus, Bacteroides dorei, Bacteroides coprocola, Parabacteroides distasonis, Bifidobacterium pseudocatenulatum, Bifidobacterium kashiwanohense, Bifidobacterium catenulatum, Bifidobacterium bifdum, Bifidobacterium longum, Bifidobacetrium merycicum, Bifdobacterium angulatum, Collinesella bouchesdurhonensis, Bifidobacterium thermacidophilum, Bifdobacterium thermophilum, Bifidobacterium adolescentis, Enterococcus faecium, Enterococcus faecalis, Enterococcus gallinarum, Listeria monocytogenes, Lactobacillus planturum, Clostridium perfringens, Enterococcus casseliflavus, Methanosphaera stadtmaniae, Methanobrevibacter smithii, Lactobacillus acidophilus, Lactobacillus reuteri, Lactobacillus crispatus, Lactobacillus ultunensis, Lactobacillus salivarius, Slackia heliotrinireducens, Clostridium bolteae, Butyriovibrio crossotus, Blautia obeum, Eubacterium rectale, Faecalibacterium prausnitzii*, and *Bacteroides vulgatus*.

Preferably the microorganism is *Bifidobacterium adolescentis*.

The microorganism of the sixth aspect may be used in combination with the compound of Formula (I) or a pharmaceutically acceptable salt, solvate, tautomeric form or polymorphic form thereof as defined in the first aspect of the invention and/or the succinate-metabolising enzyme or active variant thereof as defined in the fourth aspect of the invention.

While not wishing to be bound to any particular theory, the inventors have shown that short and medium chain fatty acid precursors, such as valerate, are present at high concentrations in patients with *C. difficile* infection while short and medium chain fatty acid precursors, such as valerate, are present in low concentrations when compared to uninfected individuals.

Thus, it would be advantageous to provide a means of converting short or medium chain fatty acids precursors into short or medium chain fatty acids, such as valerate.

Accordingly, in an seventh aspect of the invention there is provided a microorganism capable of converting short or medium chain fatty acid precursors, present in the gut, to short or medium chain fatty acids, for use in the prevention, treatment or amelioration of a *Clostridioides difficile* infection.

Preferably, the short or medium chain fatty acid is saturated.

Preferably the short or medium chain fatty acid is selected from the group consisting of: propionate, butyrate, valerate, hexanoate, heptanoate, octanoate, pelargonate, nonanoate and decanoate.

Preferably, the short or medium chain fatty acid is valerate, hexanoate, heptanoate, octanoate or pelargonate as defined in the first aspect. Most preferably, the short or medium chain fatty acid is valerate, hexanoate or heptanoate, as defined in the first aspect.

Preferably, the short or medium chain fatty acid is valerate as defined in the first aspect. Preferably, the short or medium chain fatty acid is hexanoate as defined in the first aspect. Preferably, the short or medium chain fatty acid is heptanoate as defined in the first aspect. Preferably, the short or medium chain fatty acid is octanoate as defined in the first aspect. Preferably, the short or medium chain fatty acid is pelargonate as defined in the first aspect.

There are several different metabolic pathways that lead to valerate production. 5-aminovalerate is a product of the anaerobic degradation of protein hydrolysates by members of the gut microbiota. In this pathway, as show in in table 1/FIG. 30, proline is reduced to 5-aminovalerate, which the skilled person will be aware is also referred to as δ-aminovalerate, by proline reductase in a Stickland-type fermentation.[32-34] 5-aminovalerate is fermented to valerate in a series of reactions mediated by gut bacteria. Accordingly, the microorganism of the seventh aspect may express an enzyme selected from a group consisting of: 5-aminovalerate aminotransferase, 5-hydroxyvalerate dehydrogenase and 5-hydroxyvalerate CoA-transferase. 5-hydroxyvaleryl-Coa dehydrogenase/dehydratase, 2,4-pentadienoyl-CoA reductase, 3-pentenoyl-CoA Δ 3, A 2-isomerase, Enzymes of the oxidation of fatty acids, 5-hydroxyvalerate CoA-transferase, phosphate acetyltransferase and acetate kinase. Preferably, the microorganism of the seventh aspect expresses all of these enzymes.

Alternatively, where the fatty acid is propionate, the microorganism of the seventh aspect may express an enzyme selected from a group consisting of: acetate kinase; propionate kinase; propionate CoA-transferase; 2,3-dimethylmalate lyase; acetate-CoA ligase; acetate-CoA ligase (ADP-forming); propionate-CoA ligase. Preferably, the microorganism of the seventh aspect expresses all of these enzymes.

Alternatively, where the fatty acid is butyrate, the microorganism of the seventh aspect may express an enzyme selected from a group consisting of: 2-enoate reductase; butyrate kinase; acetate CoA-transferase; butyrate-acetoacetate CoA-transferase; phorbol-diester hydrolase; 5'-acylphosphoadenosine hydrolase; beta-diketone hydrolase; medium-chain acyl-CoA ligase. Preferably, the microorganism of the seventh aspect expresses all of these enzymes.

Alternatively, where the fatty acid is hexanoate, the microorganism of the seventh aspect may express alkylamidase.

Alternatively, where the fatty acid is Octanoate, the microorganism of the seventh aspect may express dodecanoyl-[acyl-carrier-protein] hydrolase.

Alternatively, where the fatty acid is Decanoate, the microorganism of the seventh aspect may express decanoyl-[acyl-carrier protein] hydrolase.

In another metabolic pathway, some *Clostridium* species can ferment ethanol and propionate to valerate. The inventors found that ethanol and propionate increased after clindamycin dosing and decreased following FMT treatment. While not wishing to be held to any particular theory, together, the changes in the levels of valerate and valerate precursors (5-aminovalerate, ethanol, and propionate) over the course of the inventor's chemostat experiments suggests disruption of the valerate pathway due to antibiotics created an environment that permitted *C. difficile* vegetative growth.

Thus, in one embodiment, the precursor is 5-aminovalerate. In another embodiment, the precursors are ethanol and propionate.

The microorganism may be a bacterium, yeast or fungus. Preferably the microorganism is a bacterium.

Preferably, the microorganism is *Megasphaera Oscillibacter*, or *Clostridium* species.

The microorganism of the seventh aspect may be used in combination with the compound of Formula (I) or a pharmaceutically acceptable salt, solvate, tautomeric form or polymorphic form thereof as defined in the first aspect of the invention, the bile salt hydrolase (BSH) or an active variant thereof of the second aspect and/or the succinate metabolising enzyme or active variant thereof as defined in the fourth aspect of the invention.

Preferably, the agents of the first to seventh aspects of the present invention can be used in patients that are at risk of *C. difficile* infection. For example, patients receiving antibiotic treatment, or that have been immunocompromised, for example those receiving chemotherapy. In such instances the metabolites of the invention may be provided to prevent *C. difficile* infection and/or to treat *C. difficile* infection.

The agents of the first to seventh aspects of the invention may be used in combination with FMT, antibiotics or as a standalone treatment.

According to an eighth aspect of the invention, there is provided a *C. difficile* treatment pharmaceutical composition comprising the compound of Formula (I):

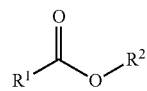

Formula (I)

wherein $R^1$ is a $C_2$ to $C_{10}$ alkyl or halogenated alkyl; and $R^2$ is hydrogen or a $C_1$ to $C_4$ alkyl or halogenated alkyl, and the $C_1$ to $C_4$ alkyl or halogenated alkyl is optionally substituted with between 1 and 5 substituents, wherein each substituent has the formula:

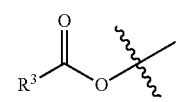

wherein each $R^3$ is independently a $C_2$ to $C_{10}$ alkyl or halogenated alkyl;

or a pharmaceutically acceptable salt, solvate, tautomeric form or polymorphic form thereof and/or bile salt hydrolase (BSH) or an active variant thereof, and a pharmaceutically acceptable vehicle.

The pharmaceutical composition of the eighth aspect may further comprise a succinate-metabolising enzyme or active variant thereof.

The pharmaceutical composition may comprise the compound of Formula (I) or a pharmaceutically acceptable salt, solvate, tautomeric form or polymorphic form thereof as defined in the first aspect of the invention.

The pharmaceutical composition may comprise the bile salt hydrolase (BSH) or active variant thereof as defined in the second aspect of the invention.

The pharmaceutical composition may comprise a succinate-metabolising enzyme or active variant thereof as defined in the fourth aspect of the invention.

Preferably, the pharmaceutical composition comprises the compound of Formula (I) or a pharmaceutically acceptable salt, solvate, tautomeric form or polymorphic form thereof as defined in the first aspect of the invention.

When trivalerin or trivalerate (Glycerol trivalerate; 1,3-bis(pentanoyloxy)propan-2-yl pentanoate) according to the first aspect of the invention is used, the pharmaceutical composition may further comprise a lipase and/or pancreatic enzyme.

The antibiotic compositions and formulations according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given.

The *C. difficile* treatment compositions and formulations of the invention may be used in a number of ways. For instance, oral administration may be required, in which case the agents may be contained within a composition that may, for example, be ingested orally in the form of a tablet, capsule or liquid. *C. difficile* treatment compositions and formulations of the invention may be administered by inhalation (e.g., intranasally). Compositions may also be formulated for topical use. For instance, creams or ointments may be applied to the skin.

*C. difficile* treatment compositions and formulations according to the invention may also be incorporated within a slow- or delayed-release device. Such devices may, for example, be inserted on or under the skin, and the medicament may be released over weeks or even months. The device may be located at least adjacent to the treatment site. Such devices may be particularly advantageous when long-term treatment with agents used according to the invention is required and which would normally require frequent administration (e.g., at least daily administration).

In a preferred embodiment, *C. difficile* treatment compositions and formulations according to the invention may be administered to a subject by injection into the blood stream or directly into a site requiring treatment. Injections may be intravenous (bolus or infusion) or subcutaneous (bolus or infusion), or intradermal (bolus or infusion).

It will be appreciated that the amount of the *C. difficile* treatment compositions and formulations that is required is determined by its biological activity and bioavailability, which in turn depends on the mode of administration, the physiochemical properties of the *C. difficile* treatment compositions and formulations, and whether they are being used as a monotherapy or in a combined therapy. The frequency of administration will also be influenced by the half-life of the *C. difficile* treatment compositions and formulations within the subject being treated. Optimal dosages to be administered may be determined by those skilled in the art, and will vary with the particular *C. difficile* treatment compositions and formulations in use, the strength of the pharmaceutical composition, the mode of administration, and the advancement of the bacterial infection. Additional factors depending on the particular subject being treated will result in a need to adjust dosages, including subject age, weight, gender, diet, and time of administration.

Generally, a daily dose of between 0.001 μg/kg of body weight and 10 mg/kg of body weight, or between 0.01 μg/kg of body weight and 1 mg/kg of body weight, of *C. difficile* treatment composition or formulation according to the invention may be used for treating, ameliorating, or preventing bacterial infection, depending upon which *C. difficile* treatment composition or formulation is used. Preferably, valeric acid, analogue or a pharmaceutically acceptable salt or solvate thereof are applied at a rate of at least 1 mM in the intestinal content, more preferably at least 10 mM in the intestinal content, most preferably at least 30 mM in the intestinal content.

The *C. difficile* treatment composition or formulation may be administered before, during or after onset of the bacterial infection. Daily doses may be given as a single administration (e.g., a single daily injection). Alternatively, the *C. difficile* treatment composition or formulation may require administration twice or more times during a day. As an example, the *C. difficile* treatment composition or formulation may be administered as two (or more depending upon the severity of the bacterial infection being treated) daily doses of between 0.07 g and 700 mg (i.e., assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of *C. difficile* treatment composition or formulation according to the invention to a patient without the need to administer repeated doses.

It will be appreciated that patients tend to get CDI when they are in hospital and taking antibiotics. Accordingly, it is preferred that the *C. difficile* treatment compositions or formulations of the invention are administered prior to hospital entry (e.g., as prescribed over the counter), and then during the stay at hospital, and for a few days or weeks post-discharge. The *C. difficile* treatment composition or formulation may therefore be used to prevent relapse of the bacterial infection.

Known procedures, such as those conventionally employed by the pharmaceutical industry (e.g., in vivo experimentation, clinical trials, etc.), may be used to form specific formulations of the *C. difficile* treatment composition according to the invention and precise therapeutic regimes (such as daily doses of the antibiotic composition or formulation and the frequency of administration).

According to an ninth aspect, there is provided a method of preparing the *C. difficile* treatment pharmaceutical composition according to the eighth aspect, the method comprising contacting a compound of Formula (I):

Formula (I)

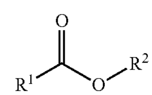

wherein $R^1$ is a $C_2$ to $C_{10}$ alkyl or halogenated alkyl; and $R^2$ is hydrogen or a $C_1$ to $C_4$ alkyl or halogenated alkyl, and the $C_1$ to $C_4$ alkyl or halogenated alkyl is optionally substituted with between 1 and 5 substituents, wherein each substituent has the formula:

wherein each $R^3$ is independently a $C_2$ to $C_{10}$ alkyl or halogenated alkyl;

or a pharmaceutically acceptable salt, solvate, tautomeric form or polymorphic form thereof, and/or bile salt hydrolase (BSH) or active variant thereof with a pharmaceutically acceptable vehicle.

The method of the ninth aspect may further comprise contacting a succinate-degrading enzyme or active variant thereof.

A "subject" may be a vertebrate, mammal, or domestic animal. Hence, compositions and medicaments according to the invention may be used to treat any mammal, for example livestock (e.g. a horse), pets, or may be used in other veterinary applications. Most preferably, however, the subject is a human being.

A "therapeutically effective amount" of the polypeptide or the pharmaceutical composition is any amount which, when administered to a subject, is the amount of the aforementioned that is needed to treat or prevent *C. difficile* infection.

For example, the therapeutically effective amount may be from about 0.001 ng to about 1 mg, and preferably from about 0.01 ng to about 100 ng. It is preferred that the amount of agent is an amount from about 0.1 ng to about 10 ng, and most preferably from about 0.5 ng to about 5 ng.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent may be mixed with a vehicle having the necessary compression properties in suitable proportions and compacted in the shape and size desired. The powders and tablets preferably contain up to 99% of the active agents. Suitable solid vehicles include, for example, calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The active agent according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and *arachis* oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The agent may be prepared as a sterile solid composition that may be dissolved or suspended at the time of administration using sterile water, saline, or other appropriate sterile injectable medium.

The agents and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The agents used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In one embodiment, the pharmaceutically acceptable vehicle may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given.

In a preferred embodiment, the agents and compositions of the invention may be administered directly to the gut.

Levels of the compounds and polypeptides described herein may be indicators for the suitability of any given FMT donor for treating *C. difficile* infection.

Accordingly, in a tenth aspect of the invention there is provided a method of selecting a faecal microbiota transplant (FMT) donor, for FMT in a subject suffering from a *Clostridioides difficile* infection, the method comprising:

(i) analysing, in a sample obtained from a potential FMT donor, the concentration of a short or medium chain fatty acid, bile acids, enzymes associated with the production of a short or medium chain fatty acid, and/or bile salt hydrolase (BSH), or the enzymatic activity thereof, or an expression product thereof; and (ii) comparing this concentration, or enzymatic activity thereof, or expression product thereof, with a reference value from a control population for the concentration of the short or medium chain fatty acid, bile acid, enzymes associated with the production of a short or medium chain fatty acid, and/or bile salt hydrolase (BSH), or the enzymatic activity thereof, or the expression products thereof, wherein an FMT donor is selected as having;

a) a higher concentration of a short or medium chain fatty acid, enzymes associated with the production of a short or medium chain fatty acid and/or BSH, or the enzymatic activities thereof, or the expression products thereof, relative to the respective reference value; and/or b) a lower concentration of bile acids that stimulate *Clostridioides difficile* germination, relative to the respective reference value; and/or c) a higher concentration of bile acids that inhibit *Clostridioides difficile* vegetative growth.

Preferably, the short or medium chain fatty acid is saturated.

Preferably, the short or medium chain fatty acid is selected from the group consisting of: propionate, butyrate, valerate, hexanoate, heptanoate, octanoate and pelargonate.

Preferably the short or medium chain fatty acid and/or BSH levels are analysed and FMT donors are selected with a high concentration of short or medium chain fatty acid e and/or BSH, or the enzymatic activity thereof, or the expression product thereof.

Preferably, the short or medium chain fatty acid is valerate, hexanoate, heptanoate octanoate or pelargonate as defined in the first aspect. Most preferably the short or medium chain fatty acid is valerate, hexanoate or heptanoate as defined in the first aspect.

Preferably, the short or medium chain fatty acid is valerate as defined in the first aspect. Preferably, the short or medium chain fatty acid is hexanoate as defined in the first aspect. Preferably, the short or medium chain fatty acid is heptanoate as defined in the first aspect. Preferably, the short or medium chain fatty acid is octanoate as defined in the first aspect. Preferably, the short or medium chain fatty acid is pelargonate as defined in the first aspect.

Concentrations, enzymatic activities and expression products may be measured by analytical methods known to the skilled person.

The skilled person will be aware that analysis of expression products thereof includes analysis of mRNA amounts, as measured routinely in the art.

Analytical methods may include, for example qPCR, enzymatic activity assays, mass spectroscopy or NMR spectroscopy.

High short or medium chain fatty acid concentrations may relate to values above 1 μg/g of stool, preferably above 10 μg/g of stool and most preferably above 40 μg/g of stool.

In one embodiment the bile acids that stimulate *Clostridioides difficile* germination include cholate and/or taurocholic acid.

Low concentrations of bile acids that stimulate *Clostridioides difficile* germination may relate to cholate values below 1 mg/g faeces, preferably below 0.5 mg/g faeces and most preferably below 0.2 mg/g faeces.

Low concentrations of bile acids that stimulate *Clostridioides difficile* germination may relate to values of taurocholic acid below 0.8 mg/g faeces, preferably below 0.7 mg/g faeces and most preferably below 0.6 mg/g faeces.

In one embodiment the bile acids that inhibit *Clostridioides difficile* vegetative growth are deoxycholate and/or lithocholic acid.

High concentrations of bile acids that inhibit *Clostridioides difficile* vegetative growth may relate to values of deoxycholate above than 0.1 mg/g faeces, preferably above 0.5 mg/g faeces and most preferably above 0.6 mg/g faeces.

High concentration of bile acids that inhibit *Clostridioides difficile* vegetative growth may relate to values of lithocholic acid above than 0.1 mg/g faeces, preferably above 0.2 mg/g faeces and most preferably above 0.3 mg/g faeces.

Preferably, the bile acid is taurocholic acid.

Preferably, the enzymes associated with short or medium chain fatty acid production is as described in the seventh aspect.

Preferably, the enzymes associated with short or medium chain fatty acid production are associated with valerate production, and are selected from a group consisting of: 5-amino-valerate aminotransferase, 5-hydroxyvalerate dehydrogenase and 5-hydroxyvalerate CoA-transferase. 5-hydrodroxyvaleryl-CoA dehydrogenase/dehydratase, 2,4-pentadienoyl-CoA reductase, 3-pentenoyl-CoA $\Delta^3$, $\Delta^2$-isomerase, Enzymes of the oxidation of fatty acids, 5-hydroxyvalerate CoA-transferase, phosphate acetyltransferase and acetate kinase.

Preferably, the BSH is an enzyme that degrades taurocholic acid and can be measured by measuring the rate of removal of taurine from taurodeoxycholic acid per mg of faecal protein per minute. Preferably, high levels of BSH relates to at least 0.1 nmol of deconjugated bile acid (deoxycholic acid) formed per mg of faecal protein per minute, preferably at least 0.5 nmol of deconjugated bile acid (deoxycholic acid) formed per mg of faecal protein per minute, more preferably 1 nmol of deconjugated bile acid (deoxycholic acid) formed per mg of faecal protein per minute and most preferably 1.5 nmol of deconjugated bile acid (deoxycholic acid) formed per mg of faecal protein per minute.

Preferably, the BSH is *Bifidobacterium adolescentis* BSH.

The sample may be any material that is obtainable from a subject from which the above are obtainable. The sample may comprise blood, urine, tissue etc. Preferably, the sample is a faecal sample, for example a faecal swab.

Levels of the above indicators may also be measured in potential FMT recipients, suffering from *C. difficile* infection, to identify subjects that are suitable FMT recipients.

Accordingly, in an eleventh aspect of the invention there is provided a method of selecting a faecal microbiota transplant (FMT) recipient, wherein the recipient suffers from *Clostridioides difficile* infection, the method comprising:
i) analysing, in a sample obtained from a potential FMT recipient, the concentration of a short or medium chain fatty acid, bile acid, enzymes associated with the production of a short or medium chain fatty acid, and/or bile salt hydrolase (BSH), or the enzymatic activity thereof, or an expression product thereof; and
ii) comparing this concentration, or enzymatic activity thereof, or expression product thereof, with a reference value from a control population for the concentration of a short or medium chain fatty acid, bile acid, enzymes associated with the production of a short or medium chain fatty acid, and/or bile salt hydrolase (BSH) or the enzymatic activity thereof, or the expression product thereof, wherein an FMT recipient is selected as having;
a) a lower concentration of a short or medium chain fatty acid, enzymes associated with the production of a short or medium chain fatty acid and/or BSH, or the enzymatic activities thereof, or the expression products thereof, relative to the respective reference value; and/or
b) a higher concentration of bile acids that stimulate *Clostridioides difficile* germination, relative to the respective reference value; and/or
c) a lower concentration of bile acids that inhibit *Clostridioides difficile* vegetative growth.

Preferably, short or medium chain fatty acid and/or BSH levels are analysed and FMT donors are selected with a low concentration of a short or medium chain fatty acid and/or BSH, or the enzymatic activity thereof, or the expression products thereof Preferably, the short or medium chain fatty acid is as defined in the tenth aspect.

Analytical methods may be those as defined the tenth aspect of the invention.

Low short or medium chain fatty acid levels may relate to amounts below 100 μg/g of stool, preferably below 50 μg/g of stool, more preferably below 25 μg/g of stool and most preferably below 20 μg/g of stool.

In one embodiment the bile acids that stimulate *Clostridioides difficile* germination include cholate and/or taurocholic acid.

High concentrations of bile acids that stimulate *Clostridioides difficile* germination may relate to cholate values above 0.2 mg/g faeces, preferably above 0.5 mg/g faeces and most preferably above 1 mg/g faeces.

High concentrations of bile acids that stimulate *Clostridioides difficile* germination may relate to values of taurocholic acid above 0.8 mg/g faeces, preferably above 0.9 mg/g faeces and most preferably above 1 mg/g faeces.

In one embodiment the bile acids that inhibit *Clostridioides difficile* vegetative growth are deoxycholate and/or lithocholic acid.

Low concentrations of bile acids that inhibit *Clostridioides difficile* vegetative growth may relate to values of deoxycholate below 0.6 mg/g faeces, preferably below 0.5 mg/g faeces and most preferably below 0.1 mg/g faeces.

Low concentrations of bile acids that inhibit *Clostridioides difficile* vegetative growth may relate to values of lithocholic acid below 0.3 mg/g faeces, preferably below 0.2 mg/g faeces and most preferably below 0.1 mg/g faeces.

Preferably, the bile acid is taurocholic acid.

Preferably, the enzymes associated with short or medium chain fatty acid production are as described in the tenth aspect.

Preferably, the BSH is *Bifidobacterium adolescentis* BSH.

Preferably, the BSH is an enzyme that degrades taurocholic acid and can be measured by measuring the rate of removal of taurine from taurodeoxycholic acid per mg of faecal protein per minute. Preferably, low levels of BSH relates to less than 10 nmol of deconjugated bile acid (deoxycholic acid) formed per mg of faecal protein per minute, preferably less than 5 nmol of deconjugated bile acid (deoxycholic acid) formed per mg of faecal protein per minute, more preferably less than 1 nmol of deconjugated bile acid (deoxycholic acid) formed per mg of faecal protein per minute and most preferably less than 0.5 nmol of deconjugated bile acid (deoxycholic acid) formed per mg of faecal protein per minute.

The sample may be as defined in the tenth aspect of the invention.

Advantageously, FMT donors and recipients may be matched to improve the outcomes of FMT, by matching donors according to the tenth aspect of the invention with FMT recipients according to the eleventh aspect of the invention.

In another aspect, there is provided a compound of formula (I):

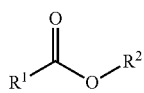

(I)

wherein $R^1$ is a $C_4$ alkyl or halogenated alkyl; and
$R^2$ is hydrogen or a $C_1$ to $C_4$ alkyl or halogenated alkyl;
or a pharmaceutically acceptable salt, solvate, tautomeric form or polymorphic form thereof, for use in treating, preventing or ameliorating a *Clostridioides difficile* infection.

In another aspect, there is provided: (i) a bile salt hydrolase (BSH) or an active variant thereof, and (ii) a compound of formula (I):

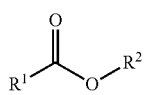

(I)

wherein $R^1$ is a $C_4$ alkyl or halogenated alkyl; and
$R^2$ is hydrogen or a $C_1$ to $C_4$ alkyl or halogenated alkyl;
or a pharmaceutically acceptable salt, solvate, tautomeric form or polymorphic form thereof, for use in treating, preventing or ameliorating a *Clostridioides difficile* infection.

In another aspect, there is provided: (i) a succinate-metabolising enzyme or an active variant thereof; and (ii) a bile salt hydrolase (BSH) or an active variant thereof; and/or (iii) a compound of formula (I):

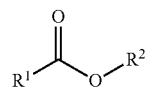

(I)

wherein $R^1$ is a $C_4$ alkyl or halogenated alkyl; and
$R^2$ is hydrogen or a $C_1$ to $C_4$ alkyl or halogenated alkyl;
or a pharmaceutically acceptable salt, solvate, tautomeric form or polymorphic form thereof,
for use in treating, preventing or ameliorating a *Clostridioides difficile* infection.

In another aspect, there is provided a microorganism capable of converting valerate precursors, present in the gut, to valerate, for use in the prevention, treatment or amelioration of a *Clostridioides difficile* infection.

In another aspect, there is provided a *C. difficile* treatment pharmaceutical composition comprising the compound of formula (I):

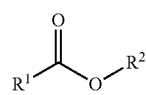

(I)

wherein $R^1$ is a $C_4$ alkyl or halogenated alkyl; and
$R^2$ is hydrogen or a $C_1$ to $C_4$ alkyl or halogenated alkyl;
or a pharmaceutically acceptable salt, solvate, tautomeric form or polymorphic form thereof and/or bile salt hydrolase (BSH) or an active variant thereof, and a pharmaceutically acceptable vehicle.

In another aspect, there is provided a method of preparing the *C. difficile* treatment pharmaceutical composition according to the previous aspect, the method comprising contacting a compound of formula (I):

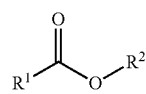

(I)

wherein $R^1$ is a $C_4$ alkyl or halogenated alkyl; and
$R^2$ is hydrogen or a $C_1$ to $C_4$ alkyl or halogenated alkyl;
or a pharmaceutically acceptable salt, solvate, tautomeric form or polymorphic form thereof, and/or bile salt hydrolase (BSH) or active variant thereof with a pharmaceutically acceptable vehicle.

In another aspect, there is provided a method of selecting a faecal microbiota transplant (FMT) donor, for FMT in a subject suffering from a *Clostridioides difficile* infection, the method comprising:
(i) analysing, in a sample obtained from a potential FMT donor, the concentration of valerate, bile acids, enzymes associated with valerate production, and/or bile salt hydrolase (BSH), or the enzymatic activity thereof, or an expression product thereof; and
(ii) comparing this concentration, or enzymatic activity thereof, or expression product thereof, with a reference value from a control population for the concentration of valerate, bile acid, enzymes associated with valerate production, and/or bile salt hydrolase (BSH), or the enzymatic activity thereof, or the expression products thereof, wherein an FMT donor is selected as having;

a) a higher concentration of valerate, enzymes associated with valerate production and/or BSH, or the enzymatic activities thereof, or the expression products thereof, relative to the respective reference value; and/or b) a lower concentration of bile acids that stimulate *Clostridioides difficile* germination, relative to the respective reference value; and/or c) a higher concentration of bile acids that inhibit *Clostridioides difficile* vegetative growth.

d)

In another aspect, there is provided a method of selecting a faecal microbiota transplant (FMT) recipient, wherein the recipient suffers from *Clostridioides difficile* infection, the method comprising:

i) analysing, in a sample obtained from a potential FMT recipient, the concentration of valerate, bile acid, enzymes associated with valerate production, and/or bile salt hydrolase (BSH), or the enzymatic activity thereof, or an expression product thereof; and ii) comparing this concentration, or enzymatic activity thereof, or expression product thereof, with a reference value from a control population for the concentration of valerate, bile acid, enzymes associated with valerate production, and/or bile salt hydrolase (BSH) or the enzymatic activity thereof, or the expression product thereof, wherein an FMT recipient is selected as having;

a) a lower concentration of valerate, enzymes associated with valerate production and/or BSH, or the enzymatic activities thereof, or the expression products thereof, relative to the respective reference value; and/or b) a higher concentration of bile acids that stimulate *Clostridioides difficile* germination, relative to the respective reference value; and/or c) a lower concentration of bile acids that inhibit *Clostridioides difficile* vegetative growth.

It will be appreciated that the invention extends to any nucleic acid or peptide or variant, derivative or analogue thereof, which comprises substantially the amino acid or nucleic acid sequences of any of the sequences referred to herein, including variants or fragments thereof. The terms "substantially the amino acid/nucleotide/peptide sequence", "variant" and "fragment", can be a sequence that has at least 40% sequence identity with the amino acid/nucleotide/peptide sequences of any one of the sequences referred to herein, for example 40% identity with the sequence identified as SEQ ID Nos:1-19

Amino acid/polynucleotide/polypeptide sequences with a sequence identity which is greater than 65%, more preferably greater than 70%, even more preferably greater than 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (v) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=-1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps and either including or excluding overhangs. Preferably, overhangs are included in the calculation. Hence, a most preferred method for calculating percentage identity between two sequences comprises (i) preparing a sequence alignment using the ClustalW program using a suitable set of parameters, for example, as set out above; and (ii) inserting the values of N and T into the following formula: Sequence Identity=(N/T)*100.

Alternative methods for identifying similar sequences will be known to those skilled in the art. For example, a substantially similar nucleotide sequence will be encoded by a sequence which hybridizes to DNA sequences or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in, for example, SEQ ID Nos:1 to 19.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

FIG. 1: shows average *C. difficile* plate counts taken from VA (saline-treated cultures, black dashed line) and VB (FMT-treated cultures, black solid line) over the course of the experiment. (a) Average *C. difficile* total viable counts. (b) Average *C. difficile* spore plate counts. The grey shaded box indicates the clindamycin-dosing period, while the vertical dotted line indicates the day of FMT or saline dosing. Error bars represent the mean standard deviation (*, $p<0.05$ by SANTA analysis).

FIG. 2: shows stream plots showing the OTU abundances in each chemostat culture over time. Each stream of colour represents an OTU, and streams are grouped by phylum: *Bacteroidetes* (blue), *Firmicutes* (green), *Proteobacteria* (orange), *Verrucomicrobia* (purple), unclassified (grey), and *C. difficile* (red). The width of the stream represents the OTU abundance at each time point. The dotted box indicates the clindamycin-dosing period, while the dotted vertical line indicates the day of FMT or saline dosing.

FIG. 3: shows $^1$H-NMR metabolites that changed following clindamycin treatment and with FMT (VA=saline-treated cultures, dashed line; VB=FMT-treated cultures, solid line). (a) valerate, (b) 5-aminovalerate, (c) ethanol, (d) succinate, (e) propionate, and (f) methanol. The shaded grey box indicates the clindamycin-dosing time period, while the vertical dotted line indicates the day of FMT or saline dosing. SANTA analysis with Benjamini-Hochberg FDR was used to compare the following: steady state cultures to clindamycin-treated cultures, steady state cultures to post-clindamycin cultures, and FMT-treated cultures to saline treated cultures.

FIG. 4: shows bile acids that changed following clindamycin treatment and correlated with *C. difficile* TVC (VA=saline-treated cultures, dashed line; VB=FMT-treated cultures, solid line). (a) taurocholic acid (TCA), (b) cholic acid (CA), (c) deoxycholic acid (DCA), and (d) lithocholic acid (LCA). The shaded grey box indicates the clindamycin-dosing period, while the vertical dotted line indicates the day of FMT or saline dosing. Steady state cultures were compared to clindamycin-treated cultures using SANTA analysis with Benjamini-Hochberg FDR.

FIG. 5: shows the effect of FMT on the concentration of valerate in stool from healthy FMT donors (n=5) and recurrent CDI patients pre-FMT (n=16) and at several time points post-FMT (n=16). Mann-Whitney U test for donors vs. pre-FMT, Friedman test for pre-FMT vs. post-FMT.  $p<0.01$, * $p<0.001$.

FIG. 6: shows that valerate inhibits *C. difficile* vegetative growth in batch cultures. Vegetative cells were inoculated into sBHI broth containing varying concentrations of valerate (o, 1, 2, 3, 4, 5, 10, and 20 mM) and $OD_{600}$ measurements were taken at 0, 2, 4, 6, and 8 hours. The change in $OD_{600}$ (from a time point during the exponential phase) was plotted against the concentrations of valerate tested. (a) *C. difficile* ribotype 010, (b) *C. difficile* ribotype 012, (c) *C. difficile* ribotype 027, (d) *Bacteroides uniformis*, (e) *Bacteroides vulgatus*, (f) *Clostridium scindens*. Error bars represent the mean standard deviation, * $p<0.05$,  $p<0.01$, * $p<0.001$.

FIG. 7: shows the diversity of bacterial communities cultured in chemostat vessels (VA=saline-treated cultures, dashed line; VB=FMT-treated cultures, solid line). (a) Shannon diversity index (H'), (b) Richness ($S_{obs}$), (c) Pielou's evenness index (J'). The shaded grey box indicates the clindamycin-dosing period, while the vertical dotted line indicates the day of FMT or saline dosing. SANTA analysis with Benjamini-Hochberg FDR was used to compare the following: steady state cultures to clindamycin-treated cultures, steady state cultures to post-clindamycin cultures, and FMT-treated cultures to saline treated cultures.

FIG. 8: shows $^1$H-NMR metabolites that changed following clindamycin treatment and with FMT (VA=saline-treated cultures, dashed line; VB=FMT-treated cultures, solid line). (a) butyrate, (b) acetate, (c) isobutyrate, and (d) isovalerate. The shaded grey box indicates the clindamycin-dosing time period, while the vertical dotted line indicates the day of FMT or saline dosing. SANTA analysis with Benjamini-Hochberg FDR was used to compare the following: steady state cultures to clindamycin-treated cultures, steady state cultures to post-clindamycin cultures, and FMT-treated cultures to saline treated cultures.

FIG. 9: shows regularized CCA (rCCA) model correlating 16S rRNA gene sequencing data (genus-level) and $^1$H-NMR metabolite data. (a) The representation of units (a.k.a. samples) for the first two canonical variates showing the correlations between variables before (grey), during (blue), and after (orange) the clindamycin-dosing period. "A" represents samples collected from VA and "B" represents samples from VB. (b) Correlation circle plot showing strong correlations between variables before, during, and after the clindamycin-dosing period. Metabolites are shown in blue and bacterial genera are shown in orange. *Clostridium* cluster XI (the clostridial cluster that includes *C. difficile*) is shown in a black box. (c) The representation of units (a.k.a. samples) for the first two canonical variates showing the correlations between variables following FMT (blue) or saline (orange) treatment. "A" represents samples collected from VA (saline-treated cultures) and "B" represents samples from VB (FMT-treated cultures). (d) Correlation circle plot showing strong correlations between variables following FMT or saline treatment. Metabolites are shown in blue and bacterial genera are shown in orange. *Clostridium* cluster XI (the clostridial cluster that includes *C. difficile*) is shown in a black box.

FIG. 10: shows 1D $^1$H-NMR to confirm the identity of valerate in chemostat culture supernatants. (a) 1D $^1$H-NMR spectrum of valerate standard (blue). (b) Overlay of 1D $^1$H-NMR spectrum of valerate standard (blue) with sample spectrum (red). Each peak of the valerate standard is visible in the sample spectrum. (c) Overlay of 1D $^1$H-NMR spectra of sample before (blue) and after (red) valerate spike-in. All the peaks proposed to belong to valerate increased following spike in with valerate standard (green).

FIG. 11: shows 2D 1H-NMR to confirm the identity of valerate in chemostat culture supernatants. (a) Overlay of the $^1$H-$^1$H COSY spectrum of valerate standard (blue) with sample spectrum (red). Each peak of the valerate standard is visible in the sample spectrum. (b) Overlay of the $^1$H-$^1$H TOCSY spectrum of valerate standard (blue) with sample spectrum (red). Again, each peak of the valerate standard is visible in the sample spectrum.

FIG. 12: shows overlay of 1H-$^1$H COSY sample spectrum (blue) and 1H-$^1$H TOCSY sample spectrum (red) to confirm the identity of other metabolites found in chemostat culture supernatants.

FIG. 13: shows statistical total correlation spectroscopy (STOCSY). (a) 5-aminovalerate STOCSY spectrum obtained by correlating all points in the spectra with the 5-aminovalerate resonance at 3.019 ppm. Peak clusters with high correlations (*) correspond to positions where the inventors expected to see peaks for 5-aminovalerate. (b) Succinate STOCSY spectrum obtained by correlating all points in the spectra with the succinate resonance at 2.408 ppm. No other peaks had high correlations with the peak at 2.408, confirming this peak belonged to succinate.

FIG. 14: shows bile acids that changed following clindamycin treatment (VA=saline-treated cultures, dashed line; VB=FMT-treated cultures, solid line). (a) taurodeoxycholic acid (TDCA), (b) glycocholic acid (GCA), (c) glycodeoxycholic acid (GDCA), (d) glycochenodeoxycholic acid (GCDCA), (e) chenodeoxycholic acid (CDCA), and (f) ursodeoxycholic acid (UDCA). The shaded grey box indicates the clindamycin-dosing period, while the vertical dotted line indicates the day of FMT or saline dosing. Steady state cultures were compared to clindamycin-treated cultures using SANTA analysis with Benjamini-Hochberg FDR.

FIG. 15: shows regularized CCA (rCCA) model correlating 16S rRNA gene sequencing data (genus-level) and bile acid data. (a) The representation of units (a.k.a. samples) for the first two canonical variates showing the correlations between variables before (grey), during (blue), and after (orange) the clindamycin-dosing period. "A" represents samples collected from VA and "B" represents samples from VB. (b) Correlation circle plot showing strong correlations between variables before, during, and after the clindamycin-dosing period. Bile acids are shown in blue and bacterial genera are shown in orange. *Clostridium* cluster XI (the clostridial cluster that includes *C. difficile*) is shown in a black box.

FIG. 16: shows TCA is required for *C. difficile* spore germination, but has no effect on *C. difficile* vegetative growth. (a) *C. difficile* spores were incubated sBHI broth in the presence and absence of 1% TCA and grown overnight. There was a significant increase in *C. difficile* germination in the presence of TCA (*** p<0.001). (b) *C. difficile* vegetative cells were inoculated into sBHI broth in the presence and absence of 1% TCA. There were no significant differences in the growth of *C. difficile* in the presence or absence of TCA at any time point in the growth curve. Growth of *C. difficile* in the broths was quantified by taking $OD_{600}$ measurements using a plate spectrometer. Error bars represent the mean standard deviation.

FIG. 17: shows the effect of FMT for rCDI upon microbial community composition. A: Shannon diversity index for faecal samples (**, p<0.0001, Mann-Whitney test for donor vs pre-FMT, Wilcoxon rank sum test for pre-FMT vs post-FMT); B: Richness (Sobs, total number of bacterial taxa observed) (**, p<0.0001); C: Non-metric multidimensional scaling (NMDS) plot at family-level (p<0.001 across all three groups, PERMANOVA).

FIG. 18: shows the effect of FMT for rCDI upon stool bile acid profiles. Assessed via multivariate analysis of UPLC-MS bile acid profiling data. A: PCA scores plot; B: OPLS-DA scores plot, comparing donor and pre-FMT samples; C: OPLS-DA scores plot, comparing pre-FMT and post-FMT samples; D: OPLS-DA S-plot of pre- vs post-FMT data. QC: quality controls. CA: cholic acid; CDCA: chenodeoxycholic acid; DCA: deoxycholic acid; GCA: glycocholic acid; GCDCA: glycochenodeoxycholic acid; LCA: lithocholic acid; TCA: taurocholic acid; TCDCA: taurochenodeoxycholic acid; TDCA: taurodeoxycholic acid.

FIG. 19: shows a regularised CCA (rCCA) model correlating 16S rRNA gene sequencing data (family level) and bile acid data. A: Unit representation plot for the two canonical variables (metataxonomics and stool bile acids); B: Correlation circle plot demonstrating strong correlations (r>0.5) between variables for donors, pre-FMT and post-FMT samples. Bile acids are shown in blue and bacterial families are shown in orange. Blue asterisks: overlap in labels for taurocholic acid (TCA) and taurodeoxycholic acid (TDCA). GCA: glycocholic acid; GCDCA: glycochenodeoxycholic acid; CA: cholic acid; DCA: deoxycholic acid; LCA: lithocholic acid.

FIG. 20: shows the effect of FMT upon gene copy number and BSH enzyme activity. A) bsh group 1A; B) bsh group 1B; C) bsh group 3C; D) baiCD operon of 7-α-dehydroxylase; E) BSH enzyme activity within faecal supernatant (*, p<0.05; , p<0.01; *; p<0.001; ****, p<0.0001; Mann-Whitney U for donors vs pre-FMT, Wilcoxon rank sum test for pre-FMT vs post-FMT).

FIG. 21: shows *Clostridium difficile* batch cultures. Changes in spectrophotometer reading (ΔOD600) after overnight incubation of *C. difficile* spores (three ribotypes assayed: 010, 012, 027) in sBHI+/−TCA in which bacterial species of interest had been cultured for 24 hours. *C. difficile* spores in sBHI supplemented with 1% TCA ('No supernatant, 1% TCA') was used as positive control in all cases; statistical testing shown was performed relative to this sample for the particular ribotype under assessment. A) Batch cultures of native *E. coli*, and two forms of *E. coli* into which bsh genes had been cloned (*E. coli* BSHlow=*E. coli* expressing BSH with low deconjugation ability; *E. coli* BSHhigh=*E. coli* expressing BSH with high deconjugation activity). B) Batch cultures of BSH-producing microbial species found to be affected by FMT in metataxonomic analysis, and vegetative *C. difficile*. C) Batch cultures of *C. scindens*+/−BSH-expressing *E. coli* (, p<0.01; **, p<0.0001; ANOVA with multiple group comparisons, Benjamini-Hochberg correction).

FIG. 22: shows a schematic of gut microbiota-bile acid interactions in humans. Taurine and glycine conjugates of the primary bile acids cholate and chenodeoxycholate are formed in the liver, and secreted through the biliary system into the small intestine. Once there, the microbially-derived enzyme bile salt hydrolase (BSH) acts to remove these taurine and glycine conjugates, reforming unconjugated cholate and chenodeoxycholate. From here, the complex, multi-step process of 7-α-dehydroxylation also occurs through microbially derived enzymes, and converts primary to secondary bile acids (specifically, cholate is converted to deoxycholate, and chenodeoxycholate is converted to lithocholate. A range of other microbially-derived enzymes are also able to perform biotransformations upon primary bile acids [1]. Taurocholate (TCA) is the major endogenous trigger to *C. difficile* germination (with glycine as co-germinant) [2]. Cholate and deoxycholate (at high concentrations) also trigger *C. difficile* germination [2]. However (*), deoxycholate (and lithocholate) at physiological concentrations can inhibit TCA-mediated *C. difficile* germination [3,4]. Deoxycholate, lithocholate and other secondary bile acids can inhibit *C. difficile*'s vegetative growth and toxin activity [2,3,4]. Chenodeoxycholate also inhibit's *C. difficile*'s germination [5]. A direct link between microbiota, bile acids and FXR signalling has been demonstrated in rodents through the use of germ-free or antibiotic-treated animals [1], but the interplay between these factors in humans remains unclear. [1] Wahlstrom A, Sayin S I, Marschall H U, Backhed, F. Intestinal crosstalk between bile acids and microbiota and its impact on host metabolism. Cell Metab (2016); 24(1):41-50. [2] Sorg J A, Sonenshein A L. Bile salts and glycine as cogerminants for *Clostridium difficile* spores. J Bacteriol (2008); 190(7):2505-2512. [3] Thanissery R, Winston JA, Theriot C M. Inhibition of spore germination, growth, and toxin activity of clinically relevant *C. difficile* strains by gut microbiota derived secondary bile acids. Anaerobe (2017); 45:86-100. [4] Therior C M, Bowman A A, Young V B. Antibiotic-induced alterations of the gut microbiota alter secondary bile acid production and allow for *Clostridium difficile* spore germination and outgrowth in the large intestine. mSphere (2016); 1(1). Pii: e00045-15. [5] Sorg J A, Sonenshein A L. Chenodeoxycholate is an inhibitor of *Clostridium difficile* spore germination. J Bacteriol (2009); 191(3):1115-1117.

FIG. 23: shows the evolutionary relationships of BSH genes with their taxonomic hosts shown. The evolutionary history was inferred using the Neighbor-Joining method [1]. The optimal tree with the sum of branch length=11.24114695 is shown. The tree is drawn to scale, with branch lengths in the same units as those of the evolutionary distances used to infer the phylogenetic tree. The evolutionary distances were computed using the Poisson correction method [2] and are in the units of the number of amino acid substitutions per site. The analysis involved 102 amino acid sequences. All positions containing gaps and missing data were eliminated. There were a total of 145 positions in the final dataset. Evolutionary analyses were conducted in MEGA7 [3]. [1] Zuckerkandl E. and Pauling L. (1965). Evolutionary divergence and convergence in proteins. Edited in Saitou N. and Nei M. (1987). The neighbor-joining method: A new method for reconstructing phylogenetic trees. Molecular Biology and Evolution 4:406-425. [2] Evolving Genes and Proteins by V. Bryson and H. J. Vogel, pp. 97-166. Academic Press, New York. [3] Kumar S., Stecher G., and Tamura K. (2016). MEGA7: Molecular Evolutionary Genetics Analysis version 7.0 for bigger datasets. Molecular Biology and Evolution 33:1870-1874.

FIG. 24: shows an NMDS plot showing different routes of FMT administration (colonoscopy vs capsule administration) for pre- and post-FMT samples. There were no significant differences between patients treated via capsule or colonoscopy pre-FMT (p=0.288, PERMANOVA), or post-FMT (p=0.288, PERMANOVA).

FIG. 25: shows 16S rRNA gene copy numbers. No significant differences were found in bacterial load between groups (p>0.05 for all comparisons).

FIG. 26: shows the differences in 16S rRNA gene sequencing data in rCDI patients compared to donor or post-FMT. Extended error bar plots, with OTUs changing significantly measured by White's non-parametric test with Benjamini-Hochberg correction, using threshold of differences between mean proportions>1%. A) Donor vs pre-FMT; B) Pre-FMT vs post-FMT. Asterisks indicate OTUs changed in both comparisons.

FIG. 27: shows OPLS-DA S-plot of donor vs pre-FMT data. As assessed via multivariate analysis of UPLC-MS bile acid profiling data. CA: cholic acid; CDCA: chenodeoxycholic acid; DCA: deoxycholic acid; GCA: glycocholic acid; GCDCA: glycochenodeoxycholic acid; LCA: lithocholic acid; TCA: taurocholic acid; TCDCA: taurochenodeoxycholic acid; TDCA: taurodeoxycholic acid.

FIG. 28: shows univariate analysis of the effect of FMT upon profiles of specific bile acids as assessed using UPLC-MS bile acid profiling data. A: Taurocholic acid; B: Glycocholic acid; C: Chenodeoxycholic acid; D: Cholic acid; E: Taurochenodeoxycholic acid; F: Glycochenodeoxycholic acid; G: Lithocholic acid; H: Deoxycholic acid (*, $p<0.05$; , $p<0.01$; *, $p<0.001$; ****, $p<0.0001$; Mann-Whitney U for donor vs pre- or post-FMT, Wilcoxon rank sum testing for pre- vs post-FMT).

FIG. 29: shows bile acid changes after *C. difficile* batch culture experiments, as established via UPLC-MS of media from the end of batch culture experiments. A) Taurocholic acid: cholic acid (TCA: CA) ratios at the end of batch culture experiments; high ratios are consistent with low/absent BSH activity, and low ratios are consistent with high BSH activity. *C. difficile* spores in sBHI supplemented with 1% TCA ('No supernatant, 1% TCA') was used as positive control in all cases. B) Relative intensities for cholic acid and deoxycholic acid (DCA) at the end of batch culture experiments (data shown for batch cultures in which inhibition of *C. difficile* germination occurred). Statistical testing shown was performed in all cases relative to 'No supernatant, 1% TCA' (, $p<0.01$; *, $p<0.001$; ****, $p<0.0001$, student t-test).

FIG. 30: shows a summary of a valerate production pathway, as described in Buckel W. Unusual enzymes involved in five pathways of glutamate fermentation. Appl Microbiol Appl Microbiol Biotechnol 2001; 57:263-273.

EXAMPLES

Materials and Methods

Figure 1:
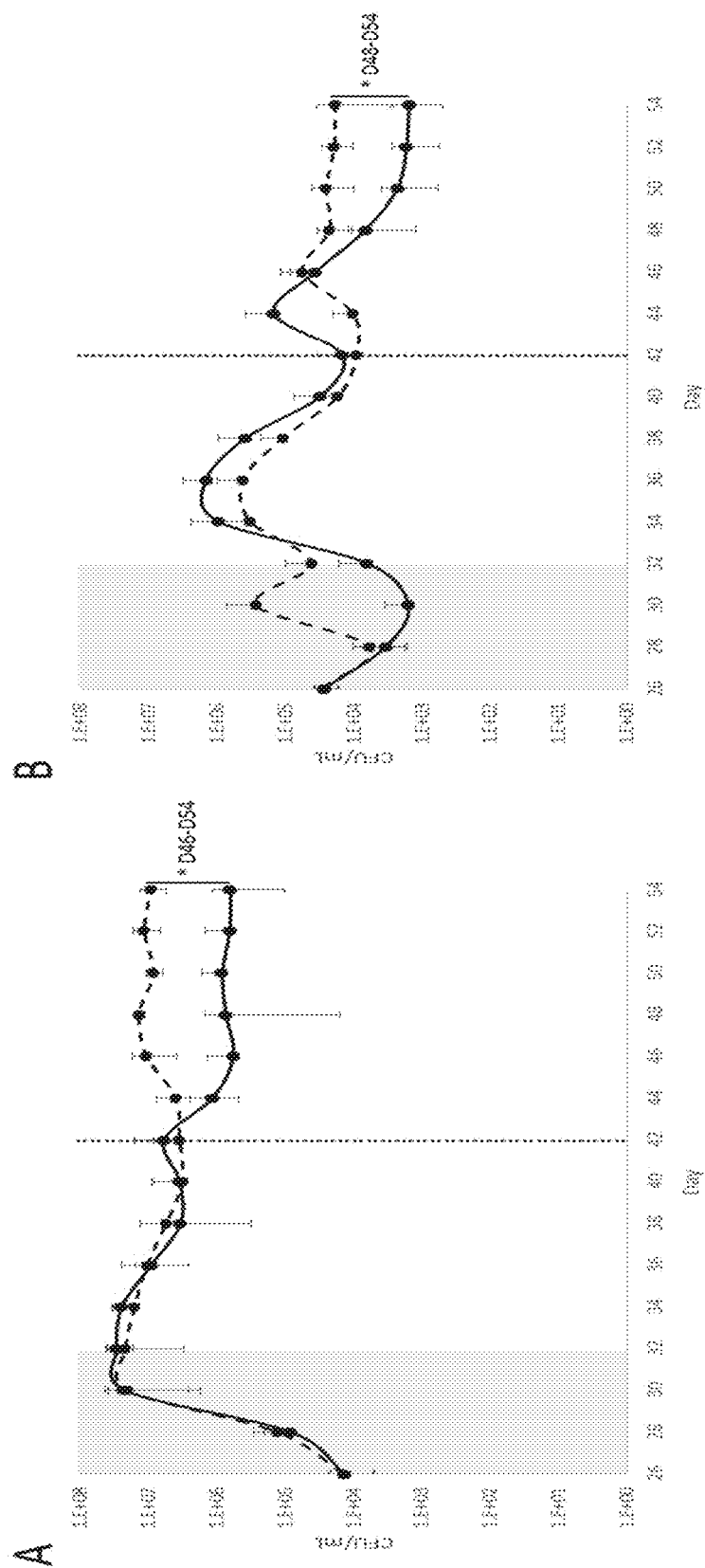

Chemostat Model of CDI:

The chemostat models used in this study were two identical Electrolab FerMac 200 series bioreactor systems (Electrolab, Tewkesbury, UK). Chemostat inoculum and growth medium were prepared and vessels were inoculated and operated as previously described.[14] Stool samples were collected under approval from the UK National Research Ethics Centres (13/LO/1867). The inventors performed three separate twin-vessel chemostat experiments. In each experiment, two identical vessels ("VA" receiving saline vehicle control and "VB" receiving FMT preparation) were inoculated with a 10% (w/v) faecal slurry prepared using fresh faeces from a healthy donor not exposed to antibiotics within the previous 2 months (Run 1=male in his 40's; Run 2=male in his 60's; Run 3=male in his 80's). The inventors used clindamycin and *C. difficile* spores to induce CDI in their chemostat model following a modified version of the methods previously described by Freeman and colleagues (see Table 2)

$^1$H-Nmr Spectroscopy:

Chemostat culture supernatants were prepared for $^1$H-NMR. One-dimensional $^1$H-NMR spectra were acquired from chemostat culture supernatants at 300 K on a Bruker DRX 600 MHz NMR spectrometer or a Bruker AVANCE III 600 MHz NMR spectrometer (Bruker Biospin, Germany). A standard one-dimensional NMR pulse sequence [RD-90°-t1-90°-tm-90°-acq] was used with a recycle delay (4 s) and mixing time (100 ms). The 900 pulse length was around 10 µs and 32 scans were recorded. Metabolites concentrations were quantified from spectra using the Chenomx NMR suite software (Chenomx Inc, Edmonton, Canada).[25]

To confirm the identity of key metabolites in chemostat culture supernatants a series of NMR spectra including 1D $^1$H NOESY, 2D $^1$H-1H TOCSY and $^1$H-1H COSY of a chemostat culture supernatant and a metabolite standard were recorded.

Ultra Performance Liquid Chromatography-Mass Spectrometry (UPLC-MS) Bile Acid

Profiling: Bile acids were extracted from 50 µL of chemostat culture by adding 150 µL of cold methanol, followed by incubation at −30° C. for 2 hours. Tubes were centrifuged at 9500×g and 4° C. for 20 min and 120 µL of supernatant was loaded into vials. Bile acid analysis was performed

TABLE 2

Time periods used for CDI chemostat experiments to compare the effects of FMT to saline.

| Vessel | Days 0-17 | Days 18-24 | Day 24 | Days 25-31 | Days 32-42 | Day 42 | Days 43-54 |
|---|---|---|---|---|---|---|---|
| Control vessel (VA) | Stabilisation period (no intervention) | Stable communities (no intervention) | Added *C. difficile* spores | Added *C. difficile* spores (day 25) and clindamycin every 12 hrs (days 25-31) | Stabilisation period (no intervention) | Added saline | No intervention |
| Test vessel (VB) | Stabilisation period (no intervention) | Stable communities (no intervention) | Added *C. difficile* spores | Added *C. difficile* spores (day 25) and clindamycin every 12 hrs (days 25-31) | Stabilisation period (no intervention) | Added FMT | No intervention |

After stopping clindamycin dosing, microbial communities were allowed to stabilise before administering the FMT preparation or saline vehicle control. FMT mixtures were prepared using fresh faecal samples provided by donors enrolled within Imperial's FMT Programme.[23] Stool samples from these faecal donors have previously been used to successfully treat recurrent CDI patients.

16S rRNA Gene Sequencing:

Sample libraries amplifying the V3-V4 region of the 16S gene were prepared following Illumina's 16S Metagenomic Sequencing Library Preparation Protocol,[24] with a few modifications. First, the inventors used the SequalPrep Normalization Plate Kit (Life Technologies, Carlsbad, USA) to clean up and normalise the index PCR reactions. Also, the inventors used the NEB Next Library Quant Kit for Illumina (New England Biolabs, Ipswich, USA) to quantify the sample libraries. Sequencing was performed on an Illumina MiSeq platform (Illumina Inc, San Diego, USA) using the MiSeq Reagent Kit v3 (Illumina) and paired-end 300 bn chemistry.

using an ACQUITY UPLC (Waters Ltd, Elstree, UK) coupled to a Xevo G2 Q-ToF mass spectrometer. The MS system was equipped with an electrospray ionization source operating in negative ion mode, using methods previously described by Sarafian and colleagues.[26].

Human Stool Samples for SCFA Analysis:

Human stool samples were collected from recurrent CDI patients (n=16) and healthy donors (n=5) as part of a randomised clinical trial comparing the efficacy of capsulised and colonoscopic FMT for the treatment of recurrent CDI, as previously described.[27] Pre-FMT samples were collected from recurrent CDI patients while on suppressive vancomycin. Post-FMT samples were collected 1, 4, and 12 weeks after FMT treatment. All patients were successfully treated following a single FMT.

Gas Chromatography-Mass Spectrometry (GC-MS):

A targeted GC-MS protocol was used to identify and quantify SCFAs from human stool samples as previously-described.[21] Samples were analysed on an Agilent 7890B GC system, coupled to an Agilent 5977A mass selective detector (Agilent, Santa Clara, CA). Data analysis was performed using MassHunter software (Agilent).

*C. difficile* Batch Cultures:

The inventors tested the effects of valerate (Fisher Scientific) on the vegetative growth of three *C. difficile* ribotypes (010, 012, and 027) as well as several gut commensal bacteria (*Bacteroides uniformis*, *Bacteroides vulgatus*, and *Clostridium scindens*). The inventors centrifuged an overnight culture of the test isolate at 3000×g for 10 minutes and resuspended the cells in sBHI (supplemented Brain Heart Infusion broth (Sigma-Aldrich), with 5 mg/mL yeast extract (Sigma-Aldrich), and 0.1% L-cysteine (Sigma-Aldrich)) containing varying concentrations of valerate (o, 1, 2, 3, 4, 5, 10, and 20 mM, pH of broth adjusted to 6.8) in triplicate. The OD600 was measured at time zero and cultures were incubated at 37° C. in an ElectroTek AW 400TG Anaerobic Workstation (ElectroTek, West Yorkshire, UK). Additional $OD_{600}$ measurements were taken at 2, 4, 6, and 8 hours post-inoculation. The inventors plotted the changes in $OD_{600}$ (from a time point during the exponential phase) against each concentration of valerate tested. The inventors used ANOVA and Tukey post hoc test to determine whether the concentration of valerate tested affected the growth of the test isolate compared to batch cultures grown in the absence of valerate.

They also tested the effects of taurocholic acid (TCA) on *C. difficile* germination and vegetative growth using batch cultures.

Statistical Analysis and Data Integration:

Basic statistical tests were performed using IBM SPSS Statistics Software version 23 (paired t-test, ANOVA) or GraphPad Prism version 7.03 (Mann-Whitney U test, Friedman test). Short AsyNchronous Time-series Analysis (SANTA) was used to determine whether there were significant changes in data trajectories at several time periods over the course of the chemostat experiments.[29] Spearman's rho statistic and p-values were calculated for *C. difficile* TVC and metabolite data using the cor and cor.test functions, respectively, within the stats base library within R. A p-value less than 0.05 was considered significant. The inventors used regularised Canonical Correlation Analysis (rCCA) to correlate metataxonomic and metabolomic data using the mixOmics library within R)[30].

Bacterial Strains:

*C. difficile* DS1684 (ribotype 010, non-toxigenic strain) was used for chemostat model experiments. *C. difficile* DS1684, *C. difficile* CD630 (ribotype 012, virulent multi-drug resistant strain), *C. difficile* R20291 (ribotype 027, a hypervirulent strain), *Bacteroides uniformis*, *Bacteroides vulgatus*, and *Clostridium scindens* (DSM 5676) were used in batch culture experiments. *C. difficile* ribotype 027 is a common ribotype in Europe and North America,[1-3] while ribotype 012 is one of the common ribotypes in mainland China.[4,5] CD630 and R20291 are genetically and phenotypically well-characterised and are good representatives of their ribotypes.[6] *B. uniformis* and *B. vulgatus* were isolated from the stool of a healthy male in his 30's using fastidious anaerobe agar (Lab M, Heywood, UK) or nutrient agar (Sigma-Aldrich, St. Louis, USA), respectively.

Chemostat Model of CDI:

The working volume of each vessel was 235 ml and the growth medium feed was set to a retention time of 21 hours.[7,8] The composition of the growth medium consisted of a mixture of both soluble and insoluble starches, amino acids, peptides, proteins, vitamins, trace elements, and porcine gastric mucin (type II).[9] To mimic the gut environment cultures were maintained at a temperature of 37° C. and a pH of 6.8, were gently agitated, and kept anaerobic by sparging with oxygen-free nitrogen gas. Chemostat cultures were sampled daily from each vessel and vessels were operated for 54 days post-inoculation. Chemostat culture samples were aliquoted and stored at −80° C. for DNA extraction and mass spectrometry analysis. For NMR analysis, fresh chemostat culture was centrifuged at 20,000×g and 4° C. for 10 minutes, and the supernatant was aliquoted and stored at −80° C.

Design of Chemostat Experiments:

The inventors induced CDI in their chemostat gut model following a modified version of the methods previously described by Freeman and colleagues (Table 2).[10] Briefly, chemostat cultures were grown for 24 days without experimental manipulation to allow the communities to stabilise. After sampling vessels on day 24 the inventors added $7.8 \times 10^6$ *C. difficile* spores to each vessel to achieve an initial concentration of $3.3 \times 10^4$ spores/mL.[11] On day 25 they added another dose of $7.8 \times 10^6$ *C. difficile* spores to both vessels, and clindamycin was added to both vessels at a final concentration of 33.9 mg/L every 12 hours for 7 days (from days 25-31). After stopping clindamycin dosing chemostat cultures were left to grow for 10 days without experimental manipulation (days 32-42). This was done to allow the perturbed microbial communities to stabilise, so they could more easily determine which bacteria or metabolites were altered by FMT, and which bacteria or metabolites were able to recover after antibiotic treatment in the absence of FMT. After sampling on day 42 they added a single dose of saline to VA (control vessel) and a single dose of FMT to VB (test vessel). Chemostat cultures were then left to grow for a further 12 days without further experimental manipulation to monitor the effects of FMT on the chemostat communities (days 43-54).

*C. difficile* Spore Preparation:

*C. difficile* spores were prepared using previously described methods.[11] *C. difficile* DS1684 was grown anaerobically on fastidious agar plates supplemented with 5% defibrinated horse blood (VWR, Radnor, USA) and incubated at 37° C. for 7 days. The growth was removed from the plates using a sterile loop and resuspended in 1 mL sterile water. Next, 1 mL of 95% ethanol was mixed with the cell suspension and was incubated for 1 hour at room temperature. The cell suspension was then centrifuged at 3000×g and resuspended in 1 mL sterile water. Spores were enumerated by preparing serial 10-fold dilutions in phosphate buffered saline (PBS) (Sigma-Aldrich) and plating the dilutions on Braziers Cycloserine, Cefoxitin Egg Yolk (CCEY) agar plates (containing Braziers CCEY agar base (Lab M), 250 mg/L cycloserine (VWR), 8 mg/L cefoxitin (Sigma-Aldrich), 8% egg yolk emulsion (SLS, Nottingham UK), 2% lysed defibrinated horse blood (VWR), and 5 mg/L lysozyme (Sigma-Aldrich)).[12] Plates were incubated anaerobically at 37° C. for 48 hours and the number of colonies were enumerated.

Enumeration of *C. difficile* Counts from Chemostat Culture Samples:

*C. difficile* total viable counts (TVC) and spore counts were quantified from fresh chemostat culture samples every other day starting 26 days post-inoculation. *C. difficile* TVC were enumerated from fresh chemostat culture samples by performing serial 10-fold dilutions in PBS and plating onto Brazier's CCEY agar plates (as described above, with the addition of 2 mg/L moxifloxacin (VWR)) in triplicate using the Miles and Misra method.[13] *C. difficile* spore counts were enumerated from alcohol-shocked chemostat culture samples by mixing an equal volume of fresh chemostat culture sample with 95% ethanol and incubating at room temperature for one hour. Samples were then centrifuged at 3000×g and 4° C. for 10 minutes and resuspended in PBS. Spores were then quantified by performing serial 10-fold dilutions in PBS and plating onto Brazier's CCEY agar plates (as described above, without the addition of moxifloxacin) in triplicate using the Miles and Misra method. Plates were incubated anaerobically at 37° C. for two days and colonies were enumerated.

Preparation and Instillation of FMT:

Fresh faecal samples were placed into an anaerobic chamber within 5 minutes of defecation. FMT preparations were prepared by homogenising 10 g of stool in 100 mL of anaerobic 0.9% saline in a strainer stomacher bag (250 rpm for 1 min). The inventors added 50 mL of anaerobic saline to VA (control vessel) and 50 mL of homogenised stool to VB (test vessel). For Run 1 and Run 2 the stool transplant was prepared from the stool of a healthy male donor in his 30's, and for Run 3 the stool transplant was prepared from the stool of a healthy female donor in her 20's. Both individuals have been used as FMT donors to treat CDI patients in Imperial's FMT Programme (and therefore undergone the appropriate donor screening protocols), and had not taken antibiotics for at least 3 months prior to providing the stool sample.

DNA Extraction

DNA was extracted from 250 µL of chemostat culture using the PowerLyzer PowerSoil DNA Isolation Kit (Mo Bio, Carlsbad, USA) following the manufacturer's protocol, except that samples were lysed by bead beating for 3 min at speed 8 using a Bullet Blender Storm instrument (Chembio Ltd, St. Albans, UK). DNA was aliquoted and stored at −80° C. until it was ready to be used.

16S rRNA Gene qPCR 16S rRNA gene qPCR data was used to determine the total bacterial biomass within each sample and was performed using extracted chemostat culture DNA to following a previously published protocol.[14] A total volume of 20 µL was used for each reaction and consisted of the following: 1× Platinum Supermix with ROX (Life Technologies, Carlsbad, USA), 1.8 µM BactQUANT forward primer (5'-CCTACGGGAGGCAGCA-3'-SEQ ID No:3), 1.8 µM BactQUANT reverse primer (5'-GGACTACCGGGTATCTAATC-3' SEQ ID No:4),), 225 nM probe ((6FAM) 5'-CAGCAGCCGCGGTA-3' SEQ ID No:5) (MGBNFQ)), PCR grade water (Roche, Penzberg, Germany), and 5 µL DNA. Each PCR plate included a standard curve using E. coli DNA (Sigma-Aldrich) (3-300,000 copies per reaction in 10-fold serial dilutions) as well as no template negative controls. All samples, standards, and controls were amplified in triplicate. Extracted DNA samples were diluted to ensure they fell within the standard curve. Amplification and real-time fluorescence detections were performed using the Applied Biosystems StepOnePlus Real-Time PCR System using the following PCR cycling conditions: 50° C. for 3 min, 95° C. for 10 min. and 40 cycles of 95° C. for 15 see and 60° C. for 1 min. The inventors used a paired t-test to compare changes in log-transformed 16S rRNA gene copy number between samples at specific time points.

Pre-Processing and Analysis of 16S rRNA Gene Sequencing Data

The inventors used the Mothur package (v1.35.1) to preprocess and analyse the resulting sequencing data following the MiSeq SOP Pipeline.[15] They used the Silva bacterial database for sequence alignments (www.arb-silva.de/) and the RDP database reference sequence files for classification of sequences using the Wang method.[16] They determined the Operational Taxonomic Unit (OTU) taxonomies (phylum to genus) using the RDP MultiClassifier script. The inventors resampled and normalised data to the lowest read count in Mothur (9527 reads per sample), which resulted in greater than 99.4% coverage within each sample. The inventors used 16S rRNA gene qPCR data and the following formula to express the inventor's 16S rRNA gene sequencing data as absolute abundances (instead of relative abundances):

$$\text{Absolute abundance of } taxa = \text{relative abundance of } taxa \times \left( \frac{16S \text{ rRNA gene copy number in sample}}{\text{highest } 16S \text{ rRNA gene copy number in sample set}} \right)$$

The Shannon diversity index (H'), Pielou evenness index (J'), and richness (total number of bacterial taxa observed, $S_{obs}$) were calculated using the vegan library[17] within the R statistical package.[18]

Stream plots were prepared by plotting the absolute abundance of 16S rRNA gene sequencing data (biomass-corrected) over time (OTU-level, coloured by phylum). This was accomplished using the streamgraph function within the streamgraph library (v0.8.1) within R.[19]

$^1$H-NMR Spectroscopy Sample Preparation

Chemostat culture supernatants were randomized and defrosted at room temperature for 1 hour. Once samples were defrosted supernatants were centrifuged at 20,000×g and 4° C. for 10 minutes. Next, 400 µL of chemostat culture supernatant was mixed with 250 µL of sodium phosphate buffer solution (28.85 g Na$_2$HPO$_4$ (Sigma-Aldrich), 5.25 g NaH$_2$PO$_4$ (Sigma-Aldrich), 1 mM TSP (Sigma-Aldrich), 3 mM NaN$_3$ (Sigma-Aldrich), deuterium oxide (Goss Scientific Instruments, Crewe, UK) to 1 µL, pH 7.4)[20] and 600 µL was pipetted into a 5 mm NMR tube.

Confirmation of NMR Metabolite Identities Using 1D-NMR with Spike-in and 2D-NMR Spectroscopy The inventors used the statistical total correlation spectroscopy (STOCSY) analysis method to aid in the identification of metabolites in NMR spectra by determining correlations between intensities of the various peaks across the whole sample.[21] To further confirm if the peaks assigned to valerate and other metabolites were correct, they also conducted a two-dimensional NMR spectra (including $^1$H-$^1$H TOCSY and $^1$H-$^1$H COSY) for the chemostat culture supernatant and valerate standard using typical parameters to confirm the connectivity of the proton in the metabolites.[22,23]

For the valerate spike-in experiment one-dimensional $^1$H NMR spectra were acquired as described in the $^1$H-NMR spectroscopy methods section from the main text, except 64 scans were recorded into 65536 data points with a spectral width of 20 ppm. After normal 1D $^1$H NOESY NMR acquisition, 1 µL of valerate standard (99%, 0.9 M in PBS buffer) (Fisher Scientific, Hampton, USA) was added into the sample. A one-dimensional spectrum was recorded again to see if the relevant peaks of valerate increased.

Data Pre-Processing and Analysis of UPLC-MS Bile Acid Data

Quality control (QC) samples were prepared using a mixture of equal parts of the chemostat culture supernatants. The inventors used the QC samples as an assay performance monitor and to guide the removal of features with high variation.[24] They also spiked QC samples with defined mixtures of bile acids to determine the chromatographic retention times of specific bile acids and to aid in metabolite identification (55 bile acid standards, including 36 non-conjugated bile acids, 12 tauro-conjugated bile acids, and 7 glyco-conjugated bile acids) (Steraloids, Newport, USA).

The inventors converted the Waters raw data files to NetCDF format and extracted the data using XCMS (v1.50) package implemented within the R (v3.3.1) software. Dilution effects were corrected for using probabilistic quotient normalisation[25] and chromatographic features with high coefficient of variation (higher than 30% in the QC samples) were excluded from further analysis.

Short AsyNchronous Time-Series Analysis (SANTA)

SANTA is an automated pipeline that is implemented within R and controlled through a graphical user interface developed with Shiny.[26,27] This method analyses short time series by estimating trajectories as a smooth spline, and calculates whether time trajectories are significantly altered between different groups or over different time periods. SANTA was used to make the following comparisons: stabilisation period vs. clindamycin-dosing period, stabilisation period vs. post-clindamycin stabilisation period, and FMT-treated vs. saline-treated cultures during the treatment period. The inventors used mean subtraction to eliminate between-run differences in metabolite concentrations that arose from differences in the stool used to seed the chemostat vessels. For each metabolite, they calculated the mean for all samples within the same chemostat run, then they subtracted the mean from all its values within the run.[23] Depending upon the time series being analysed, the number of degrees of freedom (df) to fit the spline model was chosen to avoid overfitting the data (df=3-5). The inventors report the $p_{Dist}$ values, which uses the area between the mean group fitted curves to determine whether there is a difference between the two groups over time. Analysis used 1000 permutation rounds to calculate p-values and 1000 bootstrap rounds to calculate the 95% confidence bands. Reported $p_{Dist}$ values are with Benjamini-Hochberg FDR correction, and p<0.05 was considered significant.

Integration of 16S rRNA Gene Sequencing Data and Metabolite Data

The inventors used regularised Canonical Correlation Analysis (rCCA) to correlate 16S rRNA gene sequencing data (genus level) with bile acid mass spectrometry or 1H-NMR data from the same set of samples using the mixOmics library within R.[29] rCCA is an unsupervised method that maximises the correlation between the two data sets X and Y (information on the treatment groups is not taken into account in the analysis). They used the shrinkage method to determine the regularisation parameters. The plotIndiv function was used to generate unit representation plots, where each point on the scatter plot represents a single chemostat culture sample, and samples were projected into the XY-variate space. The plotVar function was used to generate correlation circle plots, where strong correlations between variables (correlations greater than 0.5) are plotted outside of the inner circle. Variables are represented through their projections onto the planes defined by their respective canonical variates. In this plot the variables projected in the same direction from the origin have a strong positive correlation, and variables projected in opposite directions form the origin have strong negative correlations. Variables with stronger correlations sit at farther distances from the origin.

C. difficile Germination Batch Cultures with Taurocholic Acid (TCA)

To test the effects of TCA on C. difficile germination the inventors resuspended C. difficile DS1684 spores in sBHI with or without 1% TCA (Sigma-Aldrich) in triplicate.[30] The $OD_{600}$ was measured immediately after inoculation of broths (time zero) and after an overnight incubation at 37° C. in anaerobic chamber. A paired t-test was used to determine whether TCA affected C. difficile germination.

C. difficile Vegetative Growth Batch Cultures with TCA

To test the effects of TCA on C. difficile vegetative growth the inventors centrifuged an overnight culture of C. difficile DS1684 at 3000×g for 10 minutes and resuspended the cells in sBHI with or without 1% TCA (in triplicate). The $OD_{600}$ was measured at time zero and cultures were incubated at 37° C. in an anaerobic chamber. Additional $OD_{600}$ measurements were taken at 2, 4, 6, and 8 hours post-inoculation, and the change in $OD_{600}$ was plotted against time. A paired t-test was used to determine whether TCA affected vegetative growth during the exponential phase.

The following methods represent those used in a human study.

Study Participants

This study received approval from the UK National Research Ethics Centres (13/LO/1867) and REB approval from all participating institutions. Stool samples were collected from participants with rCDI (26 participants) and their matched donors (17 participants) for FMT. rCDI was diagnosed on a combination of clinical and laboratory criteria. Clinically, participants with CDI had recurrence of diarrhoea (>3 unformed bowel movements every 24 hours) within 8 weeks of completing a prior course of treatment (with resolution of diarrhoea with anti-CDI antibiotics for prior episodes), with no clear alternate explanation for diarrhoea. CDI diagnosis was confirmed with laboratory testing, via positive ELISA for toxins A/B, with confirmation via PCR. For CDI participants, samples were collected shortly prior to FMT (whilst on suppressive doses of anti-CDI antibiotics), and again at 8-10 weeks post-successful FMT. Patient characteristics (including age, gender, duration of rCDI and medication use) were collected (Table 3).

TABLE 3

Clinical characteristics of FMT recipients.

| Characteristic | Value |
| --- | --- |
| Age (years) (mean +/− SD) | 66 +/− 13 |
| Sex | 65% female (17/26) |
| BMI pre-FMT (kg/m$^2$) | 25.01 +/− 7 |
| Median recurrences | 3 (range: 1-5) |
| Median prior CDI-related hospitalisations | 1 (range: 1-3) |
| Reported antibiotic use prior to CDI | 88% (23/26) |
| Reported previous failed vancomycin taper | 58% (15/26) |
| Route of administration | 31% capsulised (8/26), 69% colonoscopy (18/26) |
| PPI use | 42% (11/26) |
| Statin use | 12% (3/26) |

FMT Protocol

Donor inclusion/exclusion criteria, screening and testing followed previously-described recommendations. FMT was administered either by colonoscopy or via capsule, with 4 L of polyethylene glycol bowel preparation administered to all patients on the day prior to FMT. FMT performed via colonoscopy used thawed faecal slurry which had been frozen in 10% glycerol (90% normal saline (v/v), provided by OpenBiome). Capsule preparation and administration was as previously outlined[11], and capsules contained frozen FMT with 10% v/v glycerol as cryopreservative.

DNA Extraction and 16S rRNA Gene Sequencing

DNA was extracted from 250 mg of stool using the PowerLyzer PowerSoil DNA Isolation Kit (MoBio, Carlsbad, CA, USA) following manufacturer's instructions, with the addition of a beat beating step for 3 minutes at speed 8 in a Bullet Blender Storm (Chembio Ltd, St Albans, UK). DNA was stored at −80° C. prior to analysis. 16S rRNA gene qPCR data was used to determine the total bacterial biomass within each sample.

Sample libraries were prepared following Illumina's 16S Metagenomic Sequencing Library Preparation Protocol with several modifications. Firstly, the V1-V2 regions of the 16S rRNA gene were amplified using the primers listed in Table 4. Next, the index PCR reactions were cleaned up and normalised using the SequalPrep Normalization Plate Kit (Life Technologies, Paisley, UK). Sample libraries were quantified using the NEBNext Library Quant Kit for Illumina (New England Biolabs, Hitchin, UK). Sequencing was performed on an Illumina MiSeq platform (Illumina Inc., Saffron Walden, UK) using the MiSeq Reagent Kit v3 (Illumina) and paired-end 300 bp chemistry.

panol in a Biospec bead beater with 1.0 mm Zirconia beads. After centrifugation (16,000×g, 20 minutes) the supernatant was filtered using 0.45 μm microcentrifuge filters (Costar, Corning).

Bile acid analysis of faecal extracts was performed using ACQUITY UPLC (Waters Ltd, Elstree, UK) coupled to a Xevo G2 Q-ToF mass spectrometer equipped with an electrospray ionization source operating in negative ion mode, using the method described by Sarafian and colleagues[47].

Methodology for subsequent pre-processing and analysis of UPLC-MS bile acid data is described below. Integration of metataxonomic and UPLC-MS bile data is described in below.

Real-Time PCR for the Quantification of Bsh and baiCD Gene Abundance qPCR was performed using extracted DNA to quantify gene abundance. Gene abundance was quantified for i)

TABLE 4

V1-V2 primers used for 16S rRNA gene sequencing on the Illumina MiSeq. The forward primer mix was composed of four different forward primers, mixed at a ratio of 4:1:1:1 (28F-YM:28F-*Borrellia*:28FChloroflex:28F-Bifdo). Bases in bold are the MiSeq adapter sequences.

| Primer name | Primer sequence |
| --- | --- |
| 28F-YM (forward primer) SEQ ID No: 6 | TCGTCGGCAGCGTCAGATGTGTATAAGAGACAGGAGTTTGATYMTGGCTCAG |
| 28F-*Borrellia* (forward primer) SEQ ID NO: 7 | TCGTCGGCAGCGTCAGATGTGTATAAGAGACAGGAGTTTGATCCTGGCTTAG |
| 28FChloroflex (forward primer) SEQ ID NO: 8 | TCGTCGGCAGCGTCAGATGTGTATAAGAGACAGGAATTTGATCTTGGTTCAG |
| 28F-Bifdo (forward primer) SEQ ID NO: 9 | TCGTCGGCAGCGTCAGATGTGTATAAGAGACAGGGGTTCGATTCTGGCTCAG |
| 388R (reverse primer) SEQ ID NO: 10 | GTCTCGTGGGCTCGGAGATGTGTATAAGAGACAGTGCTGCCTCCCGTAGGAGT |

Ultra Performance Liquid Chromatography-Mass Spectrometry (UPLC-MS) Profiling of Faecal Bile Acids Faecal samples were lyophilized for 24 hours using a VirTis Benchtop BTP 8ZL freeze dryer (BPS, UK). The dried samples were weighed and bile acids were extracted using a 2:1:1 (vol) mixture of water, acetonitrile and 2-prospecified groups of bsh (using degenerate primer sets previously designed and optimised by the inventors (Table 5)) and ii) baiCD (using primers previously described in the literature). Whilst bsh primers were degenerate, each primer set used was specific for an individual BSH group.

TABLE 5

Primers sequences and PCR conditions for bsh and baiCD qPCR reactions.

| Group | Primer Sequence (5'-3') | F/R | Cycling Conditions | Expected Product Site (bp) |
| --- | --- | --- | --- | --- |
| 1a | CACATATTGTGGCACGAACAATHGAR TGGGG (SEQ ID NO 11) | F | 95° C. for 10 min, (95° C. for 15 sec, | 570 |
| | CTGTGCCCGGATACAGATTAACRTAR TTRTT (SEQ ID NO: 12) | R | 55° C. for 1 min) × 40 cycles | |
| 1b | CGGCGTTCCGCATTTYTAYGARAA (SEQ ID NO: 13) | F | 95° C. for 10 min, (95° C. for 15 sec, | 318 |

TABLE 5-continued

Primers sequences and PCR conditions for bsh and baiCD qPCR reactions.

| Group | Primer Sequence (5'-3') | F/R | Cycling Conditions | Expected Product Site (bp) |
|---|---|---|---|---|
| | GTTCAATGCCAATCGGAATATCRAAR TTRTT (SEQ ID NO: 14) | R | 55° C. for 1 min) × 40 cycles | |
| 3c/e | TTTTGGCCGAACACTGGAYTAYGARTT (SEQ ID NO: 15) | F | 54° C. for 30 sec, 95° C. for 5 min, | 774 |
| | TCAACGGAGCCCAGAATATGRAARA AYTG (SEQ ID NO: 16) | R | (95° C. for 15 sec, 72 for 10 min) × 40 cycles | |
| baiCD | GGWTTCAGCCCRCAGATGTTCTTTG (SEQ ID NO: 17) | F | 94° C. for 2 min, (94° C. for 20 sec, | 1300 |
| | GAATTCCGGGTTCATGAACATTCTKCKAAG (SEQ ID NO: 18) | R | 52° C. for 30 sec, 69° C. for 90 sec) × 35 cycles, 68° C. for 10 min | |

A total reaction volume of 25 µl was used for each reaction, consisting of 20 µl master mix and 5 µl diluted DNA (12.5 ng total per reaction). All DNA was diluted in buffer EB (Qiagen, Hilden, Germany). The master mix consisted of 5.5 µl PCR grade water (Roche, Penzberg, Germany), 12.5 µl of 2×SYBR green master mix (ThermoFisher Scientific, Waltham, Massachusetts, USA), 1 µl of 10 µM forward primer (Eurofins Genomics, Wolverhampton, UK) and 1 µl of 10 µM reverse primer (Eurofins Genomics). One bacterial strain from the relevant reference group was selected as a standard for each primer set (bsh group 1A—*Bacteroides plebius*; bsh group 1B—*Bacteroides ovatus*; bsh group 3C—*Blautia obeum*; baiCD—*Clostridium scindens* (DSMZ 5676, Braunschweig, Germany)). Serial dilutions of each isolate were used to create a standard curve. Thermocycling conditions for each primer set are summarised in Table 9. A melt curve stage was performed post-cycling to confirm primer specificity. Copy number was calculated from qPCR data using the following formula: gene abundance=(quantity (ng)×6.022×10$^{23}$ (gene copy number/mol))/(length of product×1×10$^9$ (ng/g)×660 (g/mol)). A mean copy number for each set of triplicates was calculated and divided by the total DNA per reaction to obtain average copy number per ng DNA.

Bile Salt Hydrolase Enzyme Activity Assay

Faecal water was prepared and total faecal protein quantified using a similar method to that previously-described by Morris and co-workers, but with the addition of bacterial and mammalian protease inhibitor cocktails (G Biosciences, St Louis, MO, USA), as well as DTT to 1 mM final concentration (Roche, Welwyn Garden City, UK) to minimise enzyme oxidation.

The BSH assay itself was an adaptation of the conventional precipitation-based assay[49-51]. The assay was performed in a clear flat-bottomed 96-well microtitre plate and incubated at 37° C. at pH 5.8 for up to 8 hours. In a total volume of 200 µl, 50 µg of faecal protein was incubated with sodium phosphate buffer (pH 5.8, final concentration of 0.02 mM), and taurodeoxycholic acid (Merck, Damstadt, Germany) (at final concentration 1 mM). To prevent evaporation during incubation, wells were overlaid with 501 µl of light paraffin oil (0.85 g/ml; PanReac AppliChem, Barcelona, Spain)[51]. Samples were assayed in triplicate, with precipitation of insoluble deoxycholic acid monitored by absorbance measurement at 600 nm ($OD_{600}$) using a microplate reader (MultiSkan Go, Thermo Scientific, Dartford, UK). Faecal protein incubated with phosphate-buffered saline served as a negative control, and faecal protein incubated with varying concentrations of deoxycholic acid (Merck) was used to establish a standard curve to quantify precipitate formation.

*Clostridioides difficile* Germination Batch Cultures

These cultures were performed via adaptation of a previously-described protocol. A range of different bacterial species established to produce BSH from different BSH groups (and *Clostridium scindens*, as a known 7-α-dehydroxylase-producer) were incubated in sBHI (Brain Heart Infusion broth (Sigma-Aldrich), with 5 mg/ml yeast extract (Sigma-Aldrich), and 0.1% w/v L-cysteine (Sigma-Aldrich)), with or without 1% w/v TCA added. These BSH producing organisms were *Bacteroides ovatus* (BSH group 1B), *Collinsella aerofaciens* (group 2), *Bacteroides vulgatus* (group 3C) and *Blautia obeum* (group 3C) (two organisms were picked from group 3C given that this is a large group). This included wild type *E. coli* MG1655 (which does not contain bsh genes within its genome), along with two forms of *E. coli* MG1655 into which bsh genes had been cloned using pBKminiTn7GM2 under the control of the P44 promotor, as previously-described. Specifically, these were *E. coli* expressing a bsh gene with low activity ('*E. coli* $BSH_{low}$', with bsh gene cloned from *Bifidobacteria adolescentis*, with narrow substrate range against conjugated bile acids), and *E. coli* expressing a bsh gene with high activity ('*E. coli* $BS_{High}$', with bsh gene cloned from *Lactobacillus salivarius*, containing BSH with high glycine and taurine-deconjugating activity). Overnight incubation occurred at 37° C. in an ElectroTek AW 400TG Anaerobic Workstation (ElectroTek, West Yorkshire, UK). Cultures were centrifuged at 20,000×g for 10 minutes at 4° C.; supernatant from the culture was diluted 1:3 with sBHI without added TCA, and again filter sterilised (0.2 □m). *C. difficile* spores from three different ribotypes (a non-toxigenic ribotype, 010 (strain DS1684), and two toxigenic ribotypes, 012 (strain CD630) and 027 (strain R20291)) were resuspended in supernatant in triplicate, and an $OD_{600}$ reading taken on a microplate reader at time zero (adjusted to $OD_{600}$ of 0.1 with supernatant/sBHI mix), and again after overnight incubation. An increase in $OD_{600}$ reading after overnight incubation was interpreted as indicating that spores had undergone germination and had grown as vegetative cells.

In addition, UPLC-MS was performed on batch culture supernatants to establish bile acid profiles. Bile acid extraction was performed by taking 75 µl of supernatant and adding 225p of cold methanol, followed by incubation at −30° C. for 2 hours; tubes were centrifuged at 9,500×g and 4° C. for 20 min and 120 µl of supernatant was loaded into vials. UPLC MS analysis was otherwise as described above.

The protocol used for C. difficile spore preparation is described below

Statistical Analysis

Multivariate UPLC-MS bile acid profiling data analysis is described below. Univariate statistics were performed using GraphPad Prism, v7.03; Mann-Whitney test was used to compare donor with pre-FMT or post-FMT, whilst Wilcoxon rank sum was used to compare pre-FMT with post-FMT samples (all statistics were two-tailed tests). Correlation of metataxonomic and metabolomics data was undertaken via regularised Canonical Correlation Analysis (rCCA), using the mixOmics library within R53. Analysis of batch culture experiments used ANOVA (for germination assays) and Kruskal-Wallis (for bile acid assays) with multiple test correction using Benjamini-Hochberg. All box and whiskers plots are shown with: central line as median; edges of box as 25-75% percentile; whiskers as maximum to minimum. Error bars on bar charts represent +/−standard deviation.

16S rRNA Gene qPCR

To quantify the biomass present in each sample the inventors performed 16S rRNA gene qPCR using DNA extracted from stool and following a previously published protocol. For each reaction, a total of 20 µL was made up, consisting of the following: ix Platinum Supermix with ROX (Life Technologies, Carlsbad, USA), 1.8 µM BactQUANT forward primer SEQ ID NO: 3 (5'-CC-TACGGGAGGCAGCA-3'), 1.8 µM BactQUANT reverse primer SEQ ID NO: 4 (5'-GGACTACCGGGTATCTAATC-3'), 225 nM probe ((6FAM) SEQ ID NO: 5 (5'-CAGCAGCCGCGGTA-3') (MGBNFQ)), PCR grade water (Roche, Penzberg, Germany), and 5p DNA. For each plate the inventors included an E. coli genomic DNA (Sigma-Aldrich) standard curve, consisting of 3-300,000 copies per reaction in 10-fold serial dilutions, and a 'no template' negative control. All samples, standards, and controls were performed in triplicate. Extracted DNA samples were diluted to ensure they fell within the standard curve. The Applied Biosystems StepOnePlus Real-Time PCR System was used for amplification and real-time fluorescence detections using the following PCR cycling conditions: 50° C. for 3 min, 95° C. for 10 min, and 40 cycles of 95° C. for 15 see and 60° C. for 1 min. The inventors used a Mann-Whitney test to compare 16S rRNA gene copy number between donor and FMT samples, and Wilcoxon signed-rank test to compare changes between pre- and post-FMT.

Metataxonomic Analysis

The output data was analysed using the Mothur package (v1.35.1) following the MiSeq SOP Pipeline[2]. Sequence alignments were performed using the Silva bacterial database (www.arb-silva.de/), and the RDP database reference sequence files were used for sequence classification using the Wang method[3]. Operational Taxonomic unit (OTU) taxonomies (phylum to genus) were established using the RDP MultiClassifier Script. Where possible, species were identified from OTU data using a standard nucleotide BLAST of the 16S rRNA sequences (NCBI) with strict criteria (query cover 100% and ≥97% identity, with no other candidate species above 97% identity). Genus-level annotation was made where query cover was 100% and 94% identity. The non-metric multidimensional scaling (NMDS) plot and PERMANOVA p-values were generated using the UniFrac weighted distance matrix generated from Mothur, and analysed using the Vegan library within the R statistical package[4]. Family-level extended error bar plots were generated using the Statistical Analysis of Metagenomic Profiles (STAMP) software package using White's non-parametric t-test with Benjamini-Hochberg FDR[5]. The α-diversity (Shannon diversity index, H') and richness (total number of bacterial taxa observed, $S_{obs}$) were calculated within Mothur and statistical tests were performed using GraphPad Prism v7.03. A p-value of 0.05 and a q-value of 0.05 was considered significant.

Changes in microbial composition were also assessed at the OTU level. Differences in mean OTU relative proportions>1% were measured between donor and pre-FMT samples, and between pre-FMT and post-FMT samples, using White's non-parametric test and Benjamini-Hochberg FDR. From these data, OTUs were analysed that were enriched in donors in comparison to pre-FMT samples, and those enriched post-FMT in comparison to pre-FMT samples.

UPLC-MS Bile Acid Data: Data Pre-Processing and Analysis

Quality control (QC) samples were prepared by pooling equal volumes of the faecal filtrates. QC samples were used as an assay performance monitor[6], and as a proxy to remove features with high variation. QC samples were also spiked with mixtures of bile acid standards (bileacidstandards including 36 non-conjugated, 12 conjugated with taurine, seven conjugated with glycine (Steraloids, Newport, RI, USA)) and were analysed along with the stool samples to determine the chromatographic retention times of bile acids and to aid in metabolite identification.

Waters raw data files were converted to NetCDF format and data were extracted using XCMS (v1.50) package with R (v3.1.1) software. Probabilistic quotient normalisation[7] was used to correct for dilution effects and chromatographic features with coefficient of variation higher than 30% in the QC samples were excluded from further analysis. The relative intensities of the features were corrected to the dry weight of the faecal samples.

Multivariate analysis of UPLC-MS bile acid profiling data was performed on pareto-scaled data. OPLS-DA models were validated using CV-ANOVA, which provides a significance test of the null hypothesis of equal residuals between the model under validation and a randomly-fitted model which uses the same data[8]. S-plots were used to visualise the highly-influential discriminatory features, and depict the covariance and the correlation structure between the X-variables and the predictive score t[1] of the model. Features at the far ends of the plot have a very high reliability whilst having a high model influence due to their high variance in the dataset[9].

Integration of metataxonomic and UPLC-MS bile acid data

Regularised Canonical Correlation Analysis (rCCA) was used to correlate metataxonomic data (family-level) with UPLC-MS bile acid profiling data from the same samples using the mixOmics library within R[10,11]. This technique maximises the correlation between the two data sets X and Y. The shrinkage method was applied to determine regularisation parameters. Unit representation plots were generated using the plotIndiv function, where each sample is represented as a single point on the scatter plot, and samples were projected into XY-variate space. Correlation circle plots were generated using the plotVar function. On these plots strong correlations between variables are plotted outside of the inner circle (correlations where r>0.5). Variables are represented through their projections onto the planes defined by their respective canonical variables. Strong positive correlations are present when variables are projected in the same direction from the origin, and strong negative correlations are present when variables are projected in opposite directions. Variables present at farther distances from the origin have stronger correlations.

Isolation of Bacteria Used as Standards for Bsh Gene qPCR and in Batch Cultures

Bacteroides plebius, Bacteroides ovatus, Bacteroides vulgatus, Collinsella aerofaciens and Blautia obeum were previously isolated from the stool of a healthy male donor in his 20's. Bacteroides plebius was isolated from fastidious anaerobe agar plates (Acumedia, USA) with 5% horse blood (VWR, USA). Bacteroides ovatus and Bacteroides vulgatus were isolated from nutrient agar plates (Sigma-Aldrich, USA). Blautia obeum was isolated from de Man, Rogosa and Sharpe agar plates (Sigma-Aldrich). Collinesella aerofaciens was isolated from tryptic soy agar plates (Sigma-Aldrich).

DNA extraction was performed on the isolates using the E.Z.N.A.® Bacterial DNA Kit (Omega, USA) with the addition of a bead beating using the Bullet Blender Storm (speed 8 for 3 min). A ~900 bp region of the 16S rRNA gene was amplified using previously published primers[12] and DNA was sequenced at Macrogen Europe. Isolates were identified by performing a standard nucleotide BLAST of the 16S rRNA gene sequences (NCBI).

Clostridioides difficile Spore Preparation

C. difficile spores were prepared using previously described methods[13]. Specifically, C. difficile 010, 012 and 027 were grown anaerobically on fastidious anaerobe agar plates supplemented with 5% v/v defibrinated horse blood (VWR, Radnor, USA) and incubated at 37° C. for 7 days. The growth was removed from the plates using a sterile loop and resuspended in 1 ml of sterile water. Next, 1 ml of 95% ethanol was mixed with the cell suspension and was incubated for 1 hour at room temperature. The cell suspension was centrifuged at 3,000×g and resuspended in 1 ml sterile water. Spores were stored at −80° C. until use.

Results

C. difficile Total Viable Counts and Spore Counts:

Following the addition of C. difficile spores to each vessel C. difficile total viable counts (TVC) and spore counts were enumerated every other day until the end of the experiment (FIG. 1). The inventors found an increase in C. difficile TVC during the clindamycin-dosing period (p<0.001). They also found a 94% reduction in C. difficile TVC (p=0.025) and an 86% reduction in C. difficile spore counts (p=0.034) in FMT-treated cultures compared to saline-treated cultures.

Figure 2:
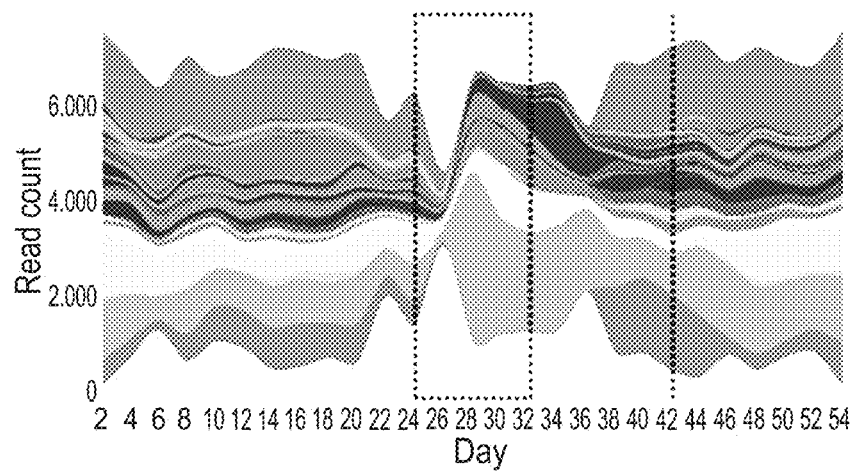
Figure 2:
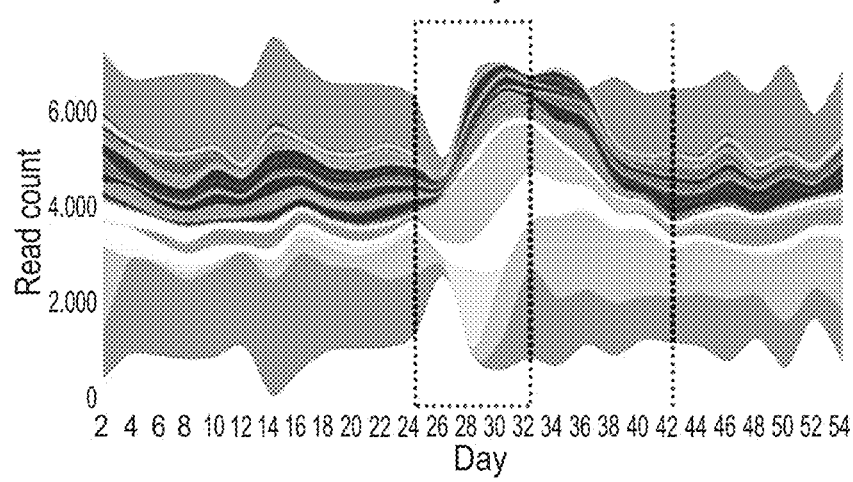
Figure 2:
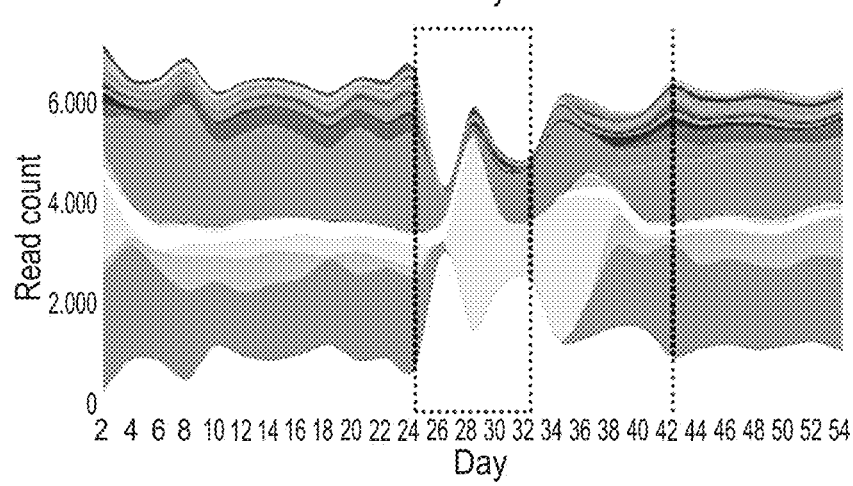
Figure 2:
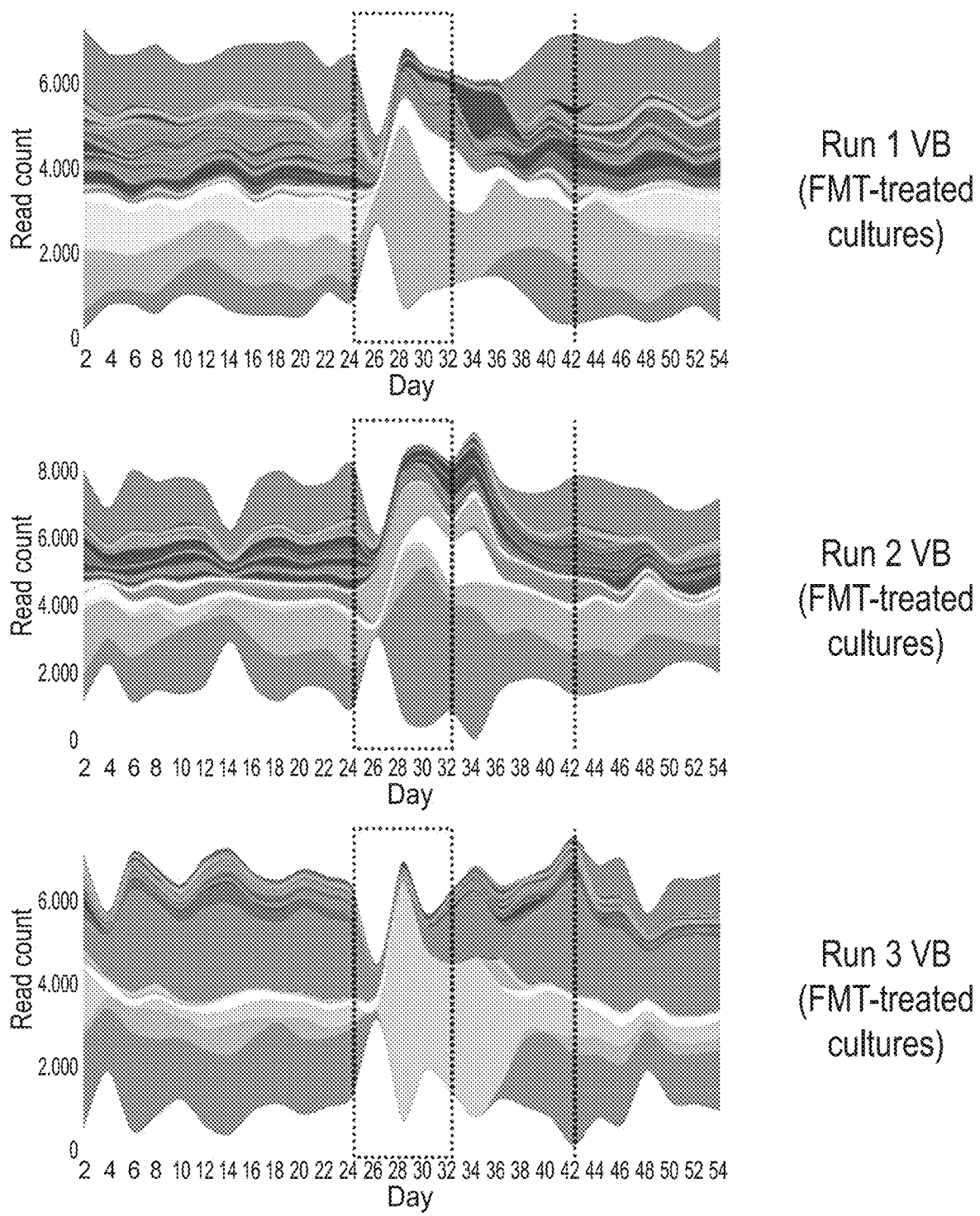
Figure 7:
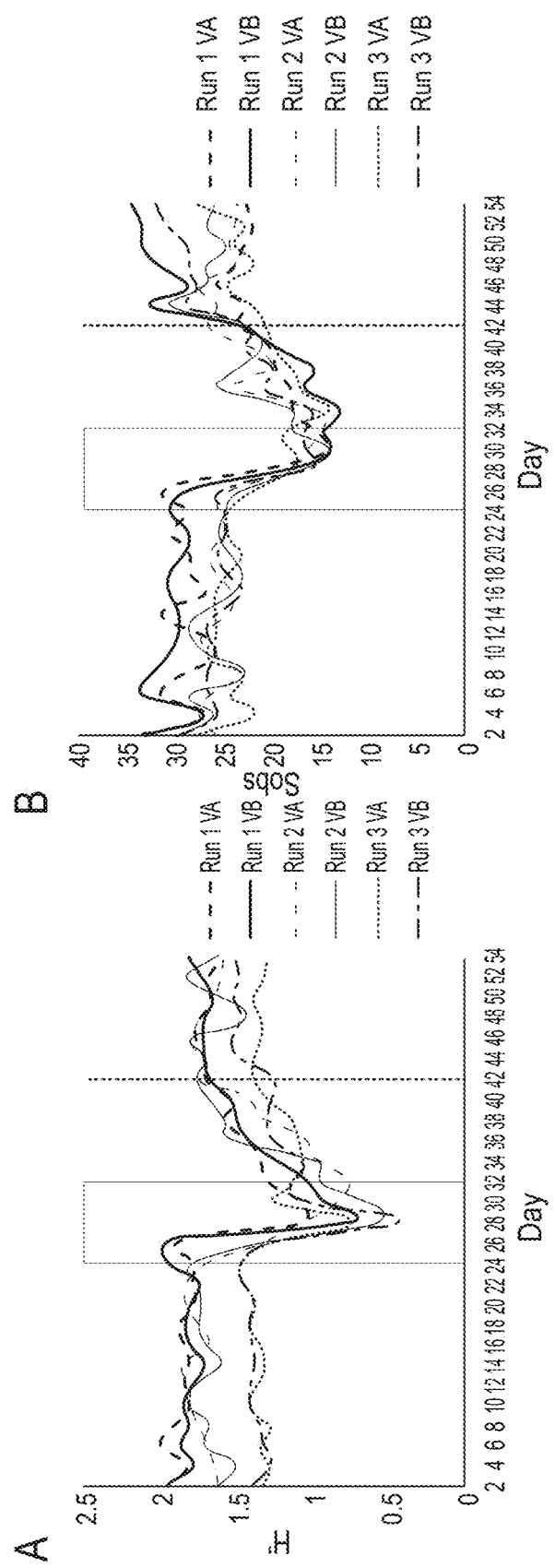
Figure 7:
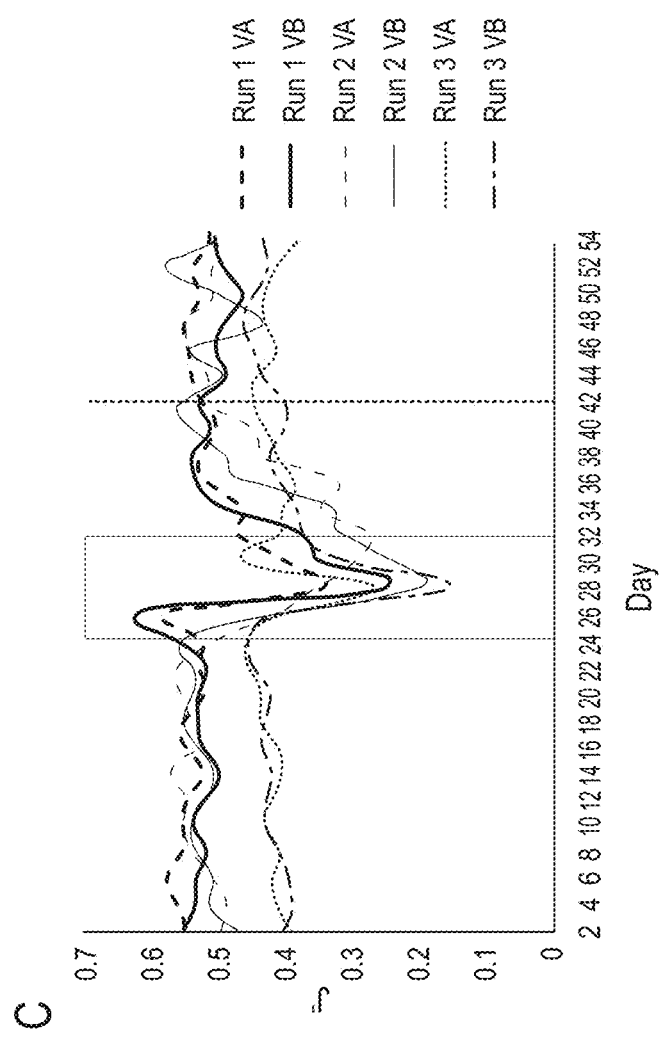

Bacterial Community Composition:

The inventors found that clindamycin dosing of chemostat cultures altered the composition and the biomass of the bacterial communities (FIG. 2). Clindamycin dosing caused an initial decrease in the total bacterial biomass one day after starting clindamycin dosing (p<0.001), however the total bacterial biomass increased over time to reach pre-clindamycin levels by the end of the clindamycin dosing period (p>0.05). Clindamycin dosing also resulted in a decrease in bacterial diversity (p=0.002), richness (p=0.001) and evenness (p=0.004) (FIG. 7). There was a significant increase in richness following FMT treatment (p=0.035), however diversity (p>0.05) and evenness (p>0.05) remained unchanged.

Figure 3:
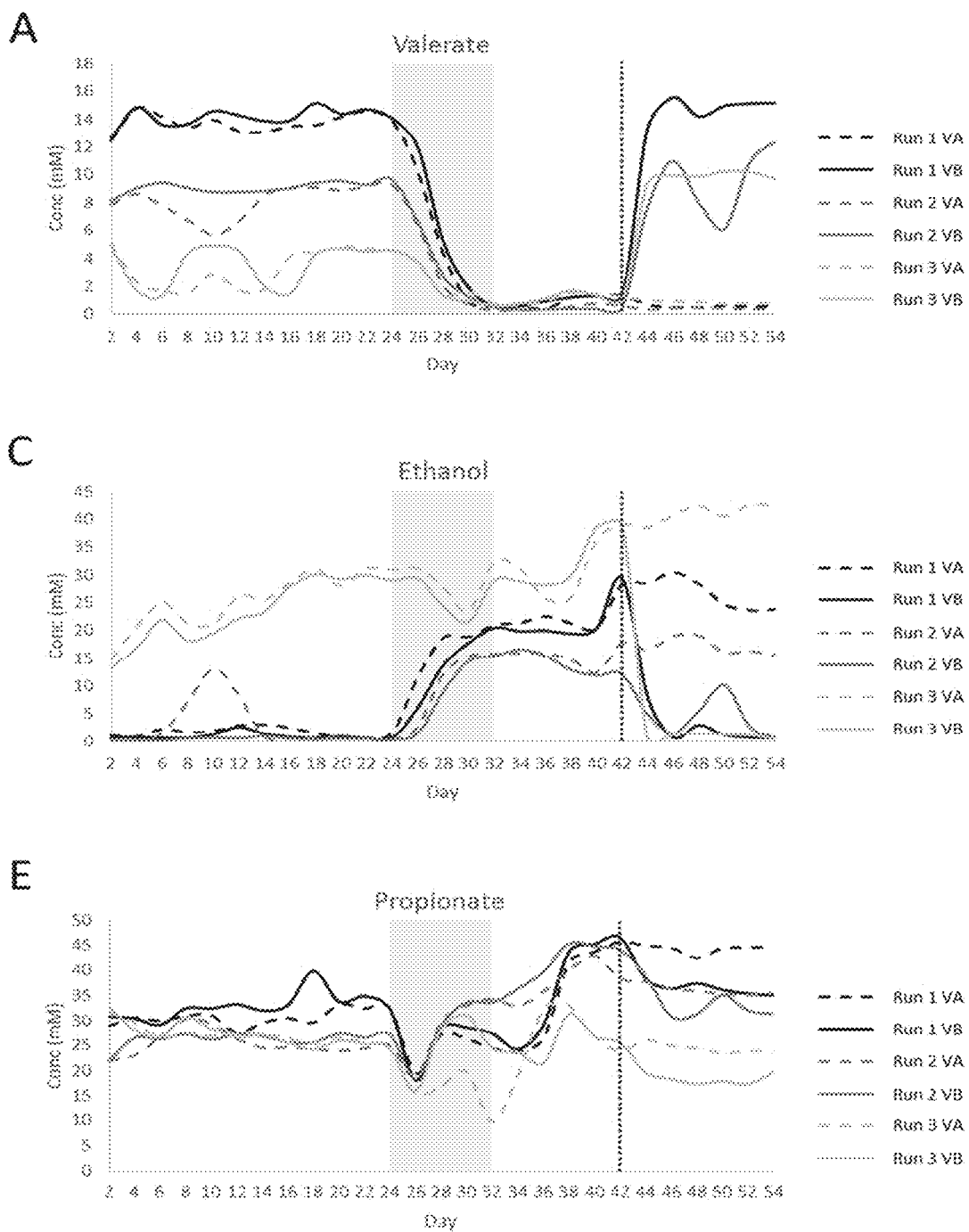
Figure 3:
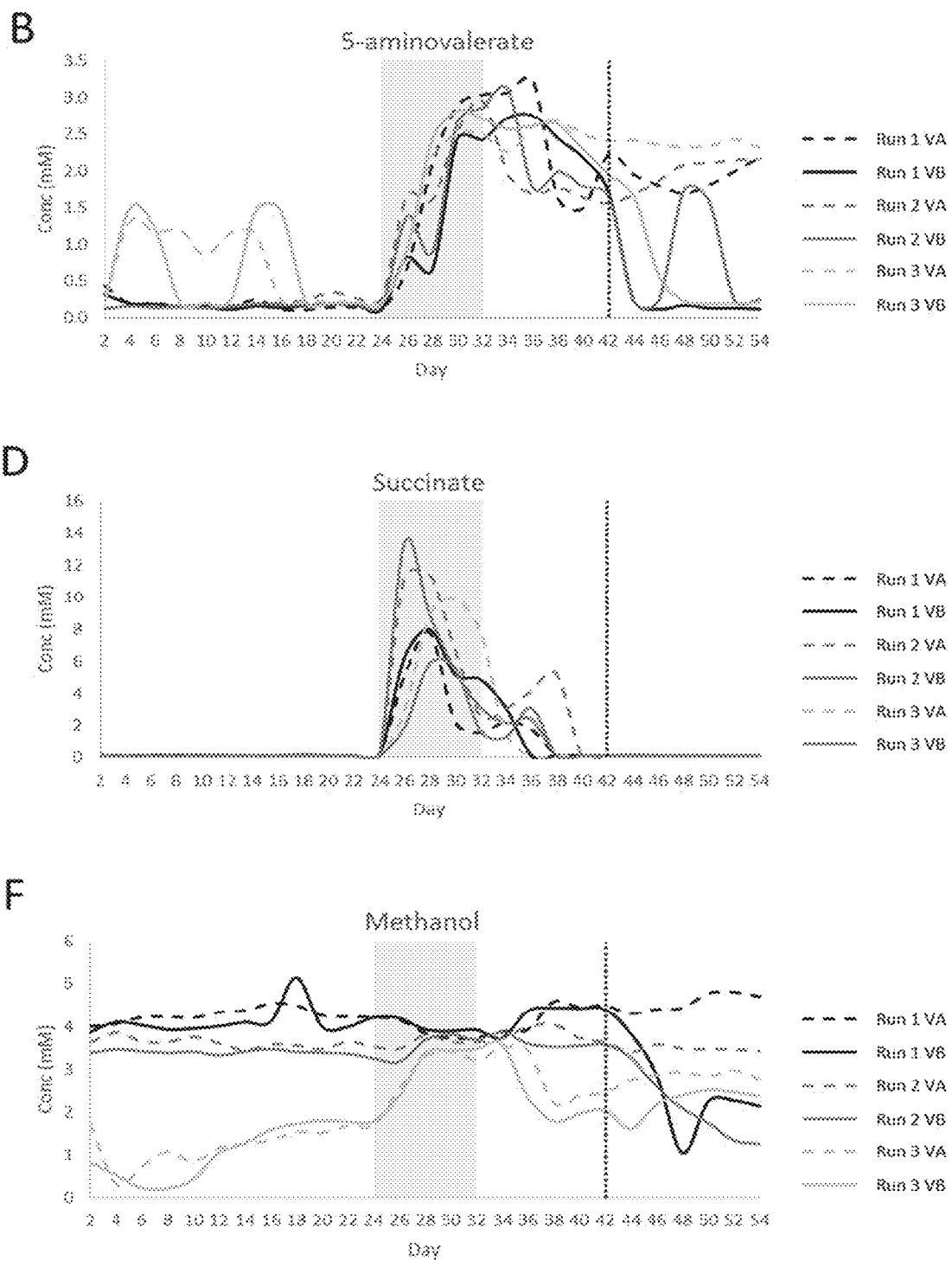
Figure 8:
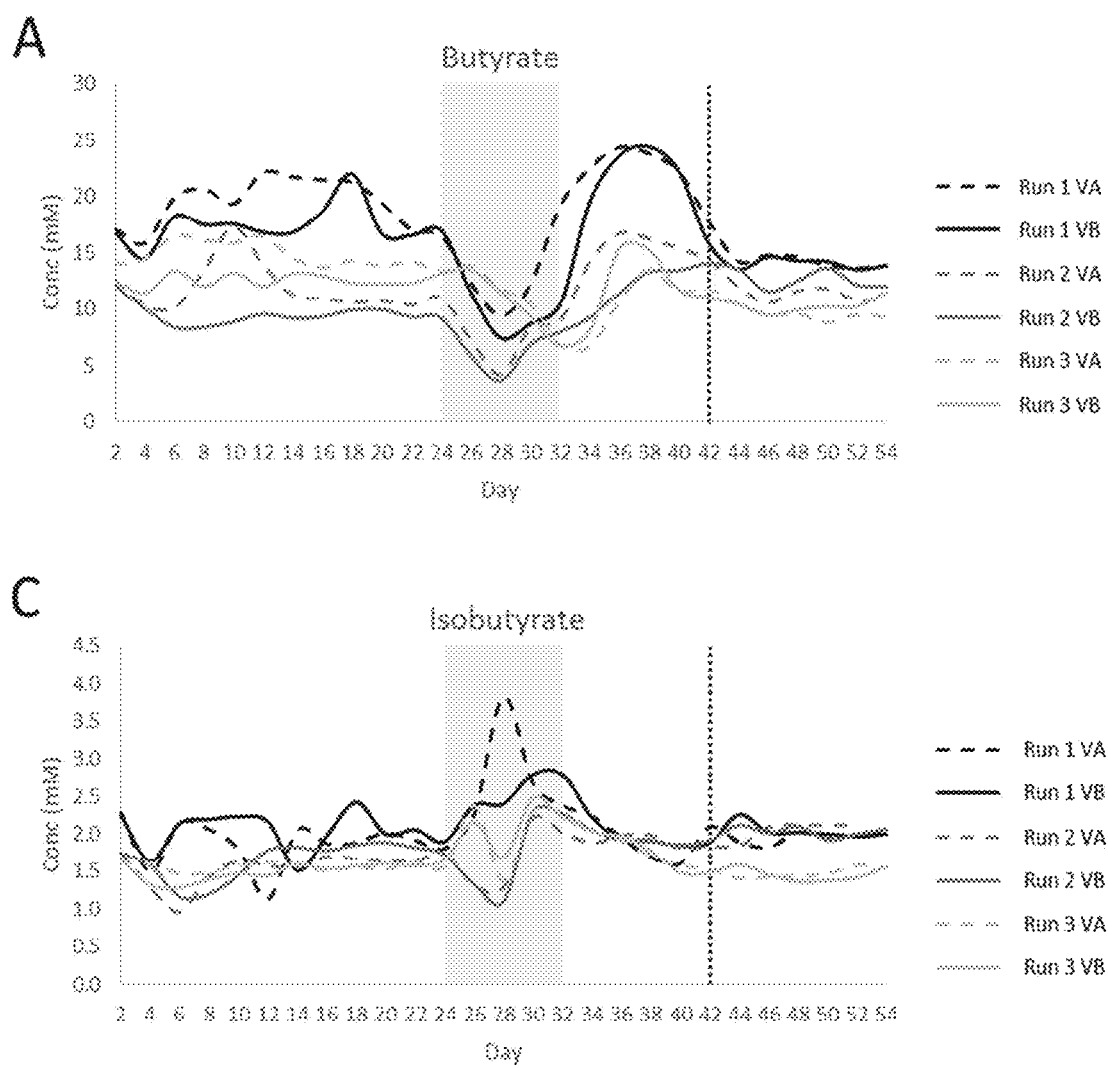
Figure 8:
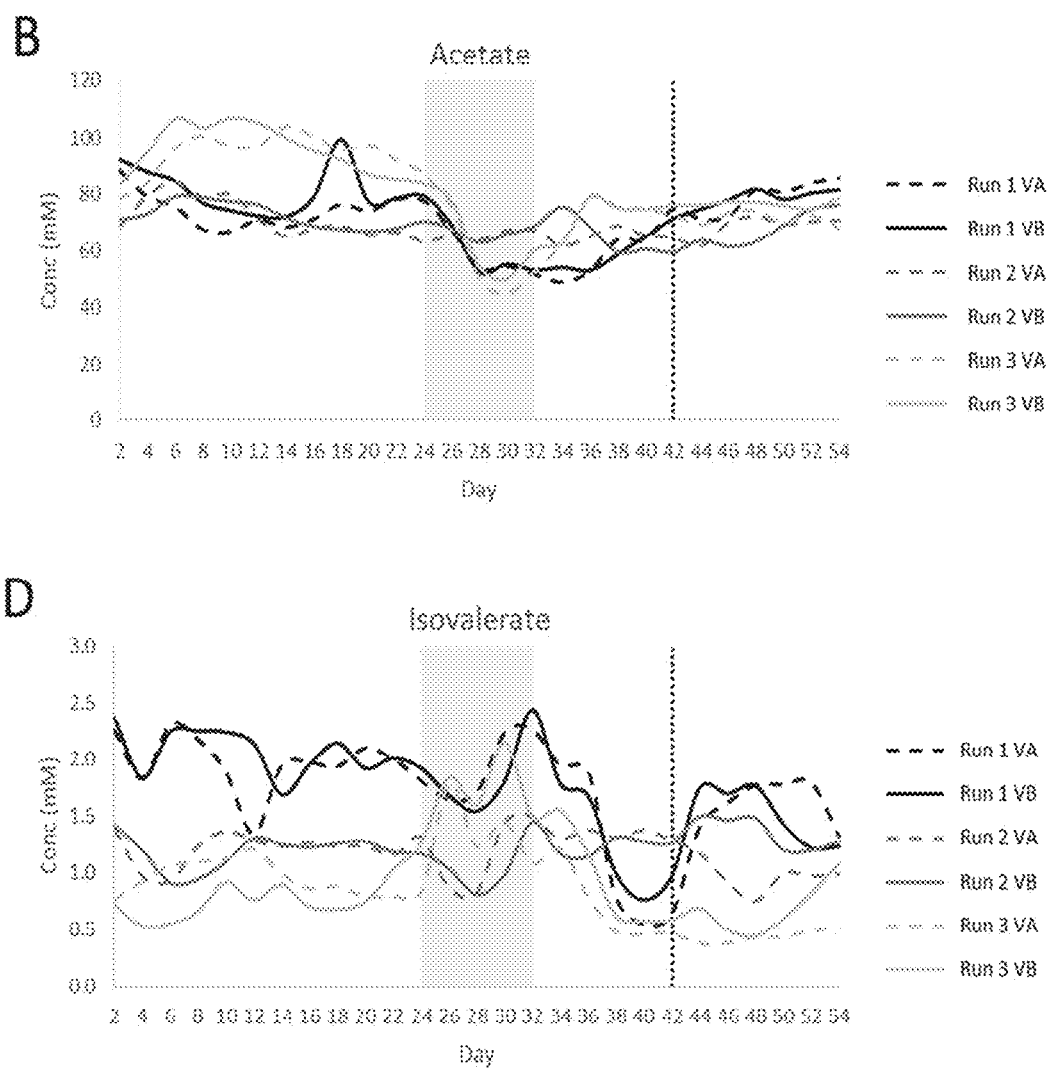
Figure 9:
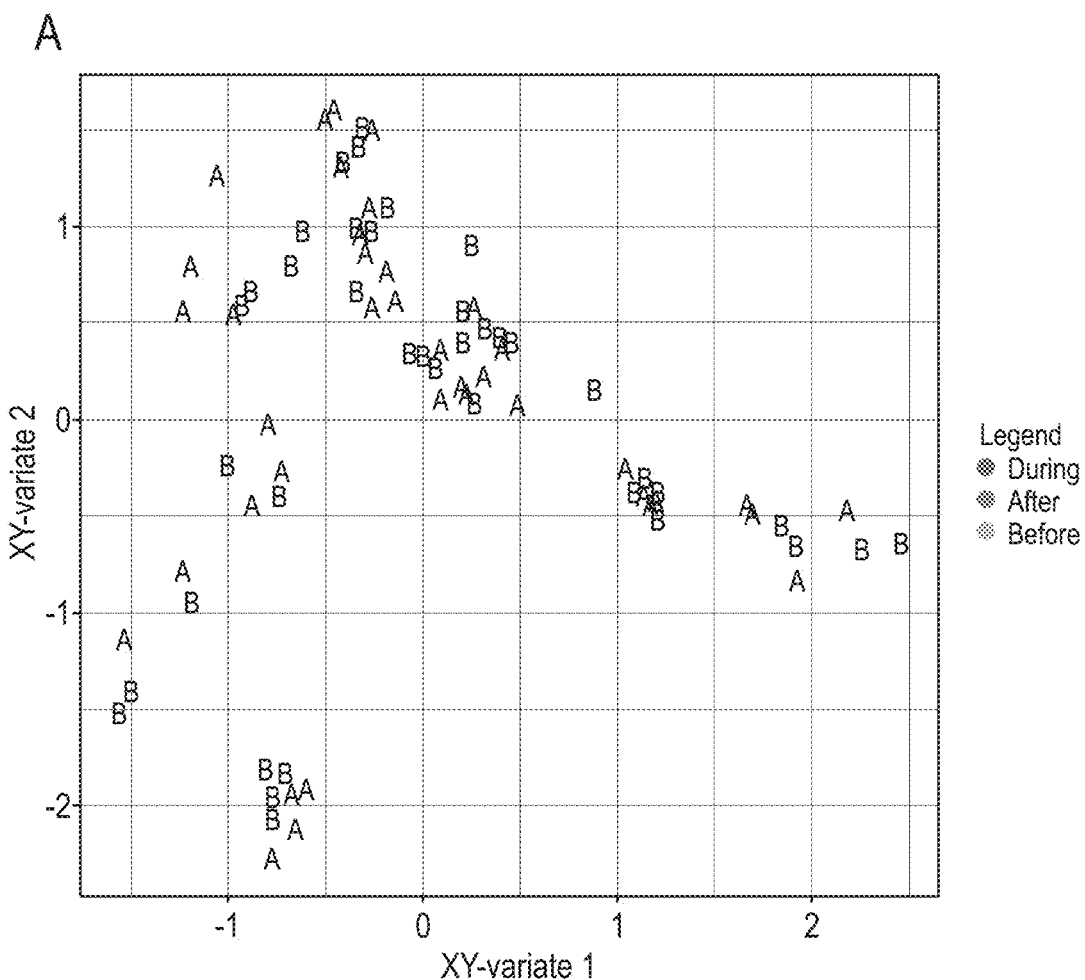
Figure 9:
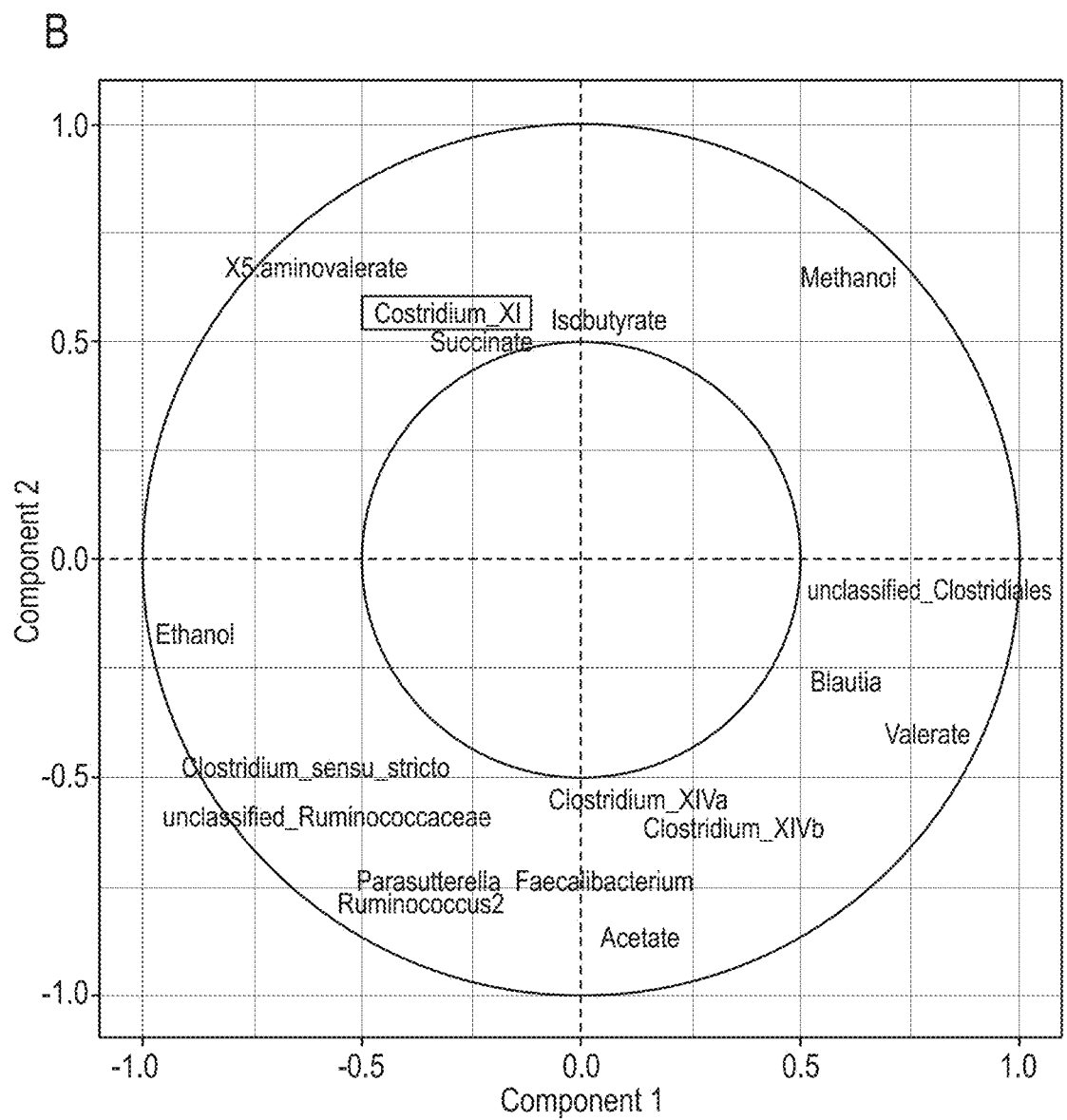
Figure 9:
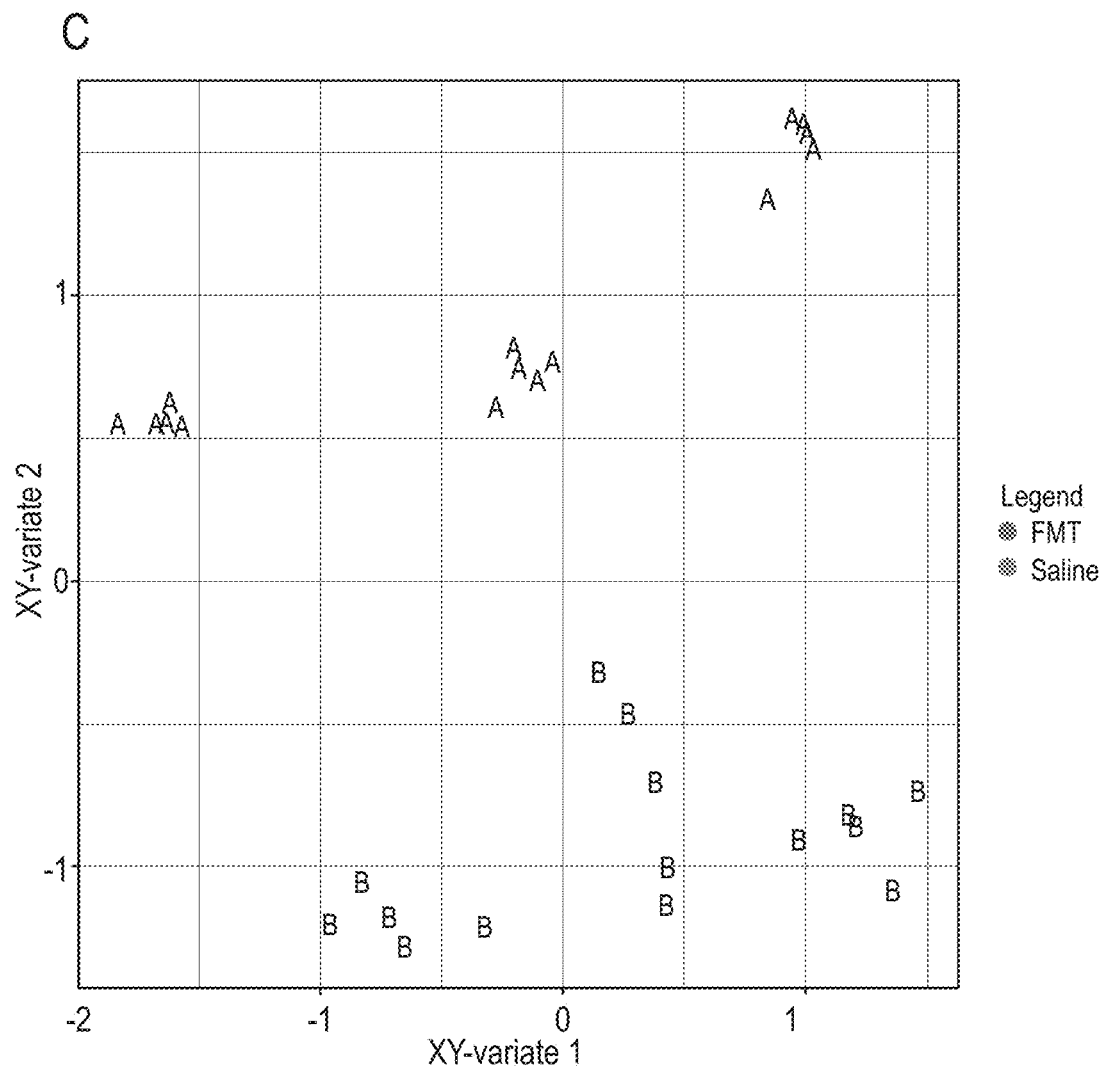
Figure 9:
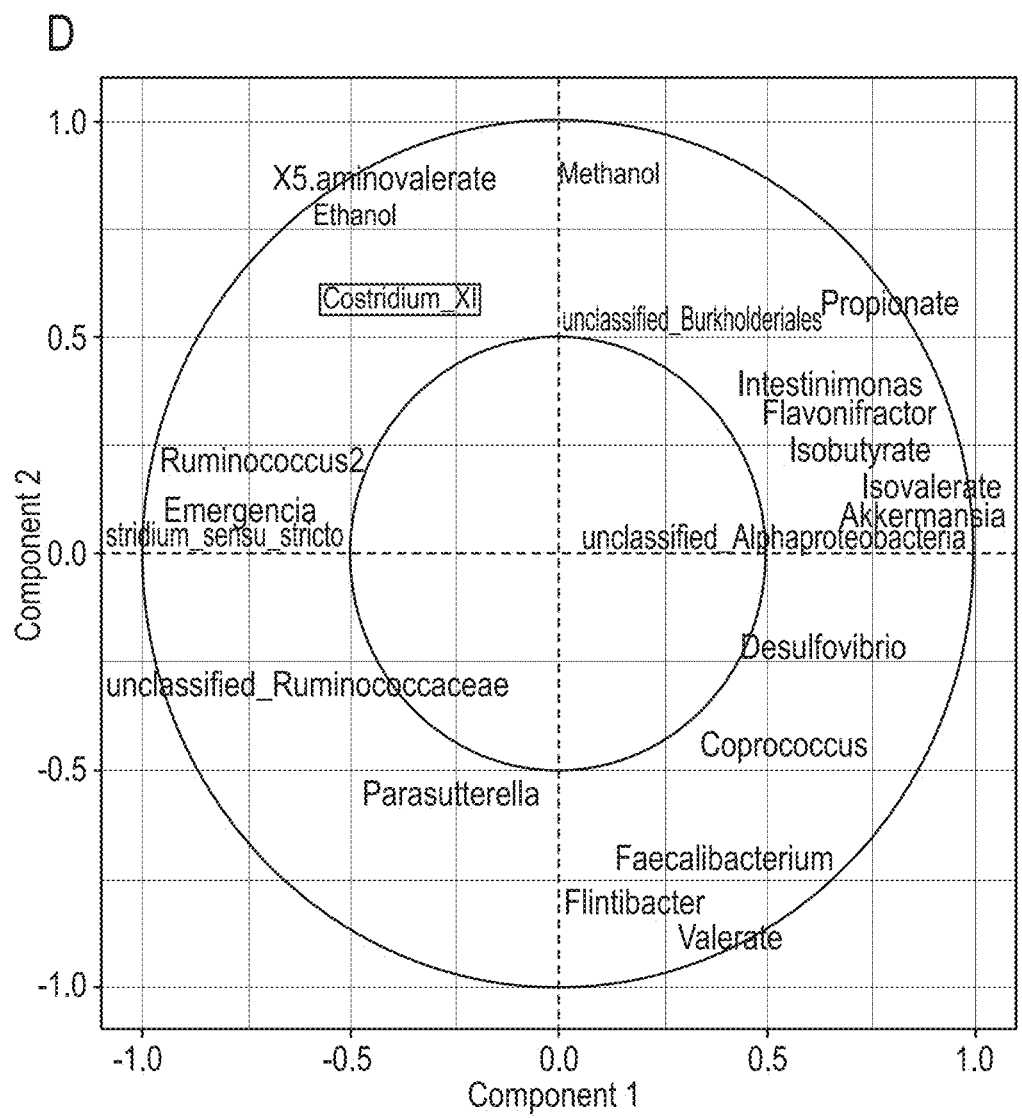

1H-Nmr Spectroscopy:

The inventors performed $^1$H-NMR spectroscopy as an exploratory technique to generate broad metabolite spectral profiles for samples collected over the course of the chemostat experiments. There was a significant decrease in valerate (p=0.004), butyrate (p=0.004), and acetate (p=0.013) and a significant increase in 5-aminovalerate (p=0.004), ethanol (p=0.021), succinate (p=0.004), and isobutyrate (p=0.004) during the clindamycin dosing period compared to the steady state period (FIGS. 3 and 8). rCCA modelling was used to determine correlations between 16S rRNA gene sequencing data and metabolite data that correspond to clindamycin dosing. The unit representation plot showed a clear separation between steady state cultures and cultures sampled during and after the clindamycin dosing period (FIG. 9a). The correlation circle plot showed that the separation between the cultures was due to decreases in the levels of valerate and acetate, and increases in the levels 5-aminovalerate, succinate, isobutyrate, and ethanol during and after the clindamycin dosing period (FIG. 9b). This plot also showed strong correlations between bacterial genera and these metabolites. During the clindamycin-dosing period there were significant correlations between C. difficile TVC and valerate (rS=−0.59, p=0.005), 5-aminovalerate (rS=0.54, p=0.010), and succinate (rS=−0.49, p=0.022). Following the end of the clindamycin-dosing period the levels of succinate, butyrate, acetate, and isobutyrate recovered to steady state levels (before clindamycin dosing), and these levels were not affected by FMT treatment (FIGS. 3 and 8). However, after stopping clindamycin dosing the levels of valerate (p=0.009) were still significantly decreased and the levels of 5-aminovalerate (p=0.009) and ethanol (p=0.013) were still significantly increased compared to the steady state period (FIG. 3), indicating the levels of these metabolites did not recover after stopping clindamycin dosing. Moreover, after stopping clindamycin dosing the levels of isovalerate decreased (p=0.009) and the levels of propionate increased (p=0.036) compared to the steady state period (FIGS. 3 and 8).

There was a significant increase in valerate (p=0.032), and significant decreases in 5-aminovalerate (p=0.032), ethanol (p=0.032), propionate (p=0.032), and methanol (p=0.039) in FMT-treated cultures compared to saline-treated cultures (FIG. 3). rCCA modelling was also used to determine correlations between 16S rRNA gene sequencing data and metabolite data that correspond to FMT or saline treatment. The unit representation plot showed a clear separation between FMT-treated cultures and saline-treated cultures along the second canonical variate (FIG. 9c). The correlation circle plot showed that the separation between FMT- and saline-treated cultures was due to increases in the levels of valerate and decreases in the levels of 5-aminovalerate, ethanol, and methanol in FMT-treated cultures (FIG. 9d). This plot also showed strong correlations between bacterial genera and these metabolites. Following FMT or saline treatment there was a significant strong negative correlation between C. difficile TVC and valerate (rS=−0.67, p=1.48× 10−4), and significant strong positive correlations between C. difficile TVC and 5-aminovalerate (rS=0.76, p=60.7×10− 6), ethanol (rS=0.81, p=1.72×10−6), and methanol (rS=0.72, p=2.98×10−5).

Figure 10:
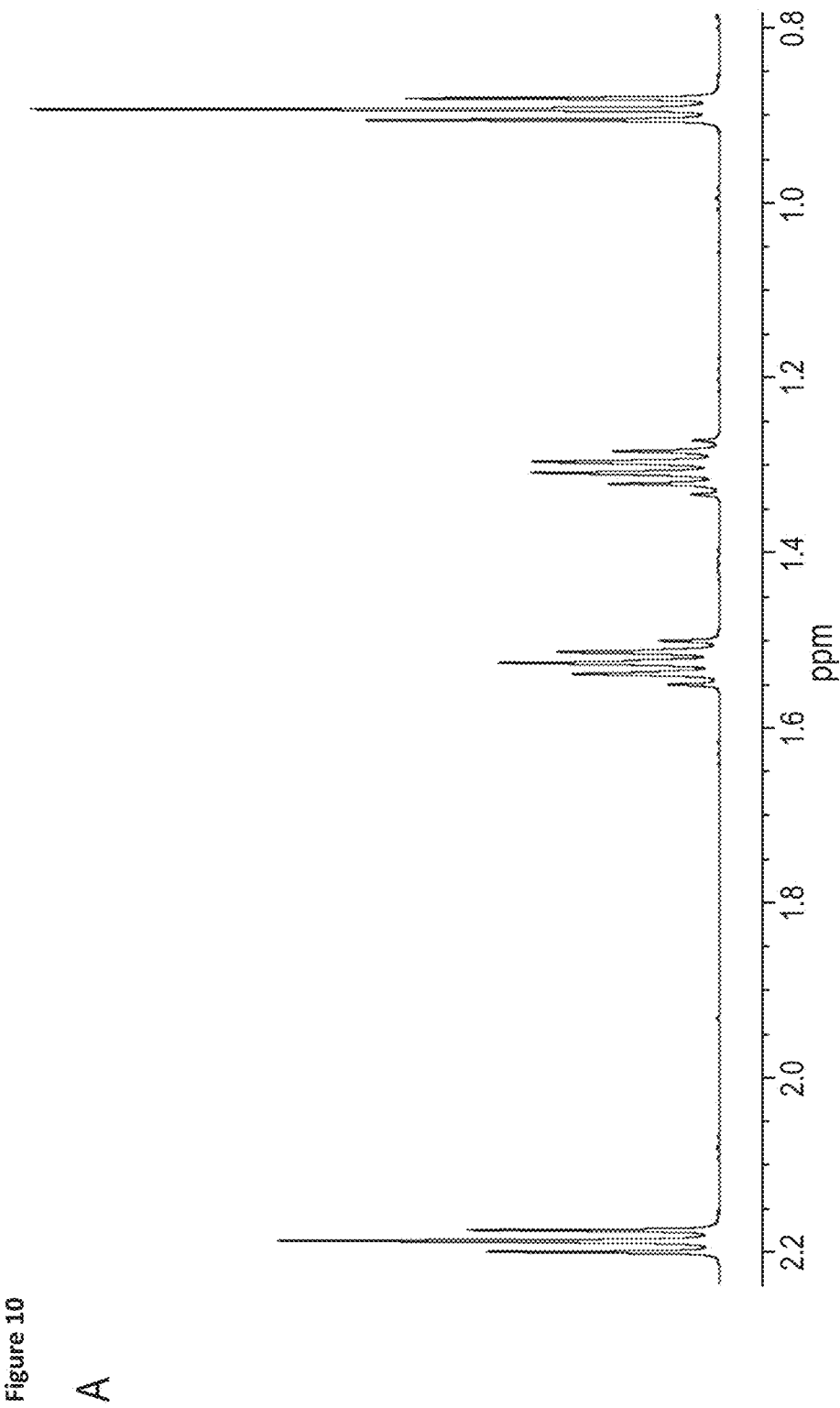
Figure 10:
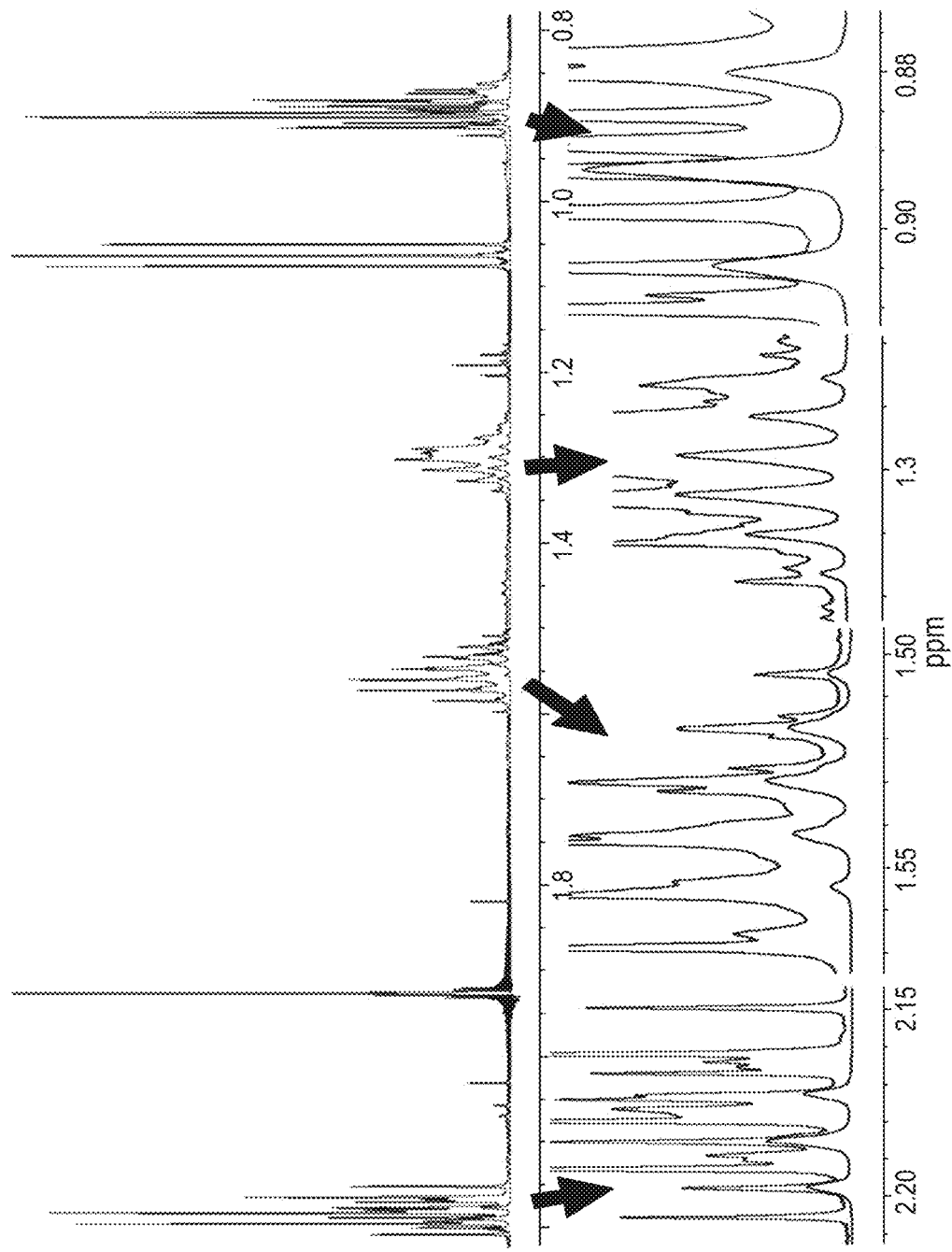
Figure 10:
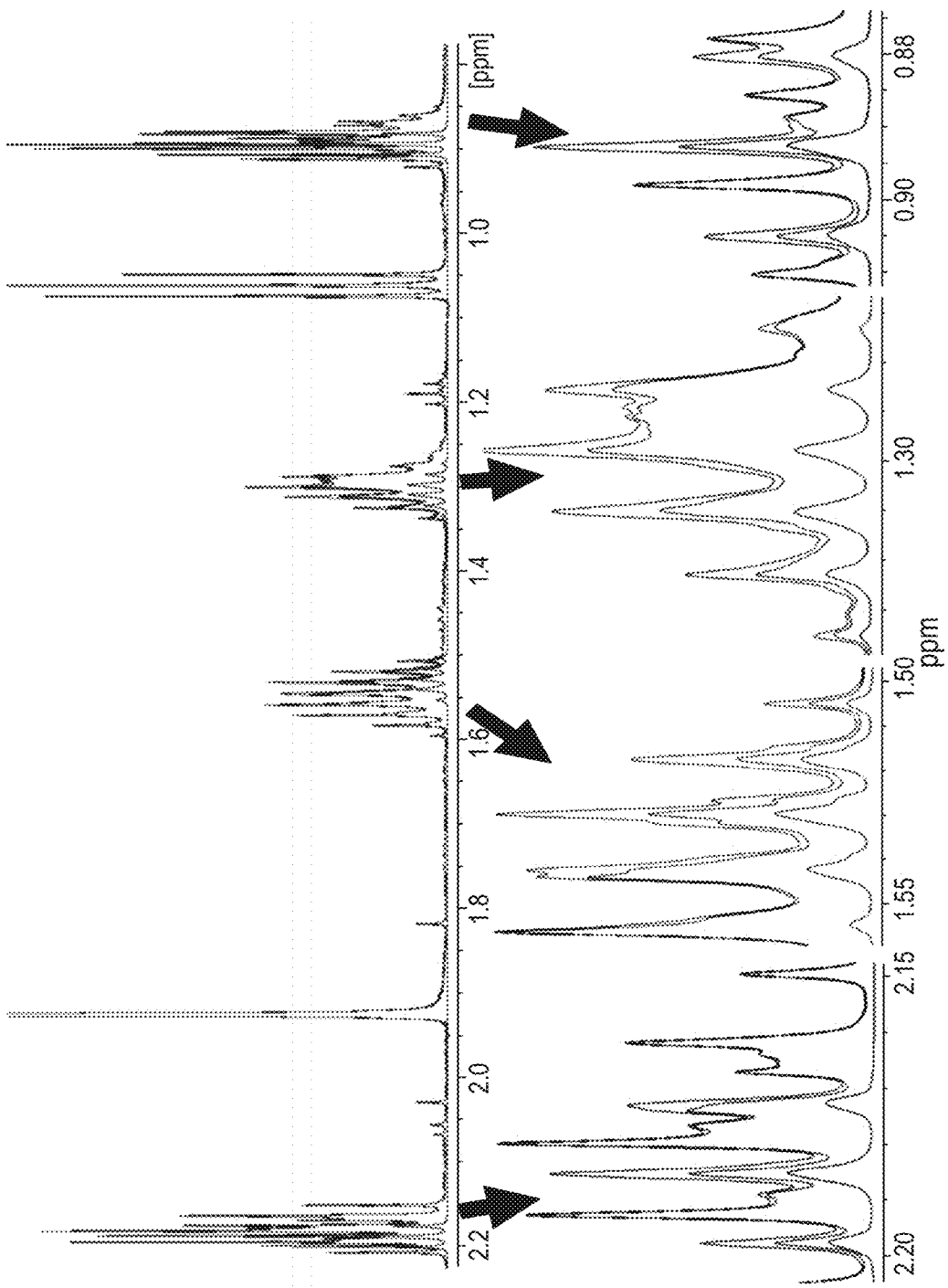
Figure 11:
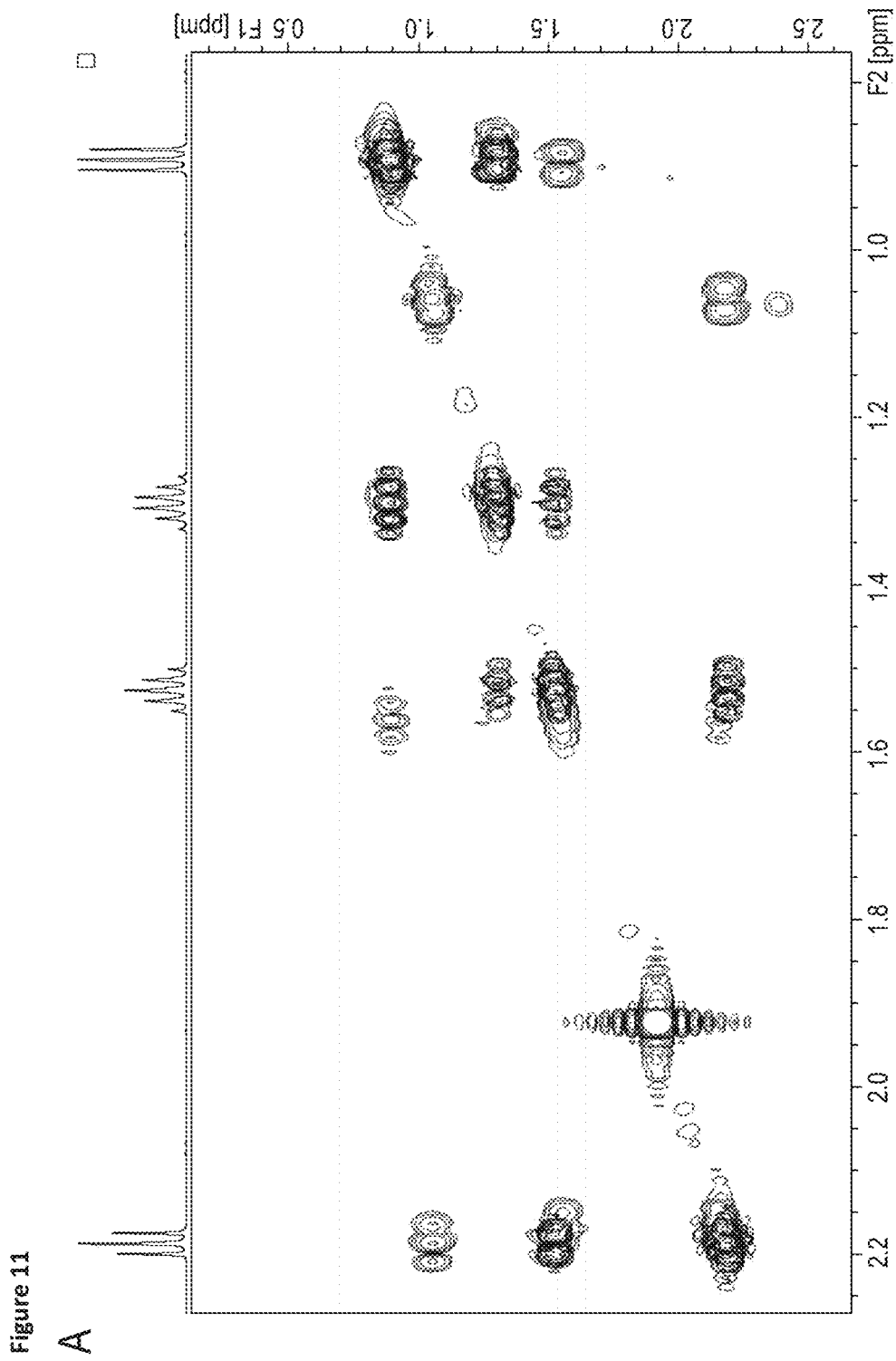
Figure 11:
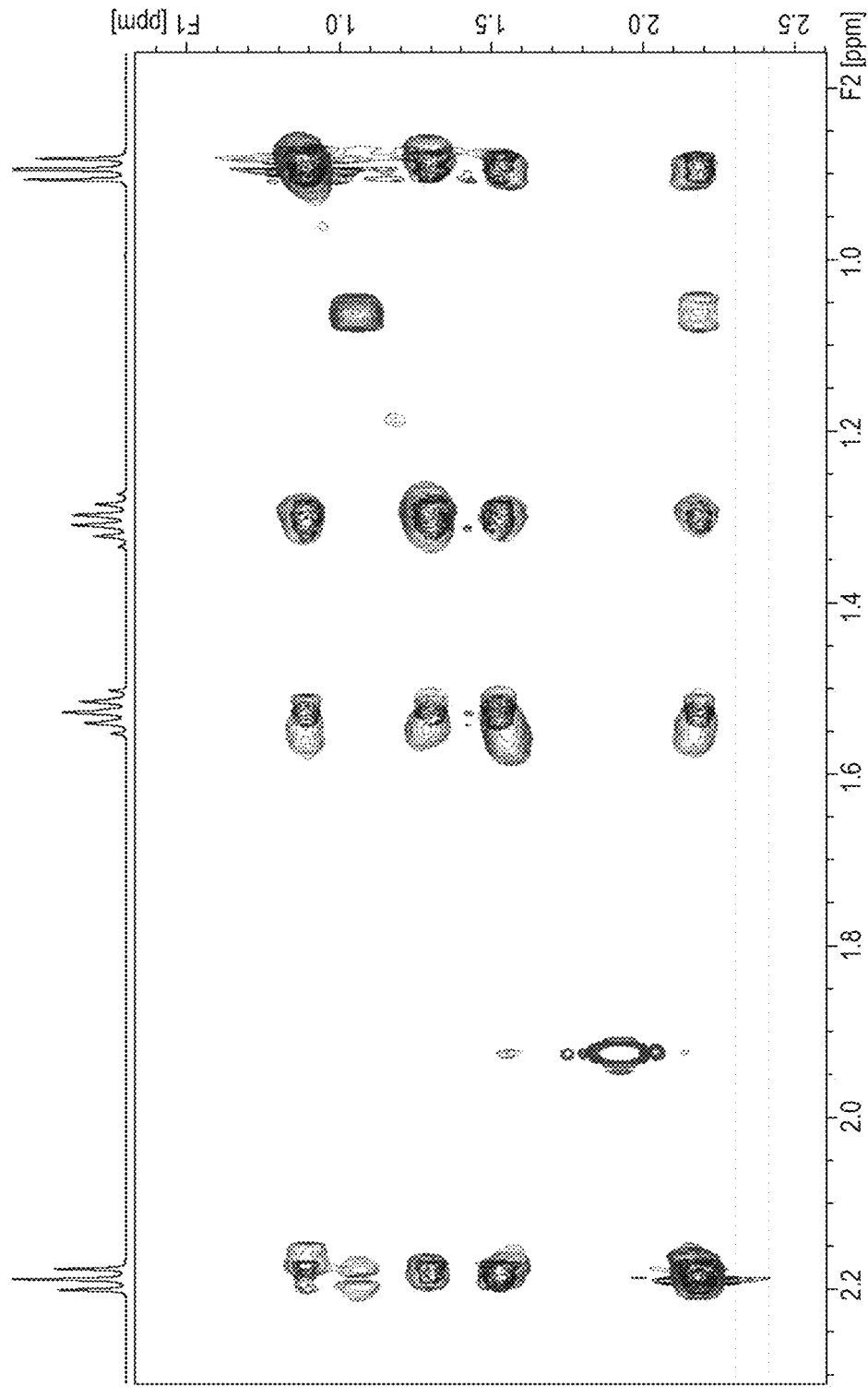
Figure 12:
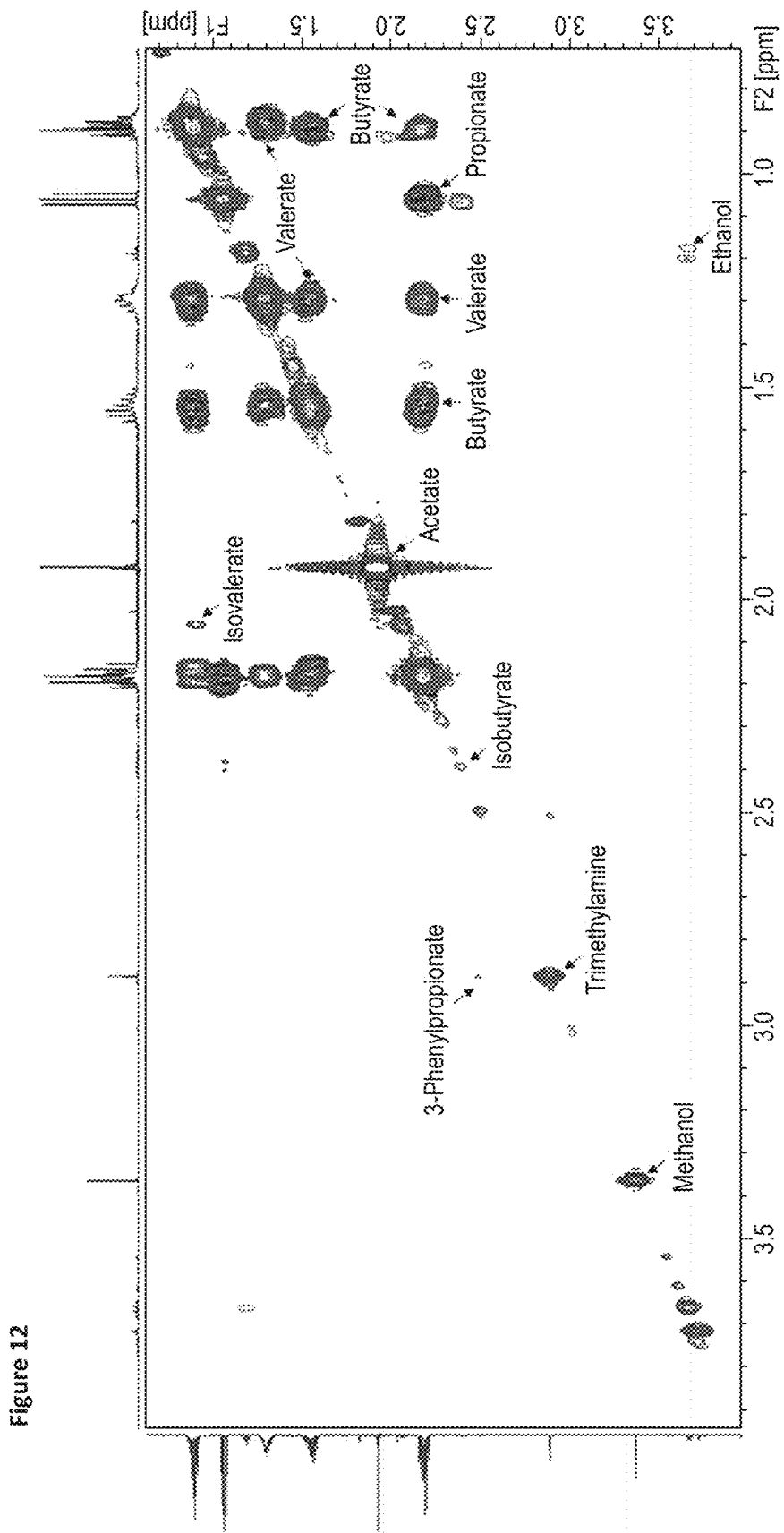
Figure 12:
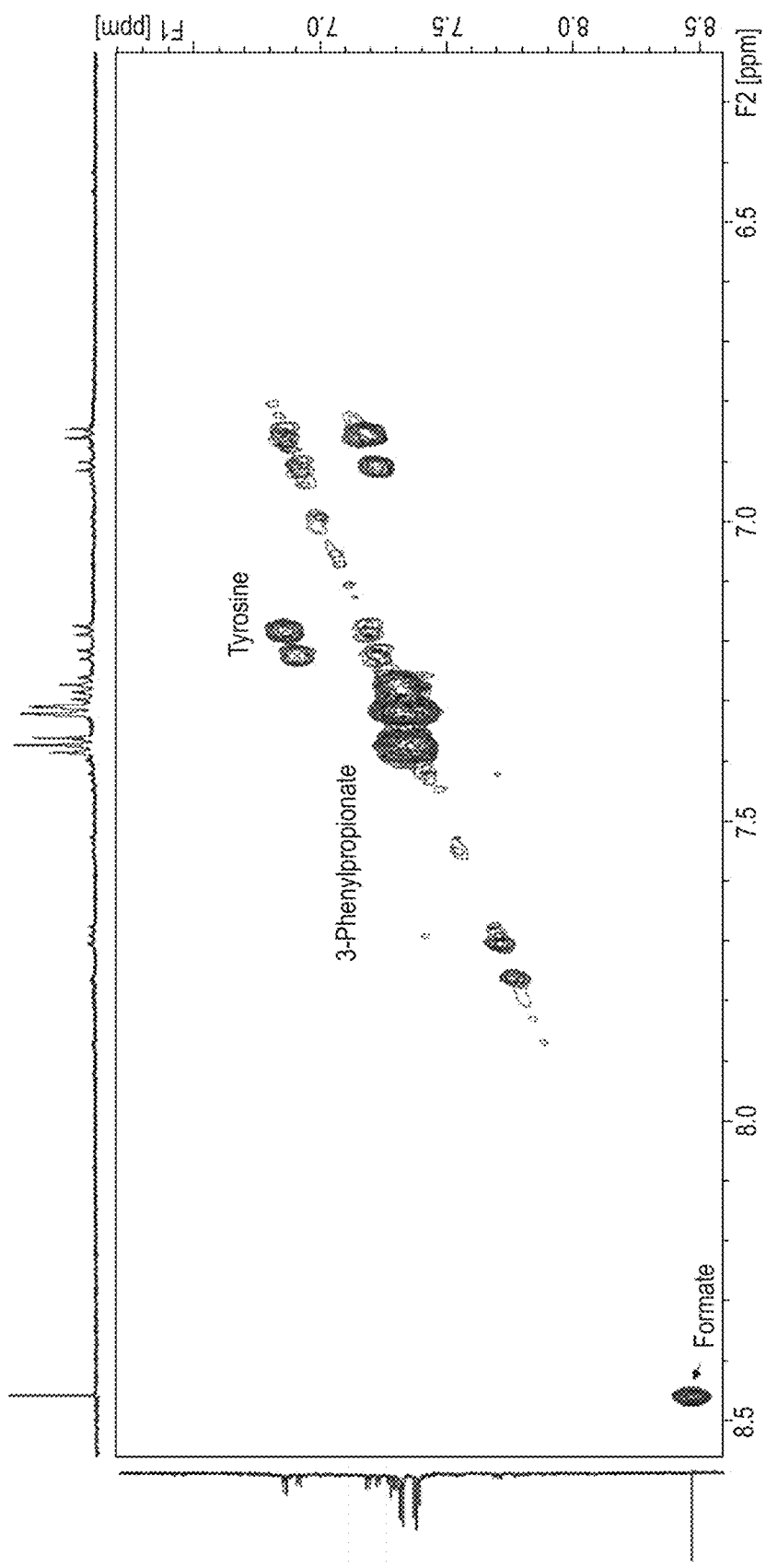
Figure 13:
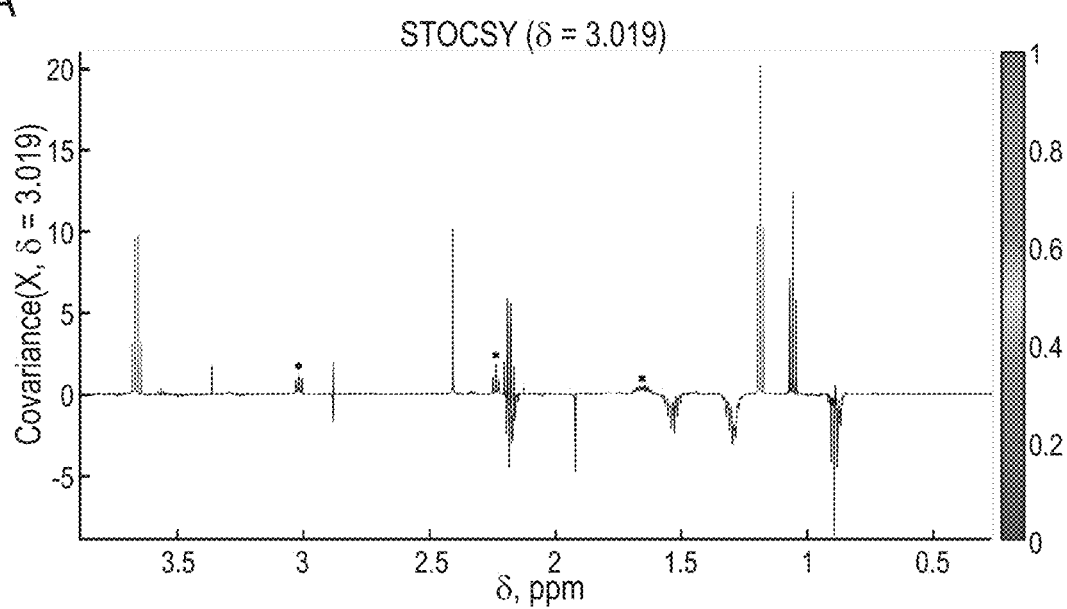
Figure 13:
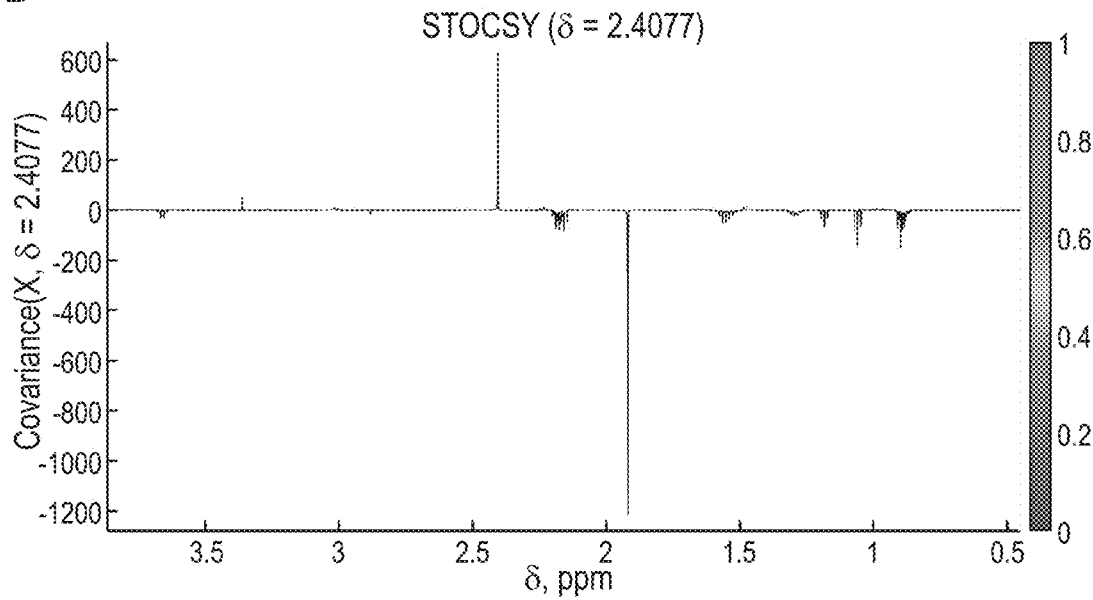

The inventors confirmed the identity of the proposed valerate peaks in the chemostat culture supernatants by performing 1D-NMR spectroscopy of a sample before and after valerate spike-in as well as 2D-NMR spectroscopy of a valerate-containing sample (FIGS. 10 and 11). They also confirmed the identity of other metabolites by 2D-NMR and STOCSY (FIGS. 12 and 13).

Bile Acid UPLC-MS Profiling:

Due to the important role that bile acids play in C. difficile spore germination,[5] the inventors also measured changes in bile acids over the course of the chemostat experiments.

Figure 4:
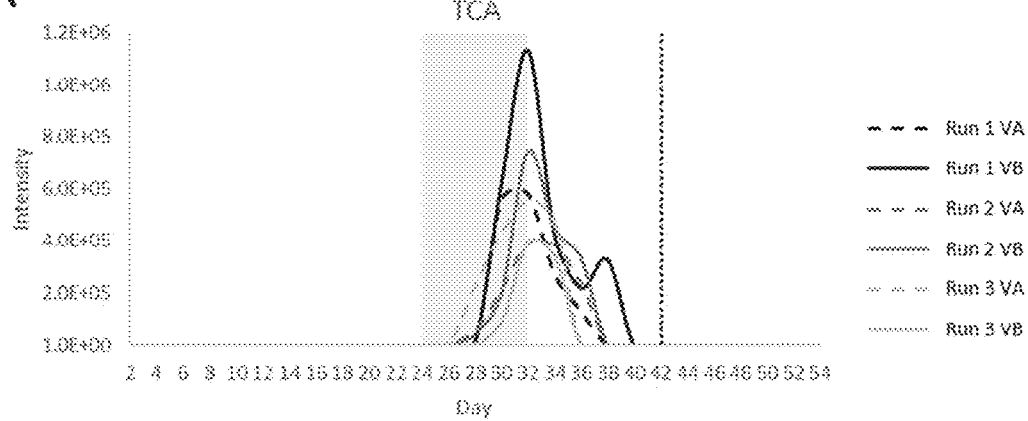
Figure 4:
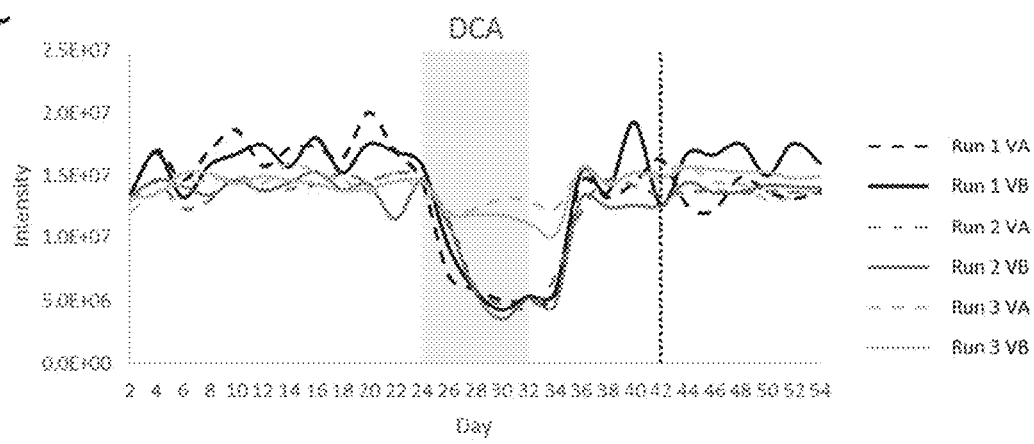
Figure 4:
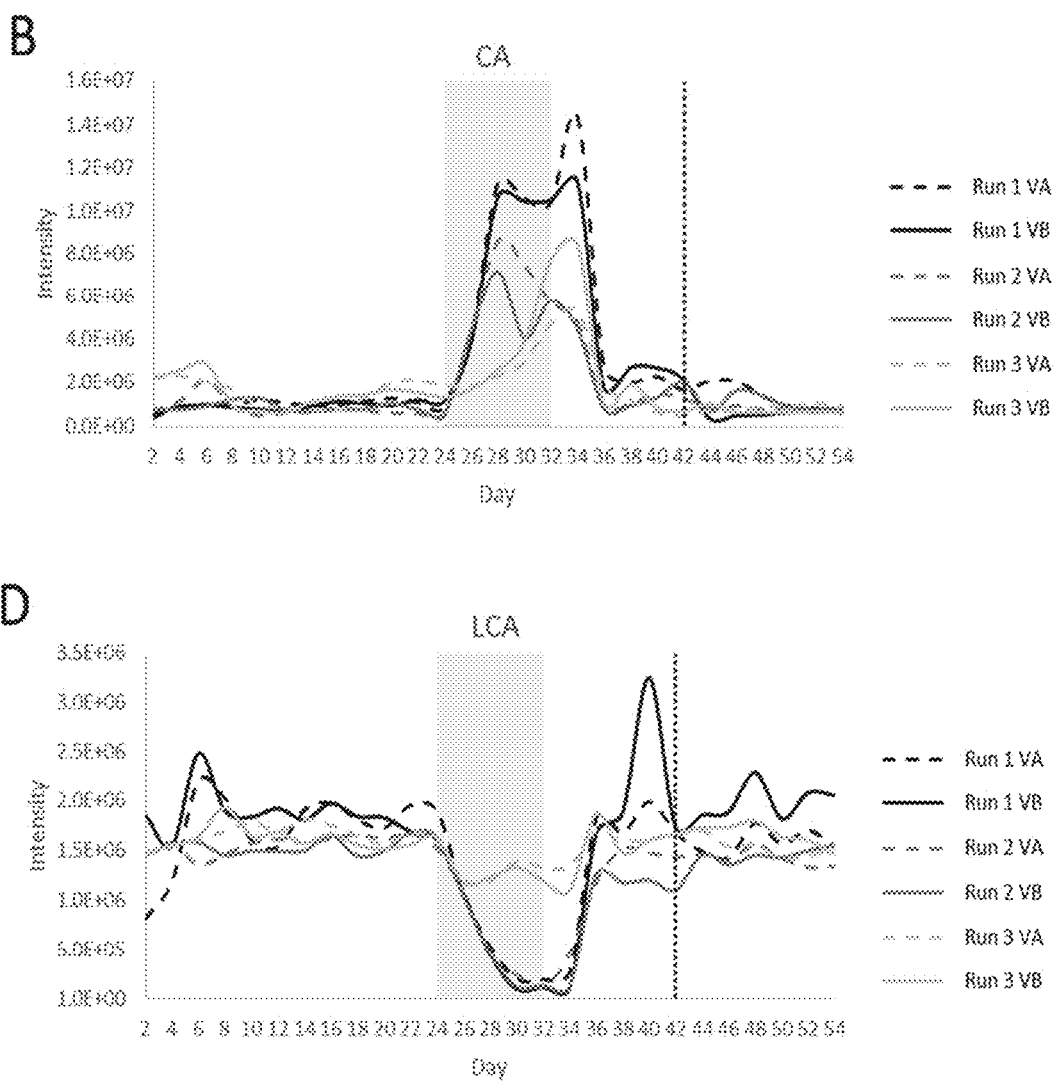
Figure 14:
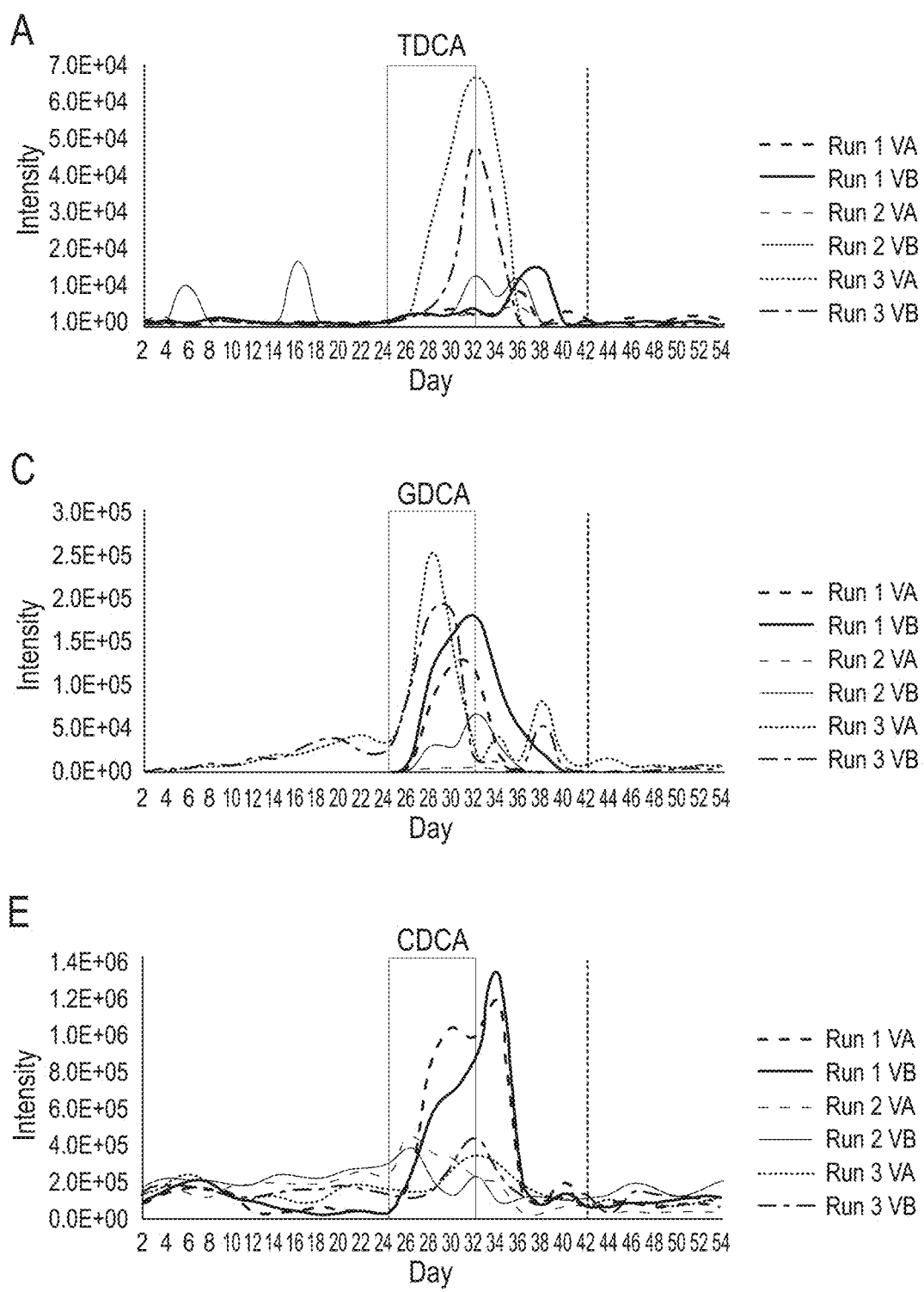
Figure 14:
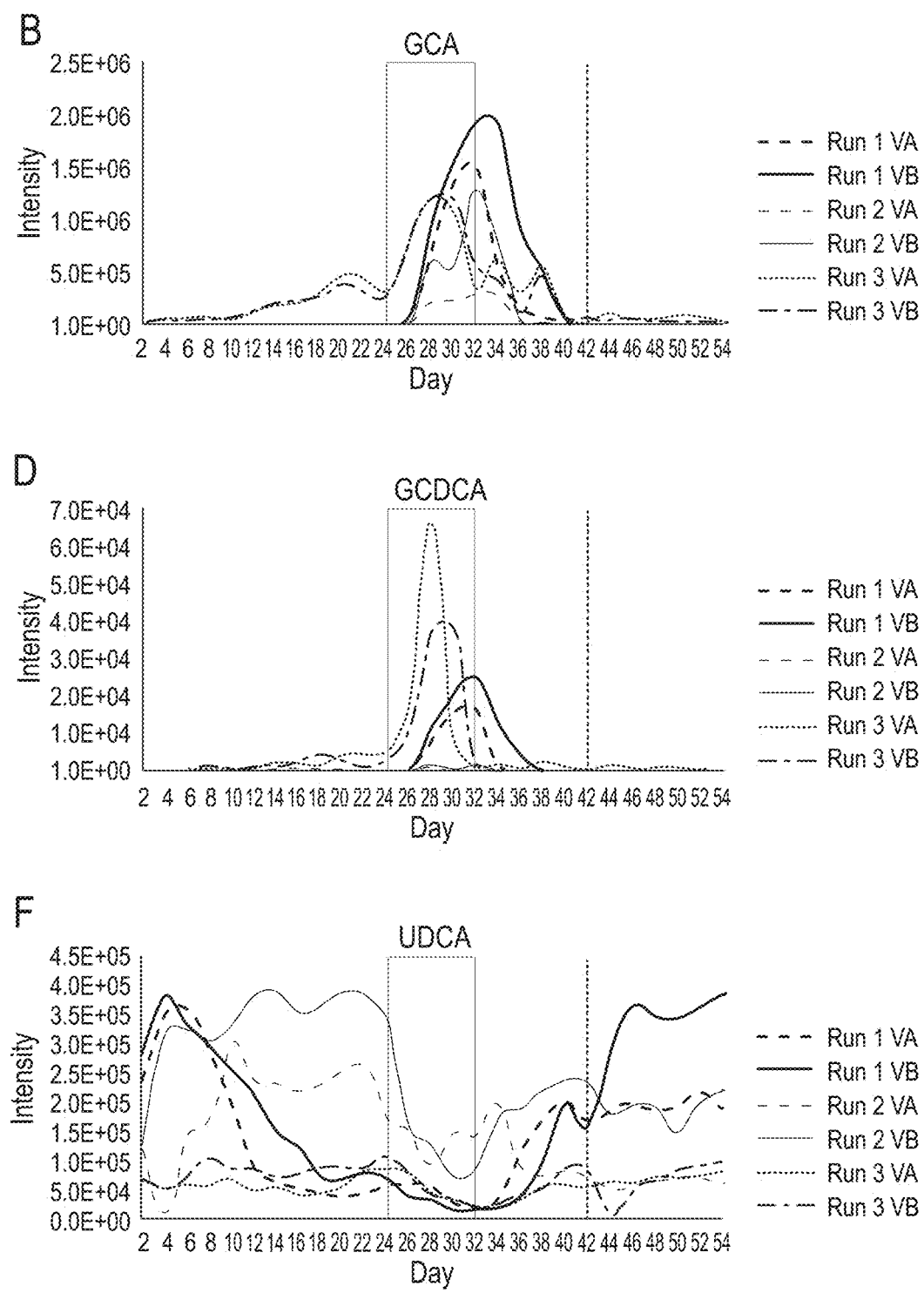
Figure 15:
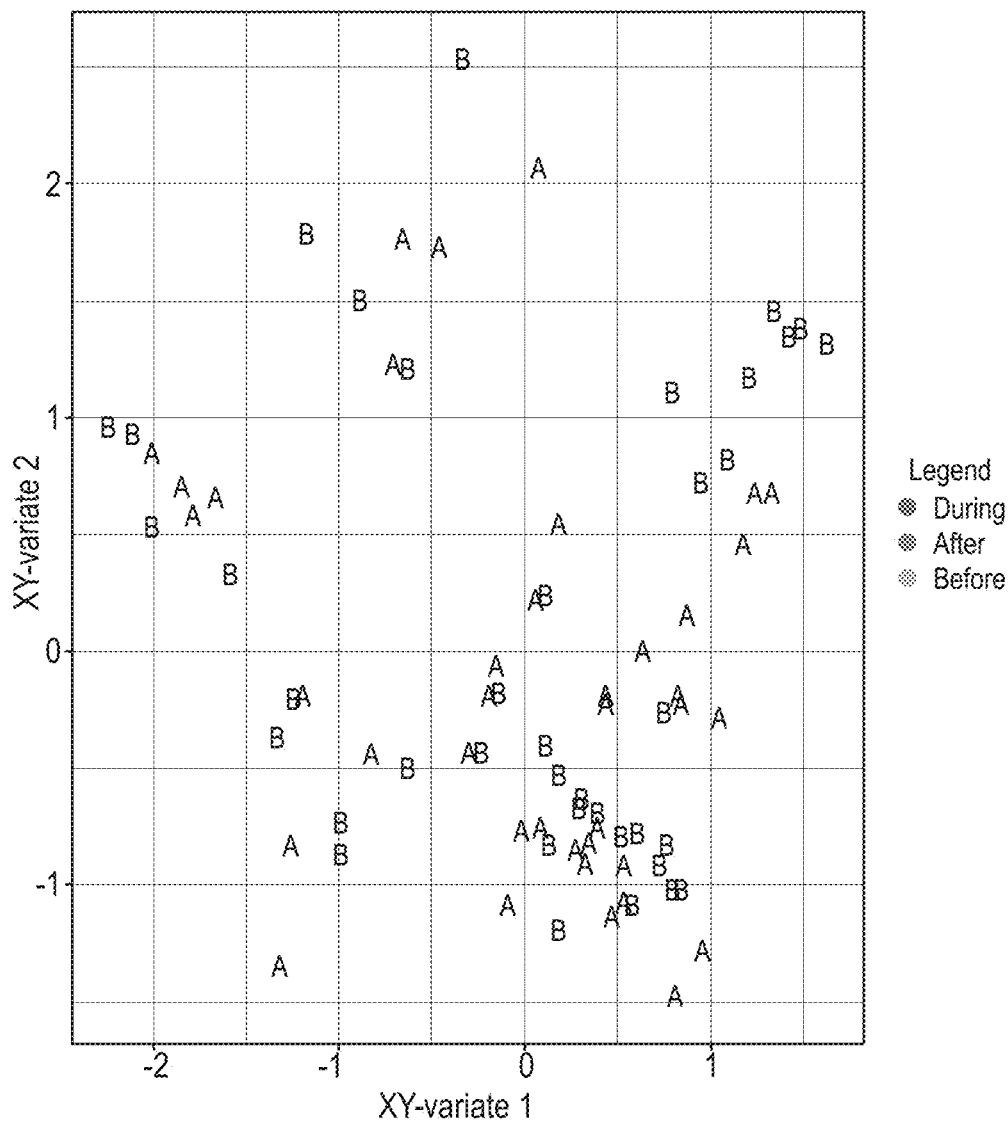
Figure 15:
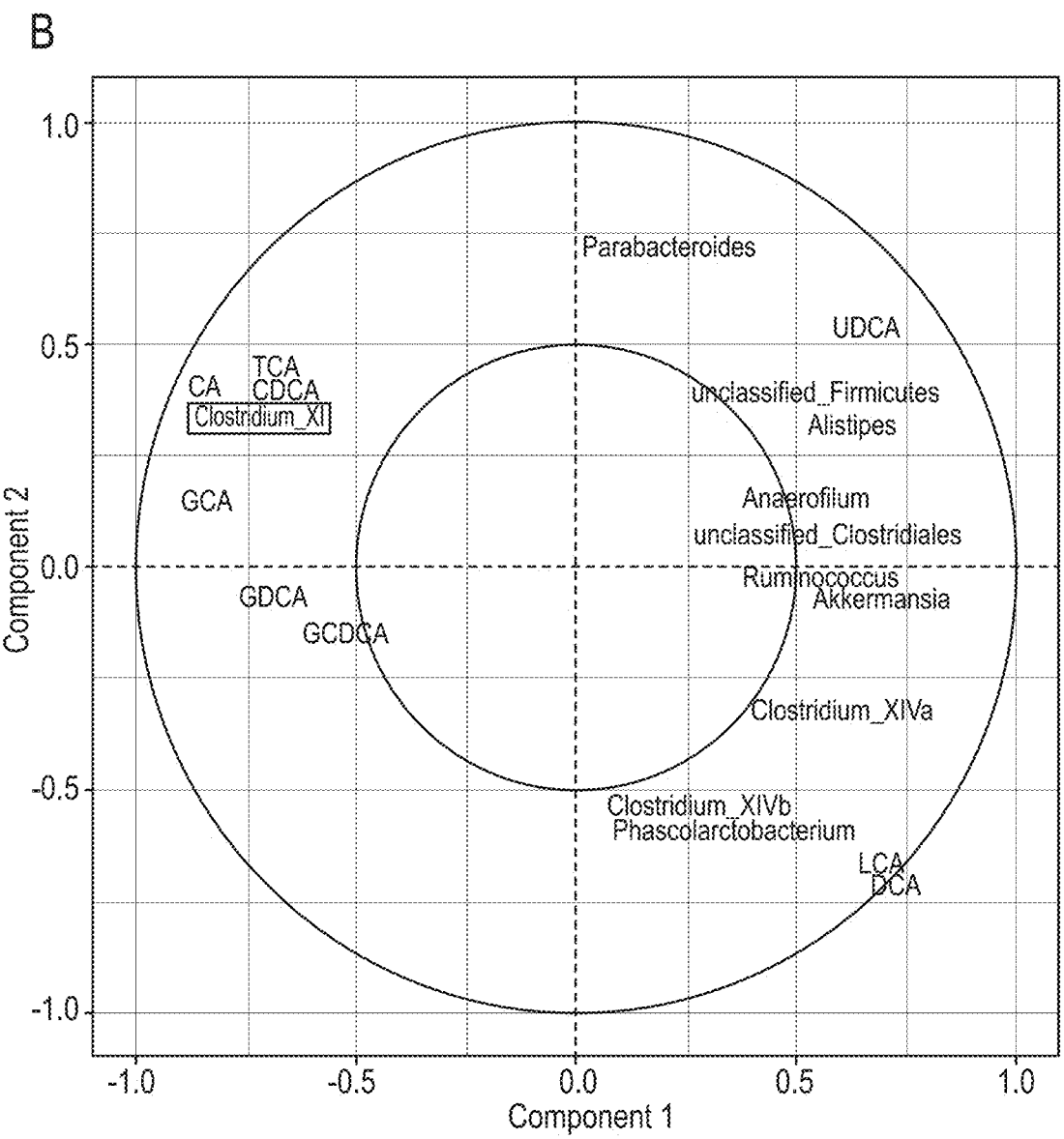

There was a significant increase in conjugated and unconjugated primary bile acids, including taurocholic acid (TCA) (p=0.004), taurodeoxycholic acid (TDCA) (p=0.045), glycocholic acid (GCA) (p=0.005), glycodeoxycholic acid (GDCA) (p=0.004), glycochenodeoxycholic acid (GCDCA) (p=0.005), cholic acid (CA) (p=0.004), and chenodeoxycholic acid (CDCA) (p=0.037). There was also a significant decrease in the secondary bile acids deoxycholic acid (DCA) (p=0.006), lithocholic acid (LCA) (p=0.005), and ursodeoxycholic acid (UDCA) (p=0.037) during the clindamycin-dosing period compared to the steady state period (FIGS. 4 and 14). Following the end of the clindamycin dosing period the levels of these bile acids recovered to steady state levels (before clindamycin dosing), and these levels were not affected by FMT treatment.

rCCA modelling was used to determine correlations between 16S rRNA gene sequencing data and bile acid data during the clindamycin-dosing period. The unit representation plot showed separation between cultures sampled before and during the clindamycin-dosing period along the first canonical variate, but no separation between cultures sampled before and after the clindamycin-dosing period (FIG. 15a). The correlation circle plot showed that the separation between cultures sampled before and during clindamycin dosing was due to increases in the levels of TCA, CA, CDCA, GCA, GDCA, and GCDCA, and decreases in the levels of DCA, LCA, and UDCA during the clindamycin-dosing period (FIG. 15b). This plot also showed strong correlations between bacterial genera and bile acids.

There were significant strong correlations between *C. difficile* TVC and several bile acids during the clindamycin dosing period, including TCA (rS=0.68, p=6.29×10−4), CA (rS=0.61, p=0.003), DCA (rS=−0.75, p=8.86×10−5), and LCA (rS=−0.76, p=6.36×10−5).

Figure 5:
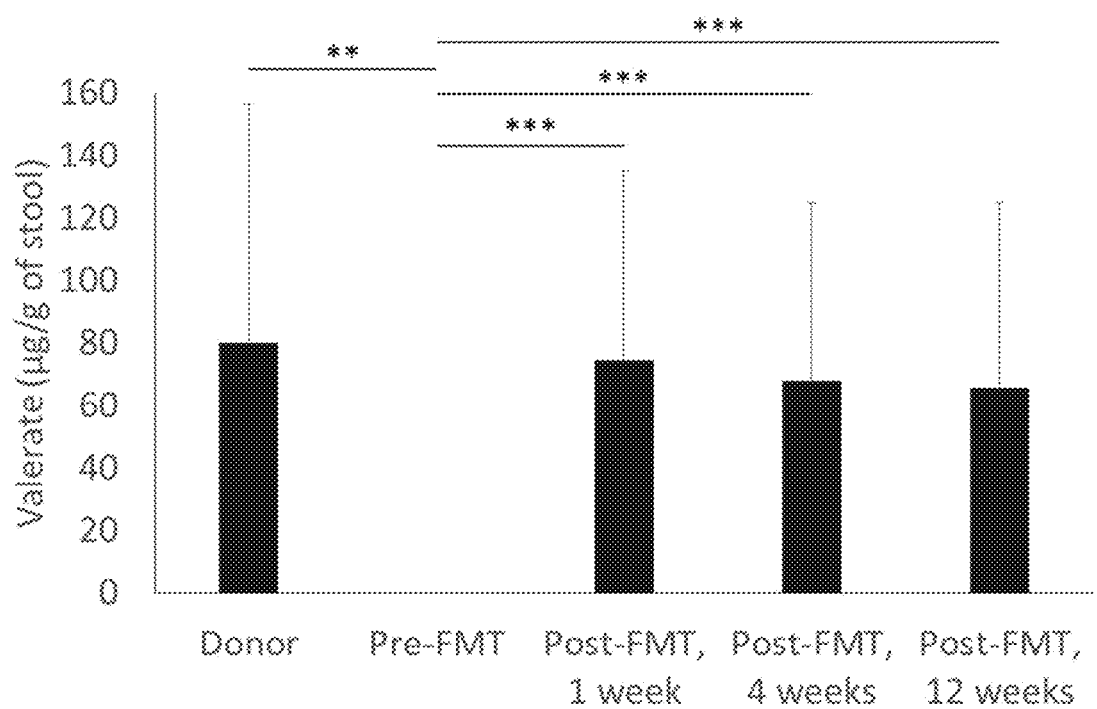

GC-MS of Human Stool Samples:

To confirm the findings from the inventor's chemostat experiments they measured the levels of valerate in human stool samples from healthy FMT donors, recurrent CDI patients pre-FMT and at several time points post-FMT (1, 4, and 12 weeks after FMT treatment) (FIG. 5). Valerate was depleted in stool samples from recurrent CDI patients pre-FMT compared to healthy donors (p=0.0075). Valerate levels were significantly increased in CDI patients post-FMT compared to pre-FMT (p=0.00007 at 1 week, 4 weeks, and 12 weeks). There were no significant differences in the levels of valerate in stool samples from healthy donors compared to any of the time points from CDI patients collected post-FMT (p>0.05 for all comparisons).

Figure 6:
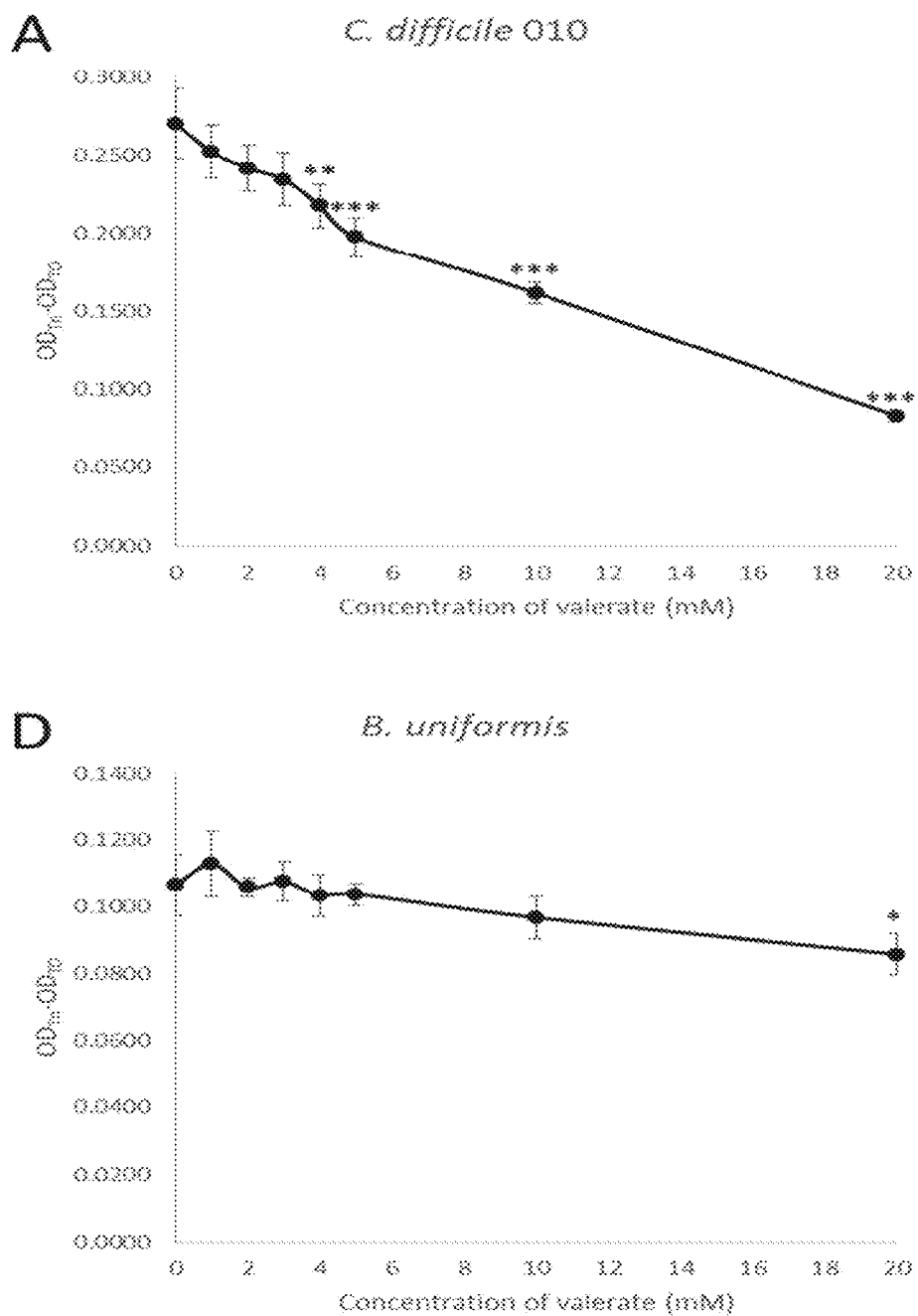
Figure 6:
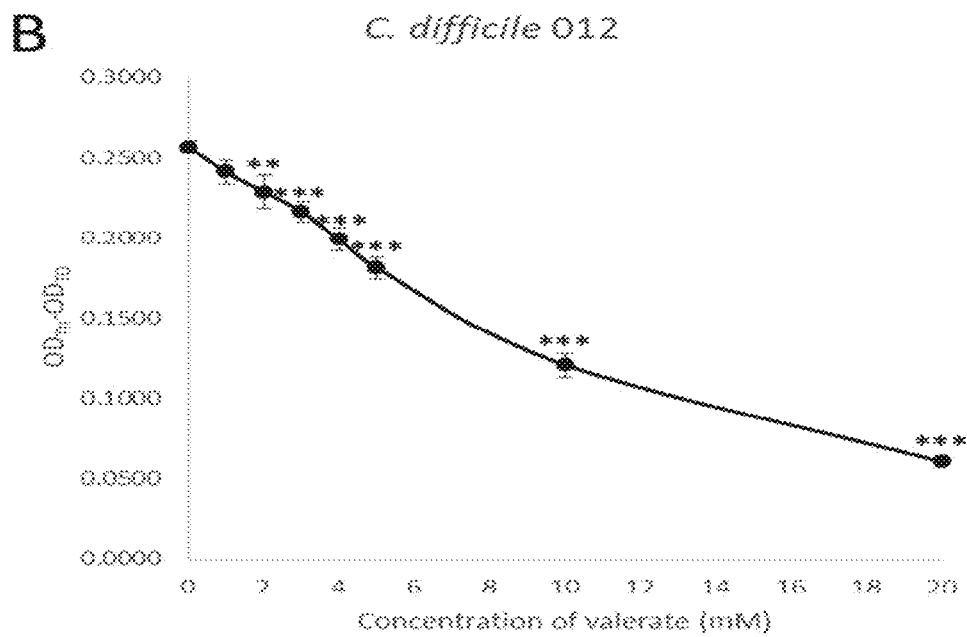
Figure 6:
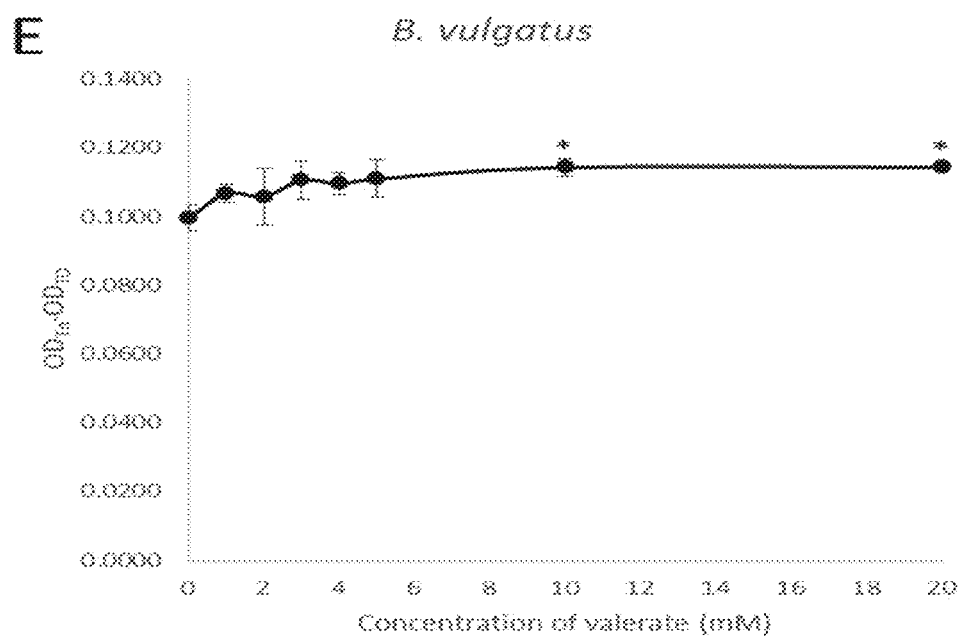
Figure 6:
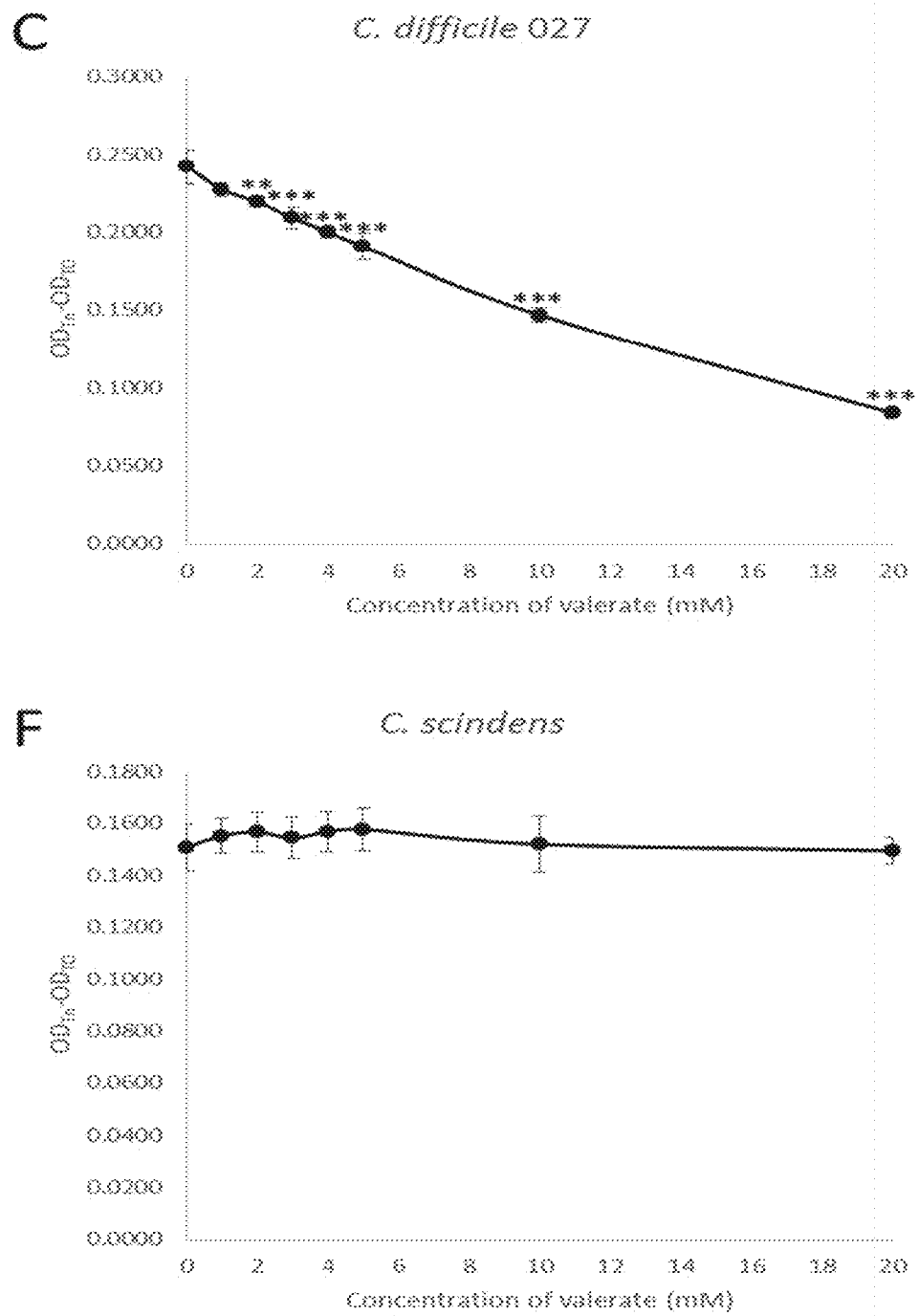

*C. difficile* Batch Culture Experiments with Valerate and TCA:

Batch culture experiments were performed to directly study the effects of specific metabolites of interest on *C. difficile* germination and vegetative growth and to confirm the findings from the inventor's chemostat experiments. These experiments showed that valerate inhibited the vegetative growth *C. difficile* ribotype 010 at concentrations 4 mM (p=0.008), ribotype 012 at concentrations 2 mM (p=0.003), and ribotype 027 at concentrations 2 mM (p=0.008) (FIG. 6). The concentration of valerate in FMT-treated chemostat culture supernatants remained above 4 mM for all samples, whereas the concentration of valerate in saline-treated cultures remained below 2 mM for all samples. As a control, the inventors also tested the effects of valerate on commensal gut isolates (*Bacteroides uniformis* and *Bacteroides vulgatus*, two representatives of *Bacteroidetes*, and *Clostridium scindens*, a representative of *Firmicutes*). *B. uniformis* was only inhibited in broth containing 20 mM valerate (p=0.026). *B. vulgatus* was not inhibited at any concentration of valerate that was tested, and grew better in broths containing 10 mM (p=0.020) or 20 mM (p=0.019) valerate. *C. scindens* was not inhibited at any concentration of valerate tested (p>0.05 for all concentrations of valerate tested).

Figure 16:
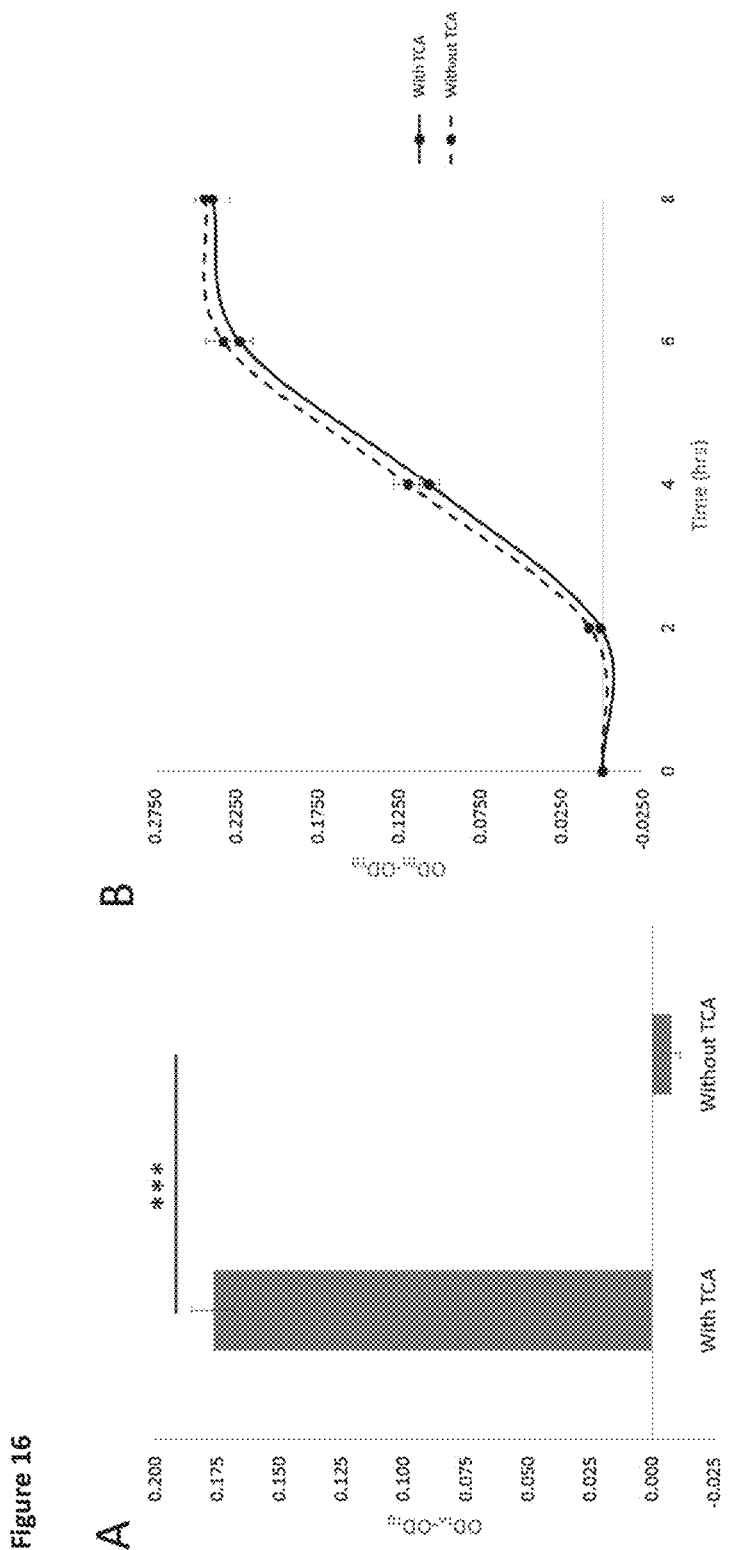

Batch culture experiments also confirmed previous findings showing that TCA is required for *C. difficile* spore germination but had no effect on vegetative growth (FIG. 16).

*C. difficile* Total Viable Counts and Spore Counts

There was no significant difference in *C. difficile* TVC at the end of the clindamycin-dosing period compared to TVC immediately prior to administering FMT or saline treatment (p>0.05). There was also no significant difference in *C. difficile* TVC in vessels assigned to receive FMT or saline treatment immediately prior to administering the treatment (p>0.05).

$^1$H-NMR Spectroscopy

Following FMT or saline treatment there were significant strong negative correlations between valerate and 5-aminovalerate ($r_S$=−0.76, p=5.27×10$^{-6}$), ethanol ($r_S$=−0.69, p=6.53×10−5), and methanol ($r_S$=−0.78, p=3.11×10$^{-6}$).

Confirmation of Valerate in Chemostat Culture Supernatant by 1D- and 2D-NMR

The chemical shifts for the 1D $^1$H-NMR spectrum of 99% valerate standard were: 0.9 (t), 1.3 (dt), 1.46 (m), 2.2 (t) (FIG. 11). Overlay of the 1D $^1$H-NMR spectrum of the valerate standard with the sample showed that each peak of the valerate standard is visible in the sample (FIG. 10). Overlay of 1D $^1$H-NMR spectra of the sample before and after valerate spike-in showed that all the valerate peaks increased after spike-in (FIG. 10). For 2D-NMR analysis overlay of the $^1$H-$^1$H COSY spectrum of the valerate standard with the sample showed that each peak of the valerate standard was present in the sample spectrum (FIG. 11a). Overlay of $^1$H-$^1$H TOCSY spectrum of the valerate standard with the sample showed that each peak of the valerate standard was present in the sample spectrum (FIG. 11b).

Figure 17:
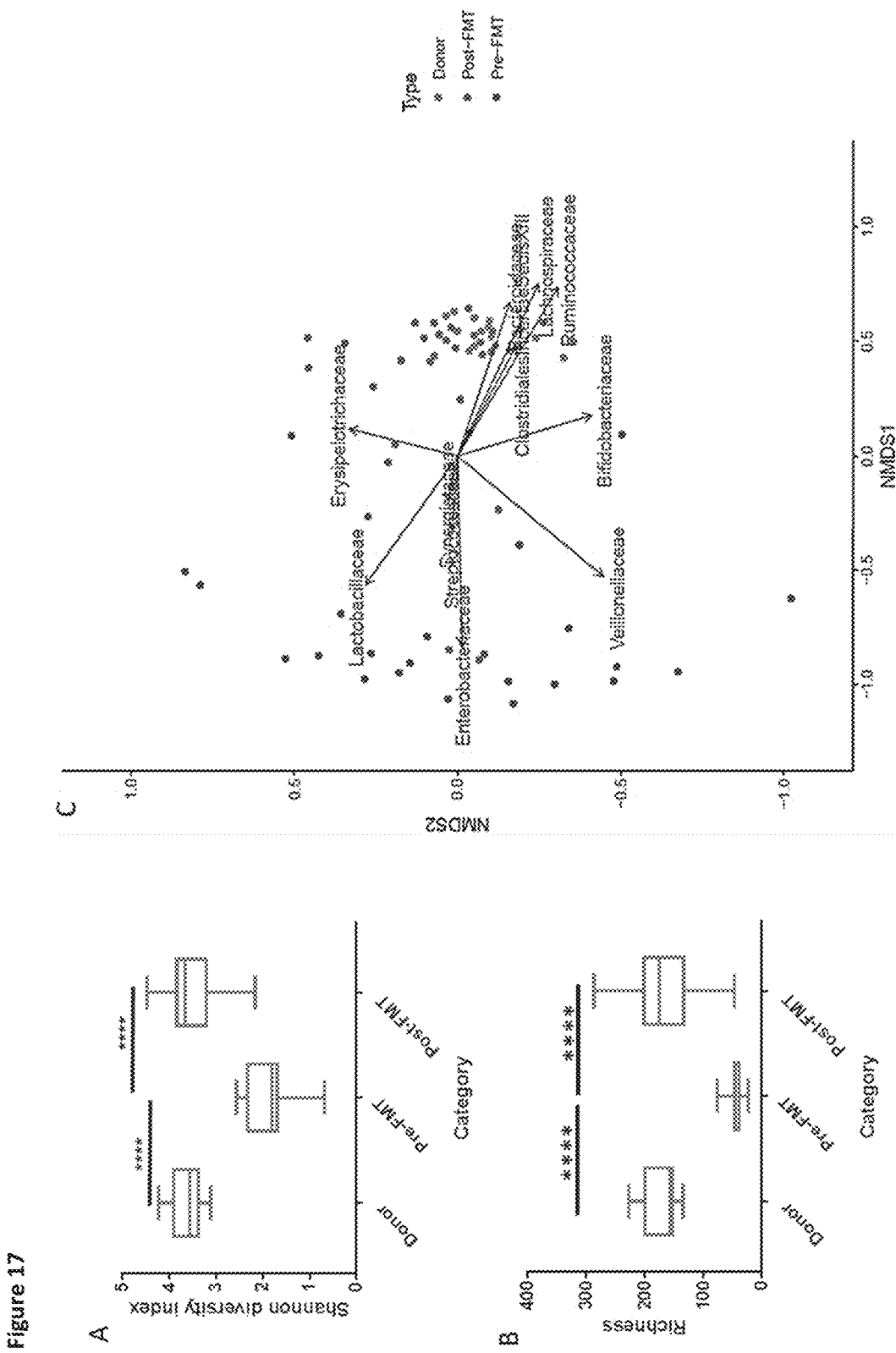
Figure 24:
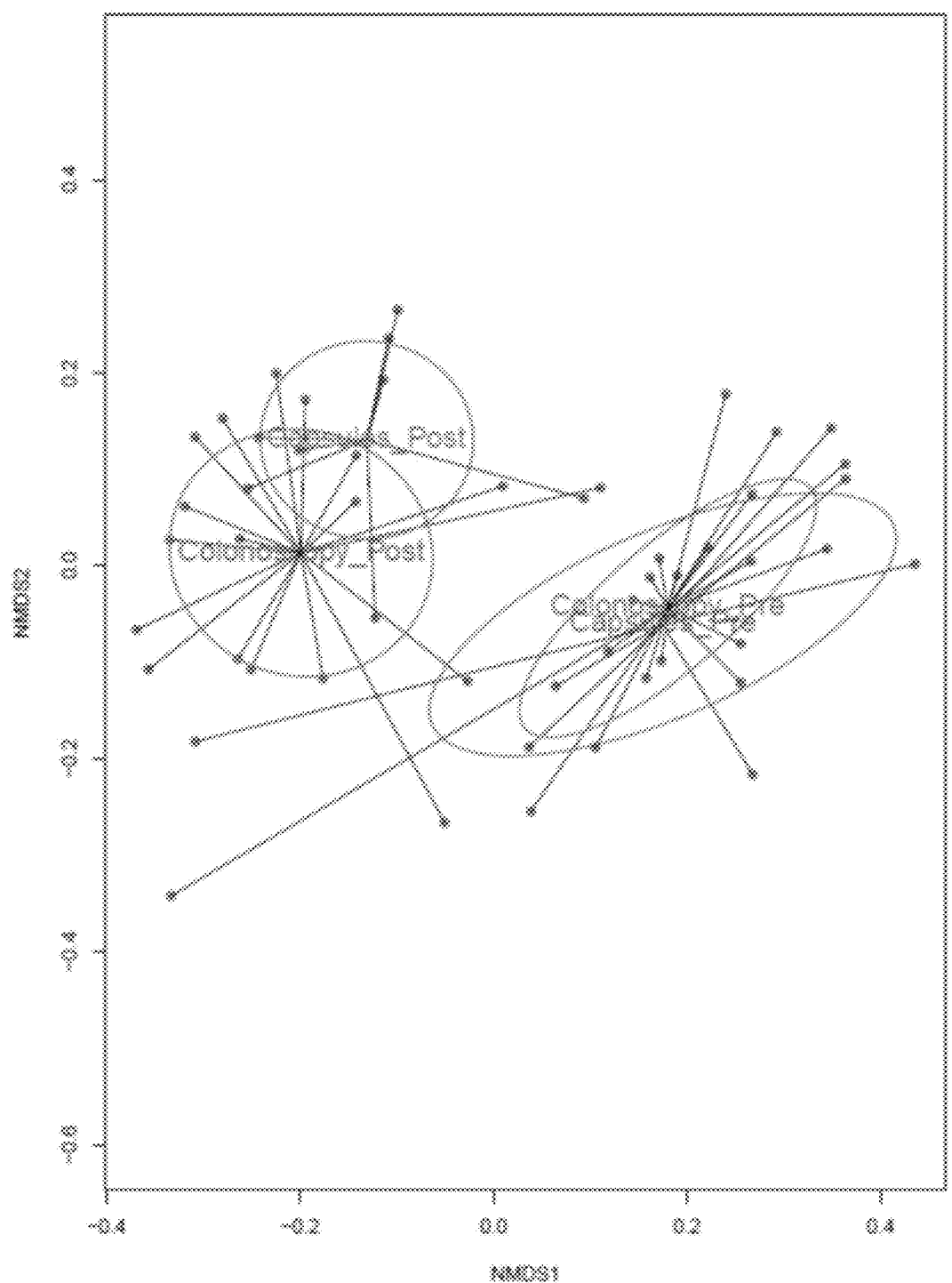
Figure 25:
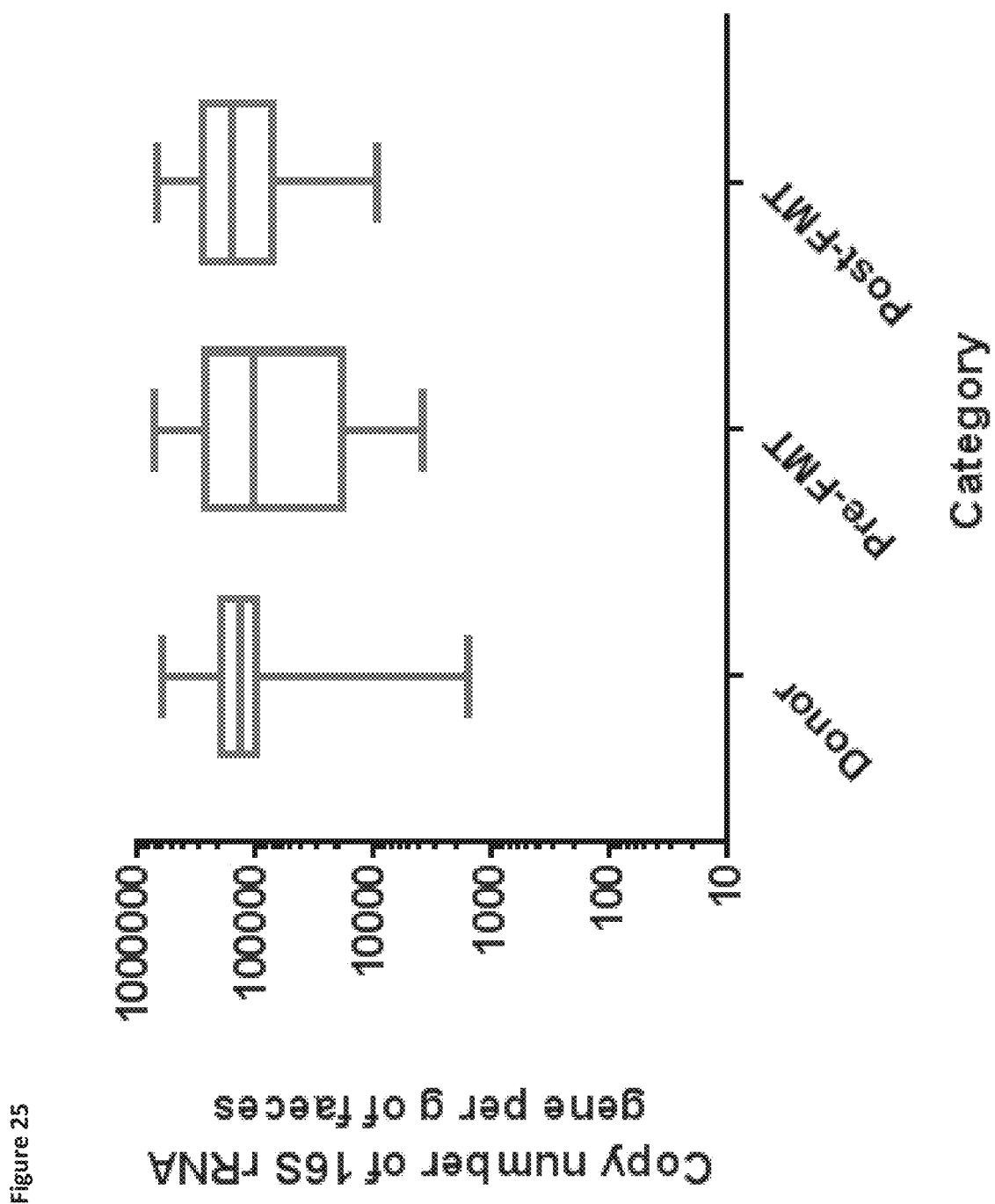

The following discussion relates to those results obtained from the human study.

rCDI is Associated with Loss of Bile-Metabolising Gut Microbiota Members, and FMT Restores BSH-Producing Organisms:

Stool from patients with rCDI demonstrated a significantly reduced a-diversity (as assessed by Shannon diversity index, p<0.001, Mann-Whitney, FIG. 17A), significantly reduced richness ($S_{obs}$, p<0.0001, FIG. 17B), and profoundly altered microbial community structure (as measured by NMDS, p<0.001, PERMANOVA, FIG. 17c) as compared to healthy donors. Successful FMT was associated with restoration of all these measures to values commensurate with that of the healthy donors. All samples were inseparable by microbial community structure pre-FMT and subsequently post-FMT, regardless of whether colonoscopy or capsule administration was used (p=0.288, PERMANOVA, FIG. 24).

rCDI patients had lower relative abundances of Lachnospiraceae, Ruminococcaceae, and Bacteroidaceae, and higher relative abundances of Enterobacteriaceae, Lactobacillaceae and Veillonellaceae compared to healthy donors (p<0.01 in all cases, Whites' non-parametric t-test with Benjamini-Hochberg correction, FIG. 17C). These families were all found at similar relative abundances in post-FMT and healthy donor samples. No significant difference in bacterial load (as assessed by 16S rRNA gene copy number) was observed between pre-FMT, post-FMT and donor groups (FIG. 25.

Figure 23A:
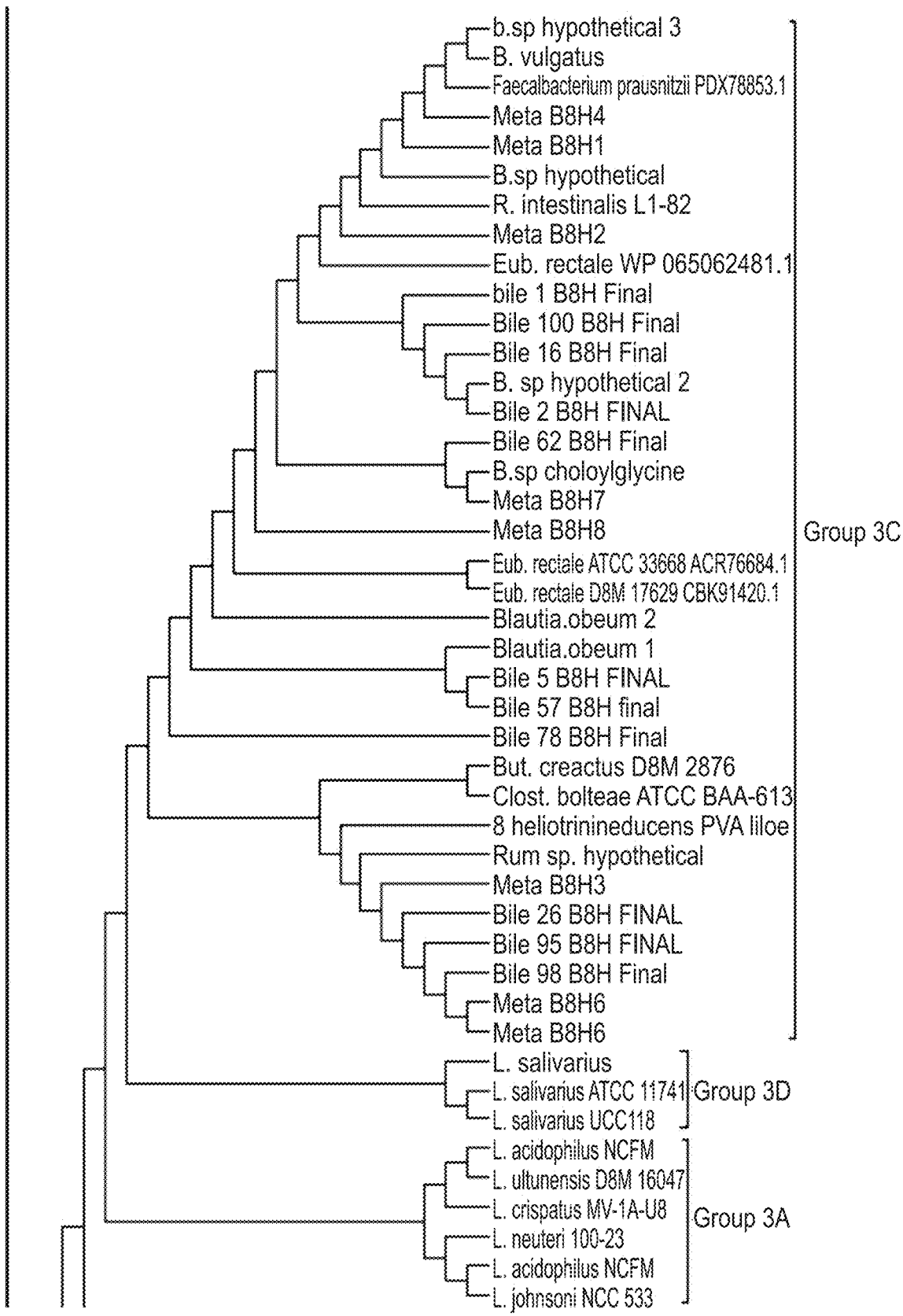
Figure 23B:
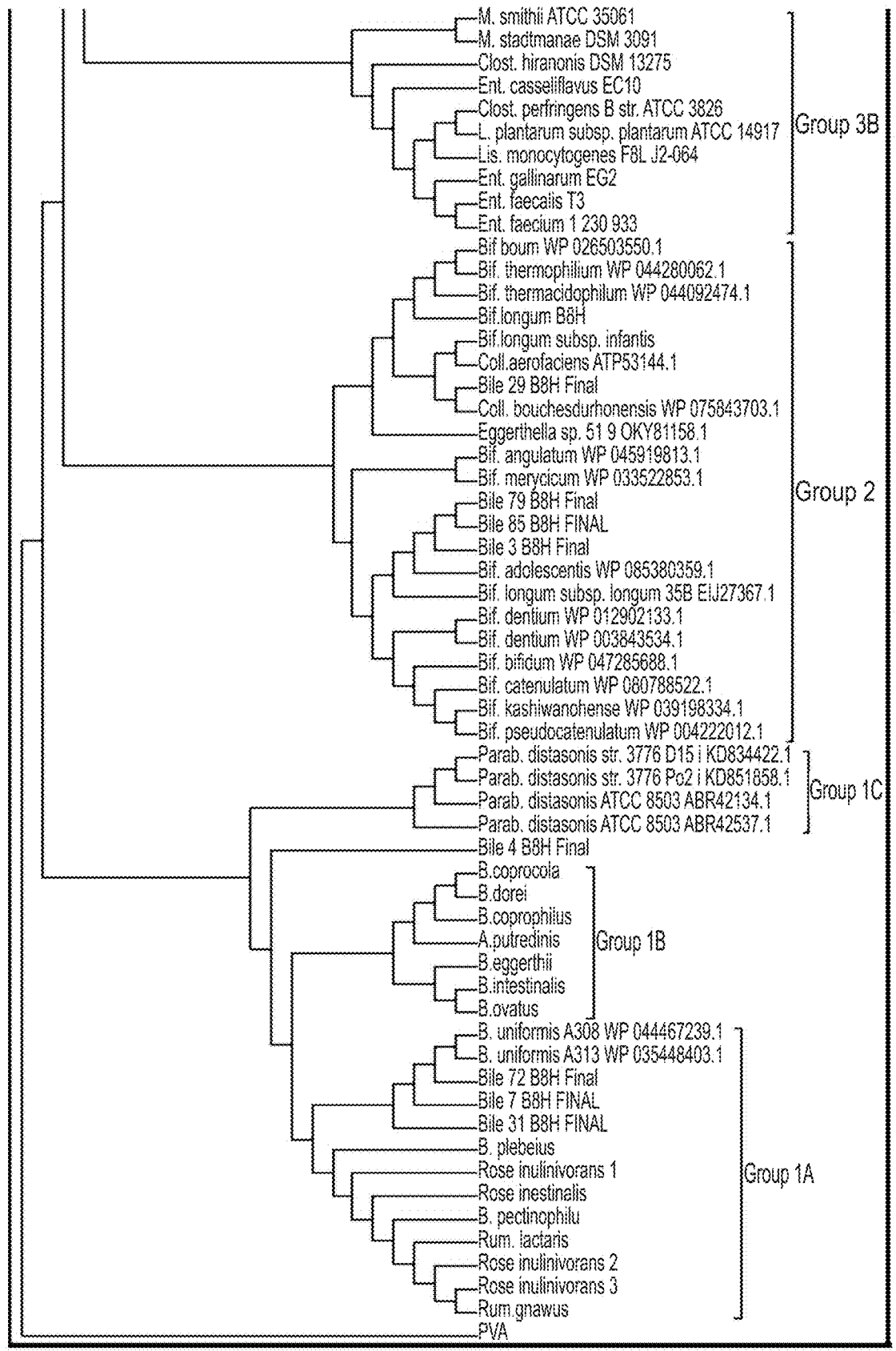
Figure 26:
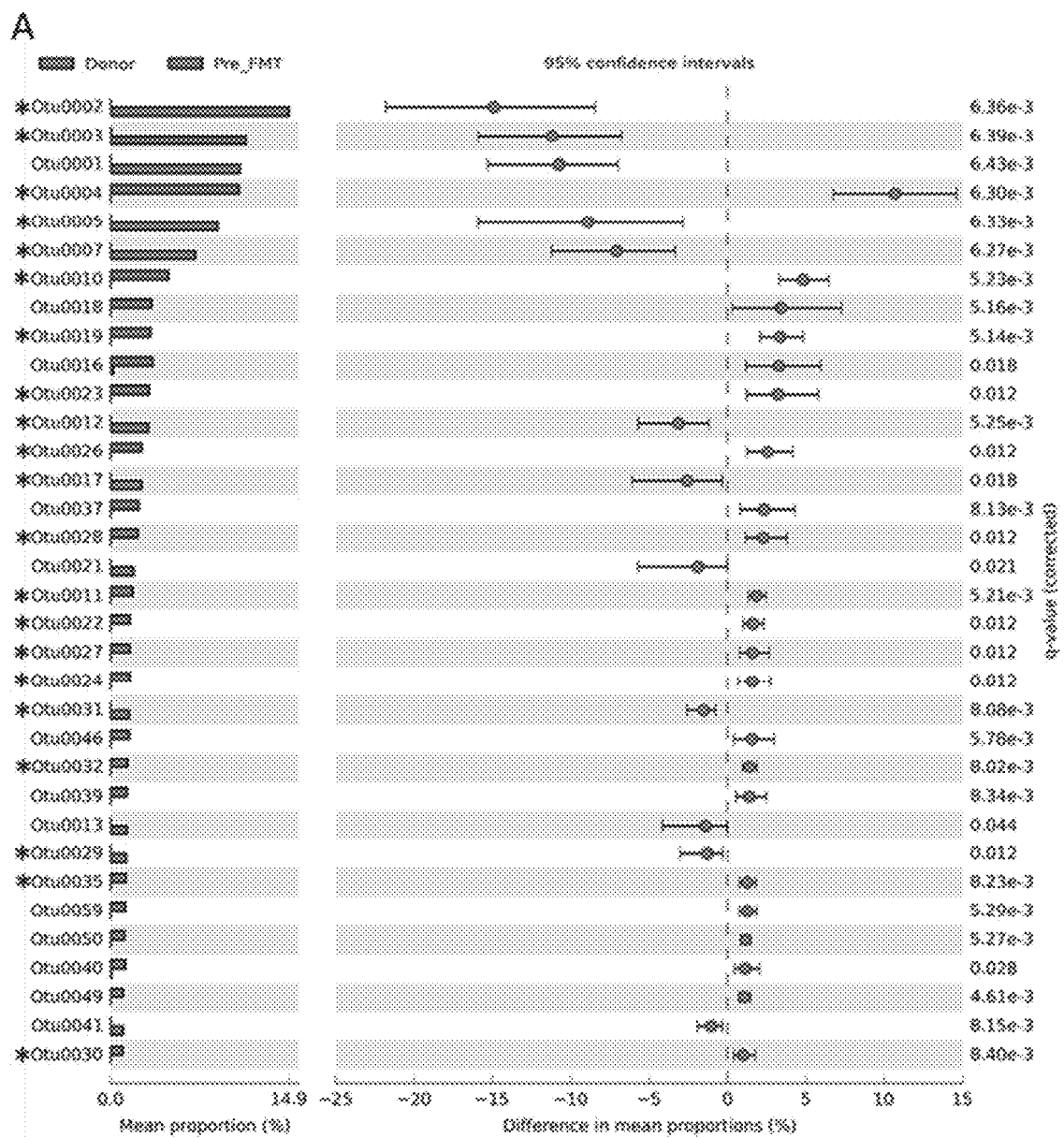
Figure 26:
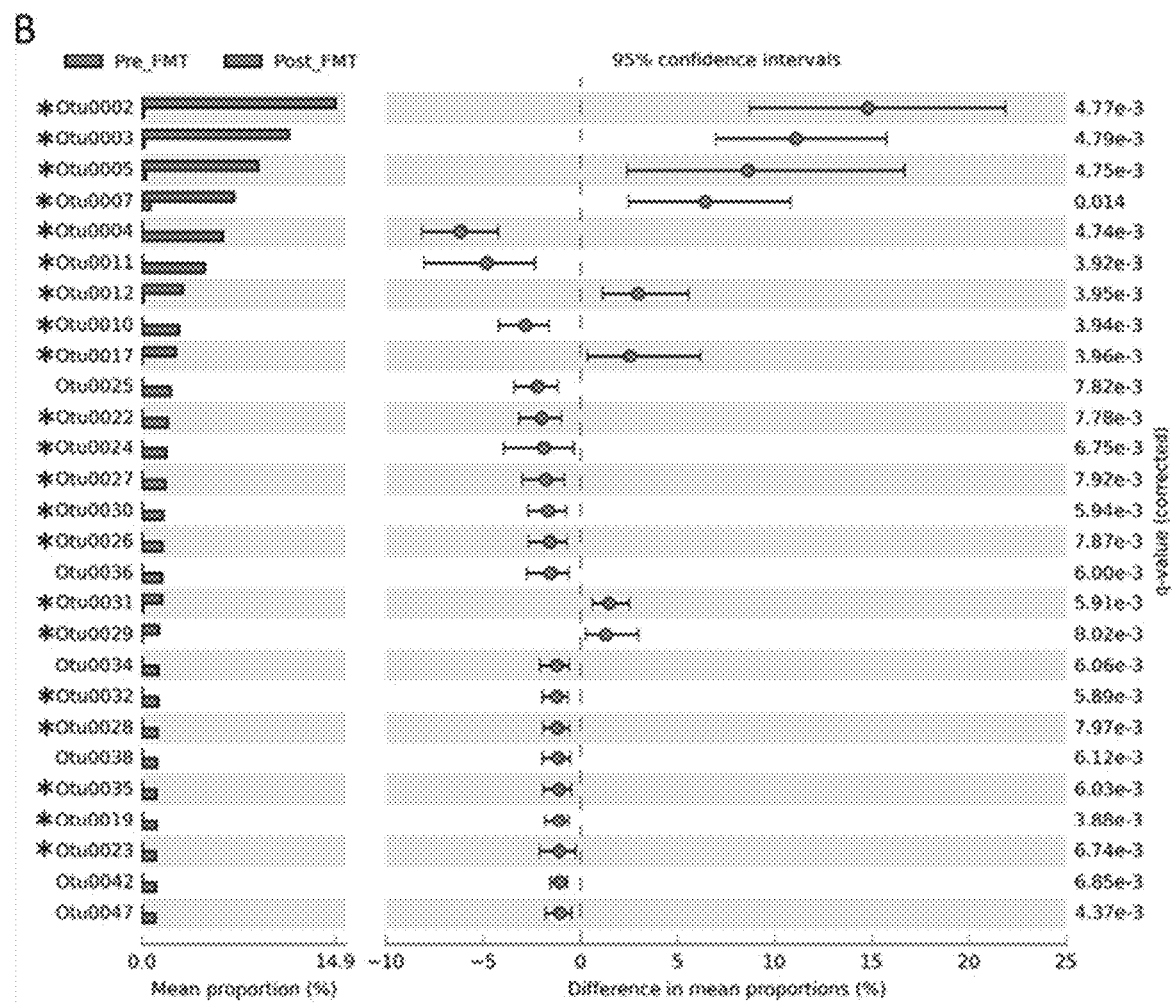
Figure 27:
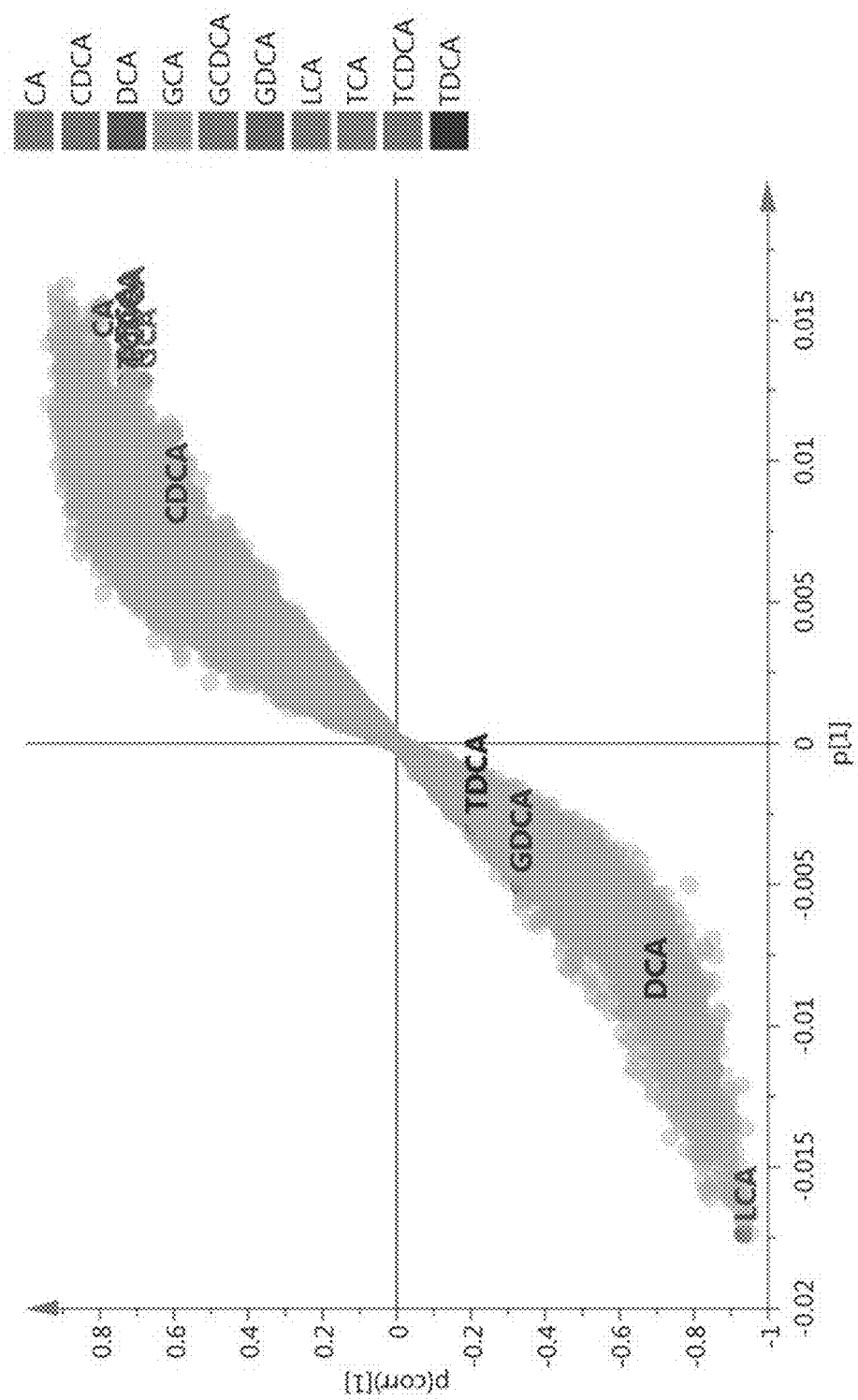

OTUs enriched in healthy donors compared to pre-FMT samples were characterised by a range of BSH-producing bacteria (FIG. 23), including members of BSH group 1 (*Bacteroides ovatus*, p=0.012; *Bacteroides uniformis*, p=0.005), BSH group 2 (*Collinsella aerofaciens*, p=0.012; *Bifidobacterium adolescentis* or *dentium*, p=0.012) and BSH group 3 (*Bacteroides vulgatus*, p=0.006; *Eubacterium rectale*, p=0.005; *Faecalibacterium prausnitzii*, p=0005) (FIG. 26A, Table 6).

TABLE 6

OTUs enriched in donors compared to pre-FMT
OTUs enriched in donors vs pre-FMT:

| OTU | Identified species | Query cover (%) | Identity (%) | q value for difference in mean proportions (corrected) |
|---|---|---|---|---|
| Otu0004 | *Bacteroides vulgatus* | 100 | 100 | 0.00630 |
| Otu0010 | *Eubacterium rectale* | 100 | 100 | 0.00523 |
| Otu0018 | Unclassified *Bacteroides* | 100 | 96 | 0.00516 |
| Otu0019 | *Faecalibacterium prausnitzii* | 100 | 99 | 0.00514 |
| Otu0016 | *Dialister invisus* | 100 | 100 | 0.018 |
| Otu0023 | Unclassified *Bacteroides* | — | — | 0.012 |
| Otu0026 | *Bifidobacterium adolescentis* | 100 | 100 | 0.012 |
|  | *Bifidobacterium dentium* | 100 | 97 |  |
| Otu0037 | *Bacteroides caccae* | 100 | 99 | 0.00813 |
| Otu0028 | *Bacteroides ovatus* | 100 | 99 | 0.012 |
| Otu0011 | *Bacteroides uniformis* | 100 | 99 | 0.00521 |
| Otu0022 | *Bacterium* LF-3 | 100 | 100 | 0.012 |
| Otu0027 | *Collinsella aerofaciens* | 100 | 99 | 0.012 |
| Otu0024 | Unclassified *Bacteroides* | 100 | 94 | 0.012 |
| Otu0046 | *Bacteroides stercoris* | 100 | 99 | 0.00578 |
| Otu0032 | *Anaerostipes hadrus* | 100 | 100 | 0.00802 |
| Otu0039 | Unclassified *Ruminococcaceae* | — | — | 0.00834 |
| Otu0035 | Unclassified *Oscillibacter* | — | — | 0.00832 |
| Otu0059 | *Faecalibacterium prausnitzii* | 100 | 98 | 0.00529 |
| Otu0050 | *Fusicatenibacter saccharivorans* | 100 | 99 | 0.00527 |
| Otu0040 | *Bifidobacterium longum* | 100 | 100 | 0.028 |
|  | *Bifidobacterium sanguini* | 100 | 97 |  |
| Otu0049 | Unclassified *Lachnospiraceae* | — | — | 0.00461 |
| Otu0030 | *Barnesiella intestinihominis* | 100 | 99 | 0.00840 | similarly, OTUs enriched in post-FMT samples compared to those pre-FMT also included members of all BSH groups, including group 1 (*Bacteroides ovatus*, p=0.008; *Bacteroides uniformis*, p=0.004; *Parabacteroides distasonis*, p=0.004)), group 2 (*Collinsella aerofaciens*, p=0.079; *Bifidobacterium adolescentis* or *dentium*, p=0.012) and group 3 (*Eubacterium rectale*, p=0.004; *Blautia obeum*, p=0.007; *Faecalibacterium prausnitzii*, p=0.004; *Bacteroides vulgatus*, p=0.005) (FIG. 26B, Table 7).

TABLE 7

OTUs enriched post-FMT compared to pre-FMT
OTUs enriched post-FMT compared to pre-FMT:

| OTU | Identified species | Query cover (%) | Identity (%) | q value for difference in mean proportions (corrected) |
|---|---|---|---|---|
| Otu0004 | *Bacteroides vulgatus* | 100 | 100 | 0.00474 |
| Otu0011 | *Bacteroides uniformis* | 100 | 99 | 0.00392 |
| Otu0010 | *Eubacterium rectale* | 100 | 100 | 0.00394 |
| Otu0025 | *Parabacteroides johnsonii* | 100 | 98 | 0.00782 |
| Otu0022 | *Bacterium* LF-3 | 100 | 100 | 0.00778 |
| Otu0024 | Unclassified *Bacteroides* | 100 | 94 | 0.00675 |
| Otu0027 | *Collinsella aerofaciens* | 100 | 99 | 0.00792 |
| Otu0030 | *Barnesiella intestinihominis* | 100 | 99 | 0.00594 |
| Otu0026 | *Bifidobacterium adolescentis* | 100 | 100 | 0.00787 |
|  | *Bifidobacterium dentium* | 100 | 97 |  |
| Otu0036 | *Bacteroides cellulosilyticus* | 100 | 98 | 0.00600 |
| Otu0034 | *Blautia obeum* | 100 | 97 | 0.00606 |
| Otu0032 | *Anaerostipes hadrus* | 100 | 100 | 0.00589 |
| Otu0028 | *Bacteroides ovatus* | 100 | 99 | 0.00797 |
| Otu0038 | *Bacteroides ovatus* | 100 | 97 | 0.00612 |
| Otu0035 | Unclassified *Oscillibacter* | — | — | 0.00603 |
| Otu0019 | *Faecalibacterium prausnitzii* | 100 | 99 | 0.00388 |
| Otu0023 | Unclassified *Bacteroides* | — | — | 0.00674 |
| Otu0042 | *Blautia obeum* | 100 | 98 | 0.00685 |
| Otu0047 | *Parabacteroides distasonis* | 100 | 98 | 0.00437 |

*Clostridium scindens* is the archetypal-7—α-dehydroxylase producing organism, having been shown to have high levels of activity in the production of secondary bile acids[25], and also to have a role in maintaining colonisation resistance within the rodent gut microbiota[26]. The only OTU identified that could be labelled as *Clostridium scindens* was found in significantly reduced proportions between pre-FMT samples in comparison to donors (p=0.007, Table 8), but with mean proportion difference of <1%. In contrast, this OTU was not found to be significantly enriched post-FMT in comparison to pre-FMT samples (p=1.096, Table 8). However, it was noted that there was a decreased relative abundance of the genus *Clostridium* cluster XIVa (the genus most strongly associated with 7-α-dehydroxylase-producing organisms) in pre-FMT samples compared to donor samples (p=0.007), and in pre-FMT samples compared to post-FMT samples (p=0.005).

TABLE 8

Changes in the OTU corresponding to *Clostridium scindens*.

| OTU | Identified species | Query cover (%) | Identity (%) | q value for difference in mean proportions (corrected) |
|---|---|---|---|---|
| OTUs enriched in donors vs pre-FMT: | | | | |
| Otu0212 | *Clostridium scindens* | 100 | 99 | 0.00663 |
| OTUs enriched post-FMT compared to pre-FMT: | | | | |
| Otu0212 | *Clostridium scindens* | 100 | 99 | 1.096 |

FMT Restores Normal Gut Bile Acid Profiles

Figure 18:
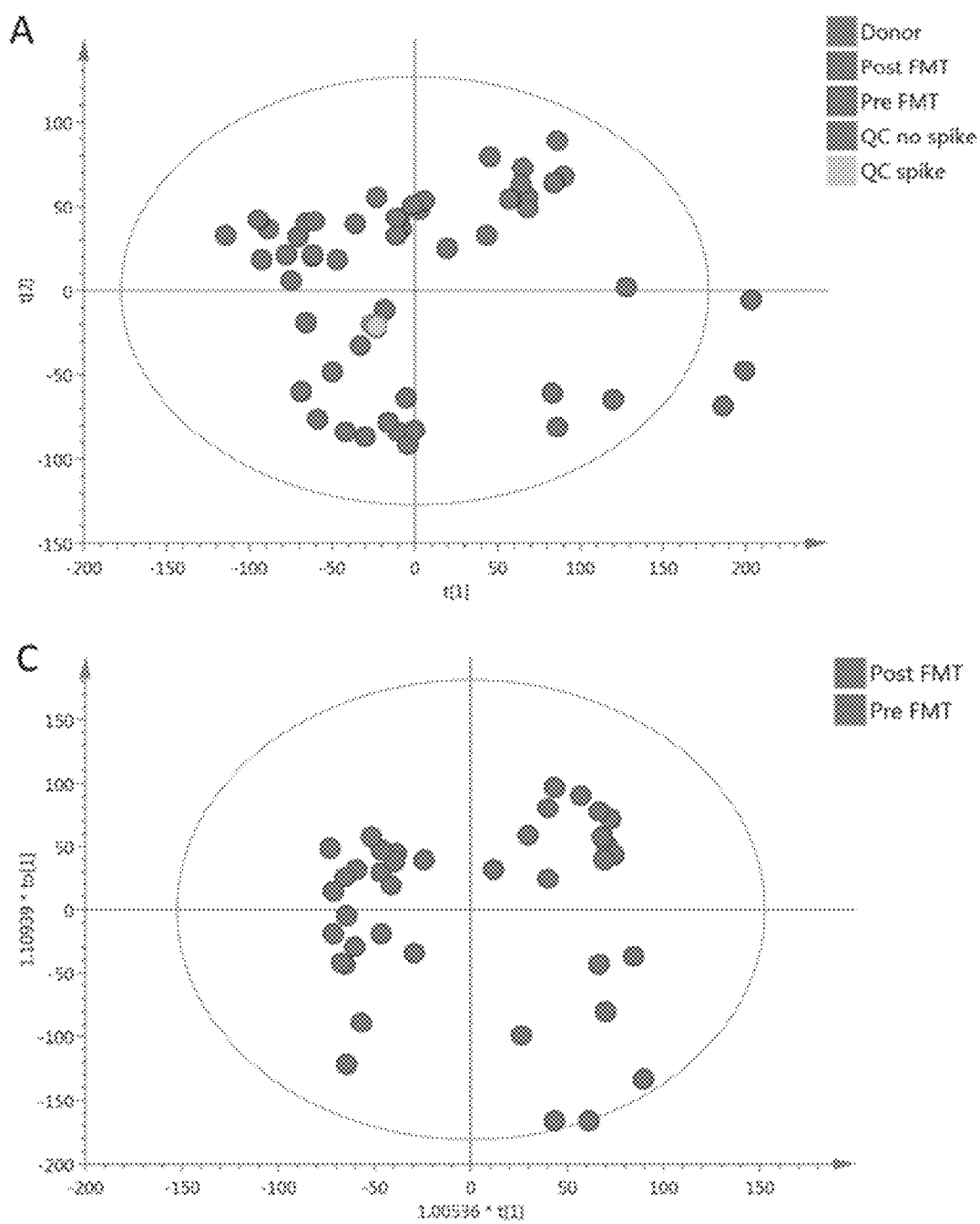
Figure 18:
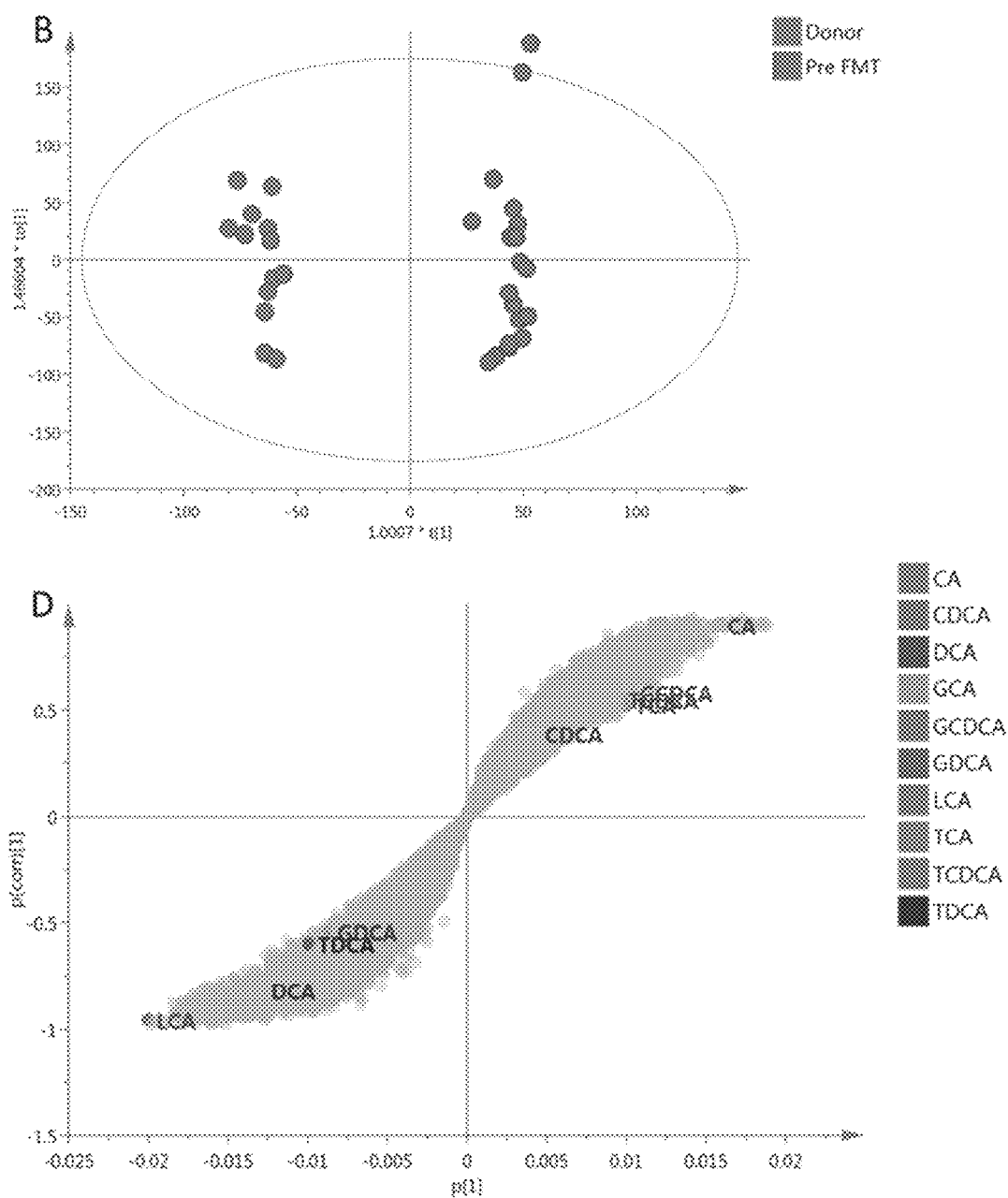
Figure 28:
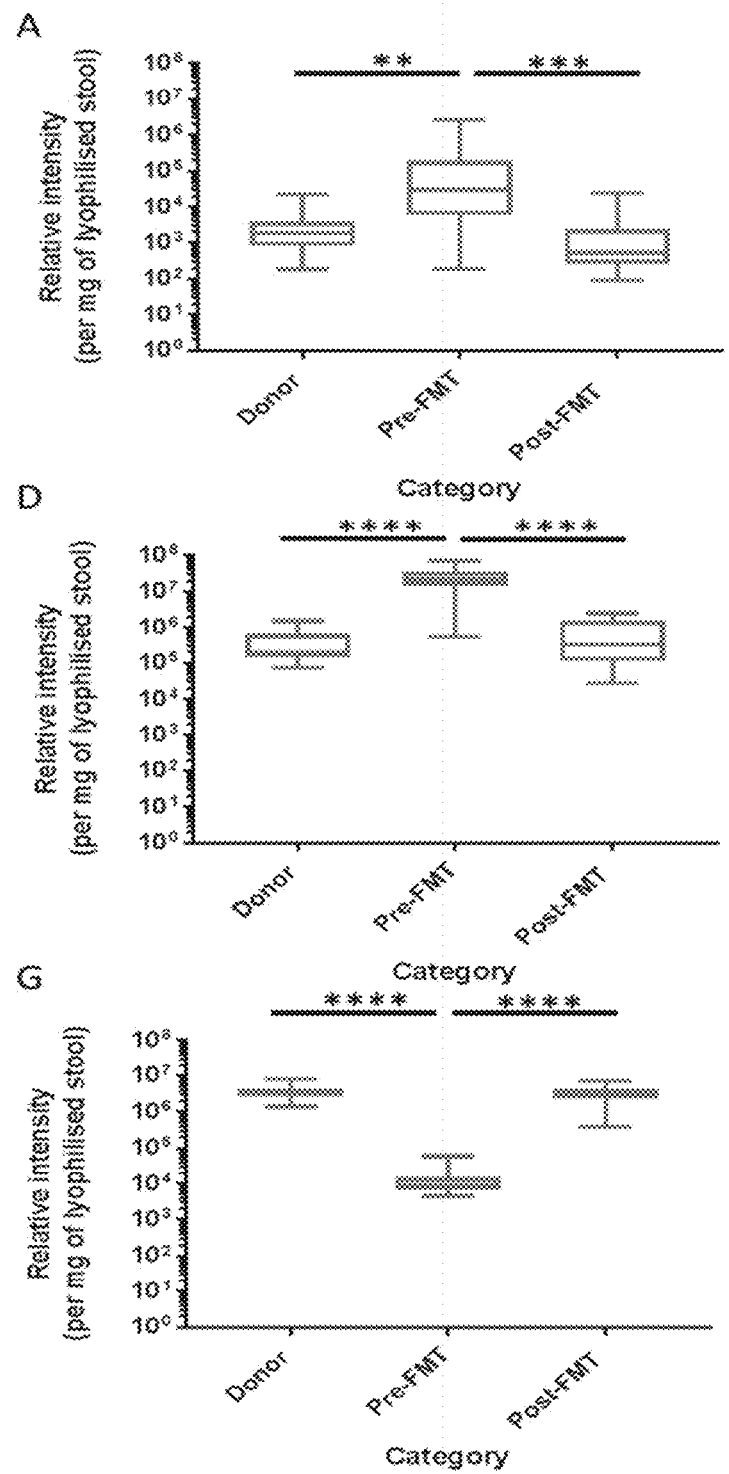
Figure 28:
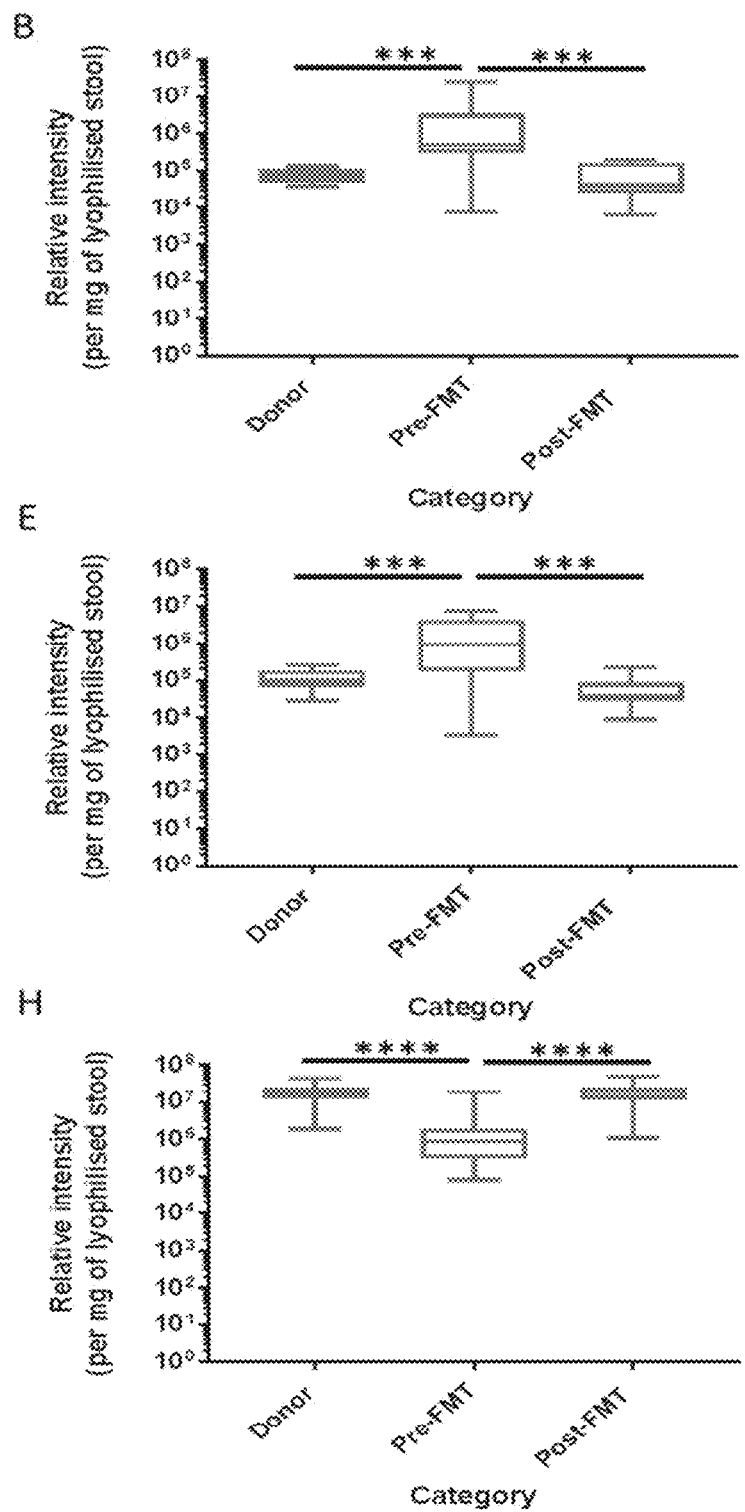
Figure 28:
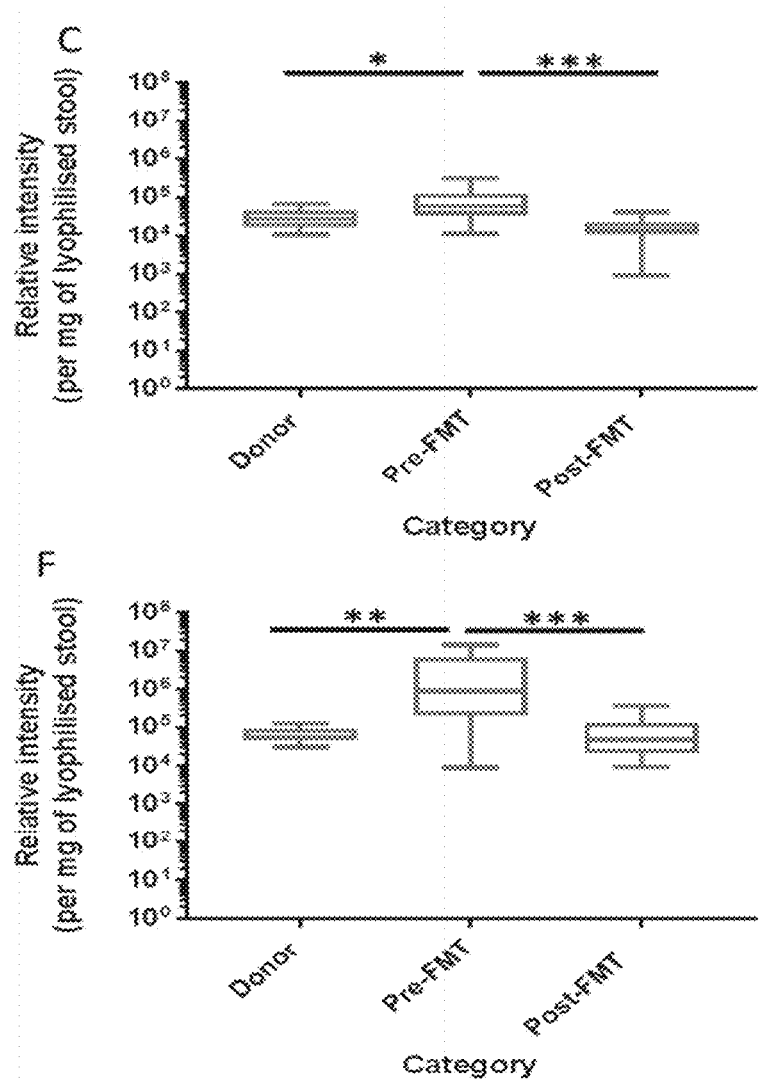
Figure 29:
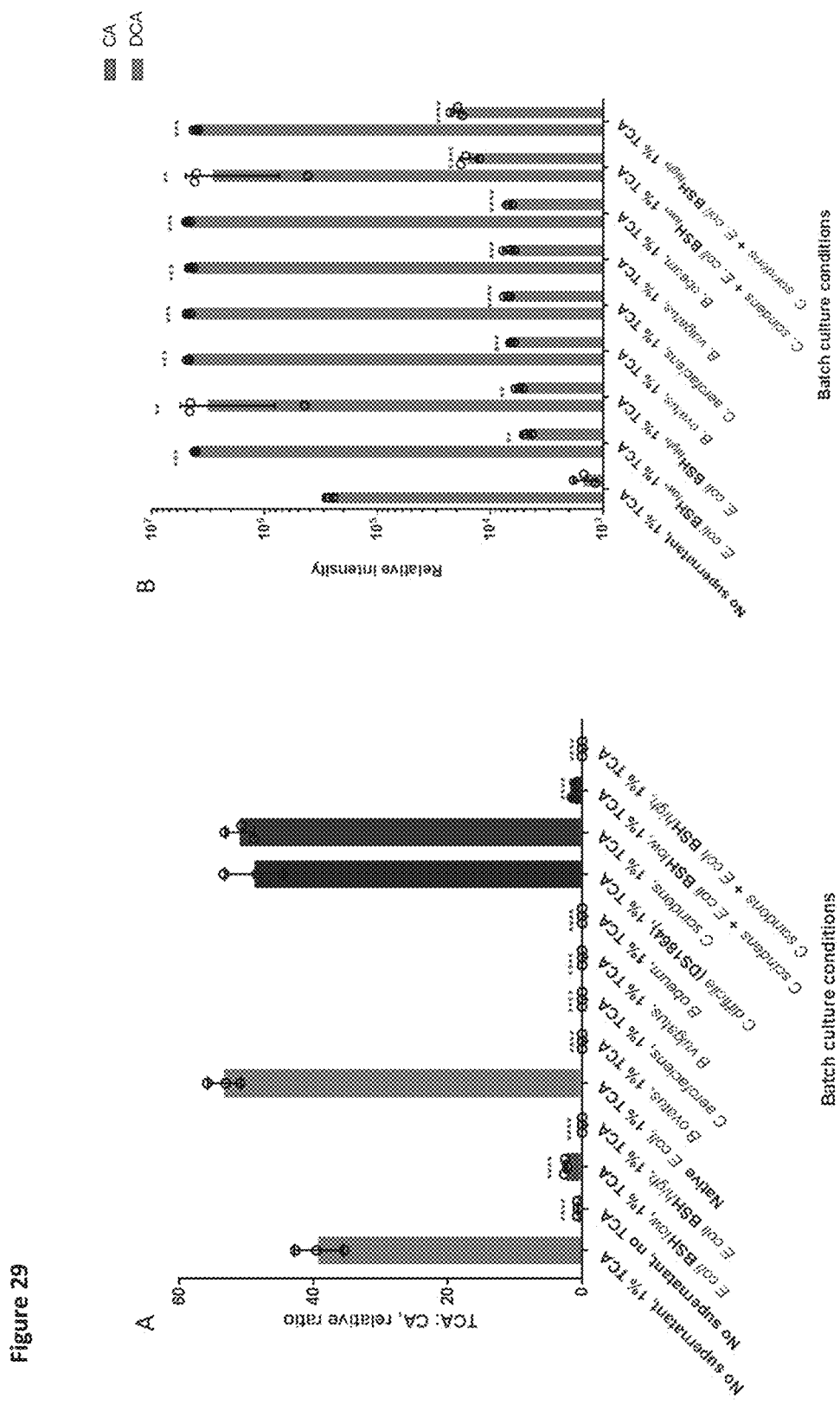
Figure 30:
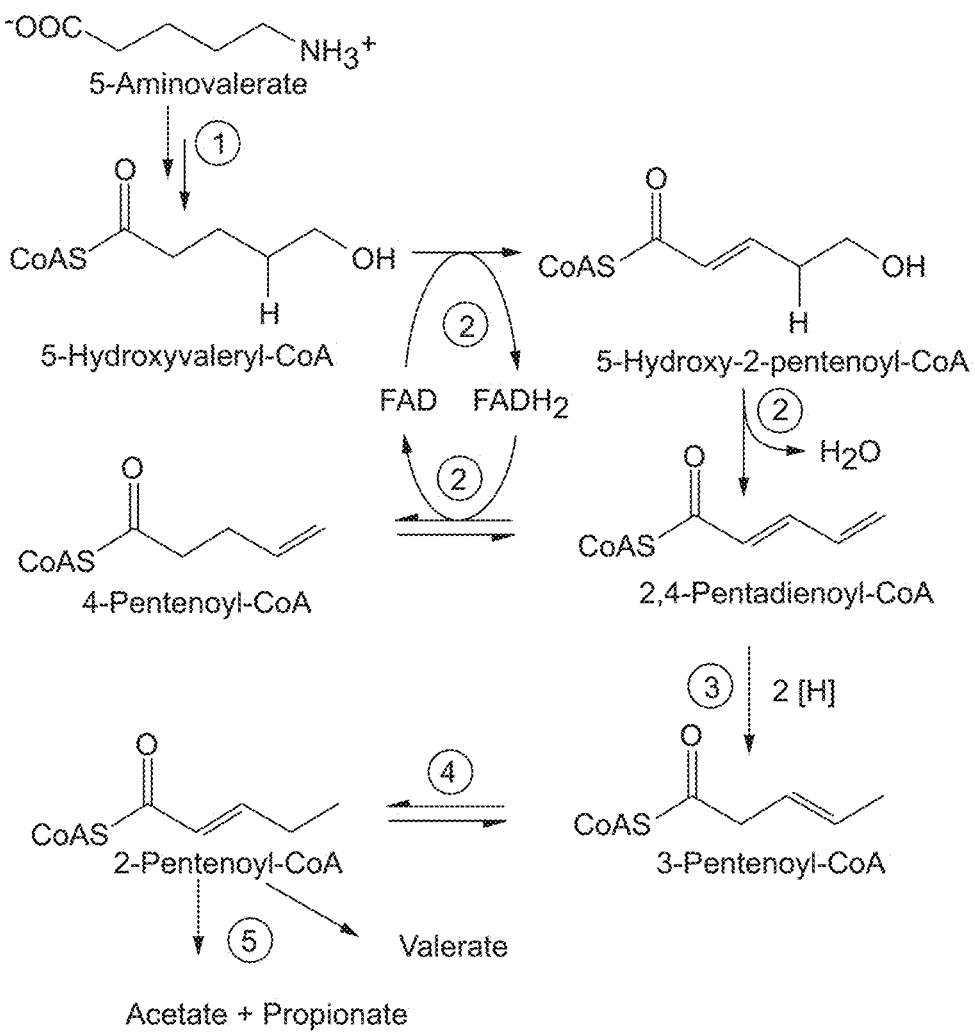

On multivariate analysis of UPLC-MS bile acid profiling data, unsupervised principal component analysis (PCA) demonstrated clustering of donor and post-FMT samples, but clear separation of both groups from pre-FMT samples (FIG. 18A). A supervised analysis was performed with OPLS-DA to analyse the features responsible for discrimination between donor and pre-FMT groups (FIG. 18B), and between pre-FMT and post-FMT groups (FIG. 18C). Discriminatory feature identification was performed from OPLS-DA model data via S-plot, with pre-FMT samples showing an enrichment in primary bile acids (including both conjugated and unconjugated forms) and loss of secondary bile acids as compared to post-FMT and healthy donor samples (FIG. 18D, FIG. 28. OPLS-DA model validation was performed using CV-ANOVA (Table 9). Univariate analysis supported these findings (FIG. 29; in particular, pre-FMT samples demonstrated enrichment in TCA and loss of DCA compared to healthy donor samples (p<0.01, Mann-Whitney test), whilst post-FMT samples were characterised by restoration of both bile acids back to levels comparable to donors (p<0.001, Wilcoxon rank sum test).

TABLE 9

Model characteristics for OPLS-DA models. Validation of the models is expressed with p values derived from CV-ANOVA.

| Multi-variate model | $R^2X$ | $Q^2$ | p value |
|---|---|---|---|
| Donor vs pre-FMT | 0.533 | 0.933 | $1.85 \times 10^{-13}$ |
| Pre-vs post-FMT | 0.437 | 0.839 | $5.24 \times 10^{-13}$ |

Figure 19:
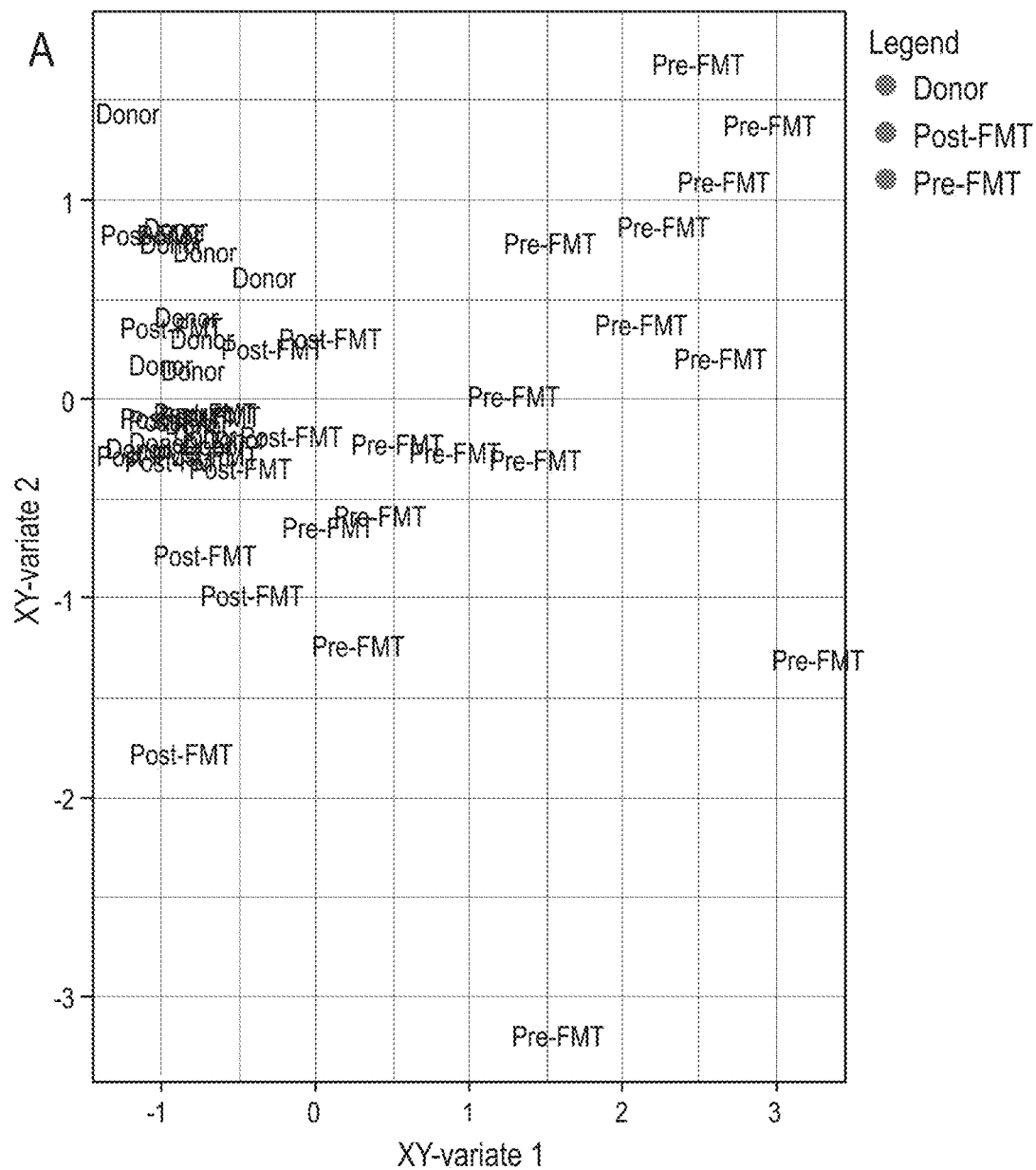
Figure 19:
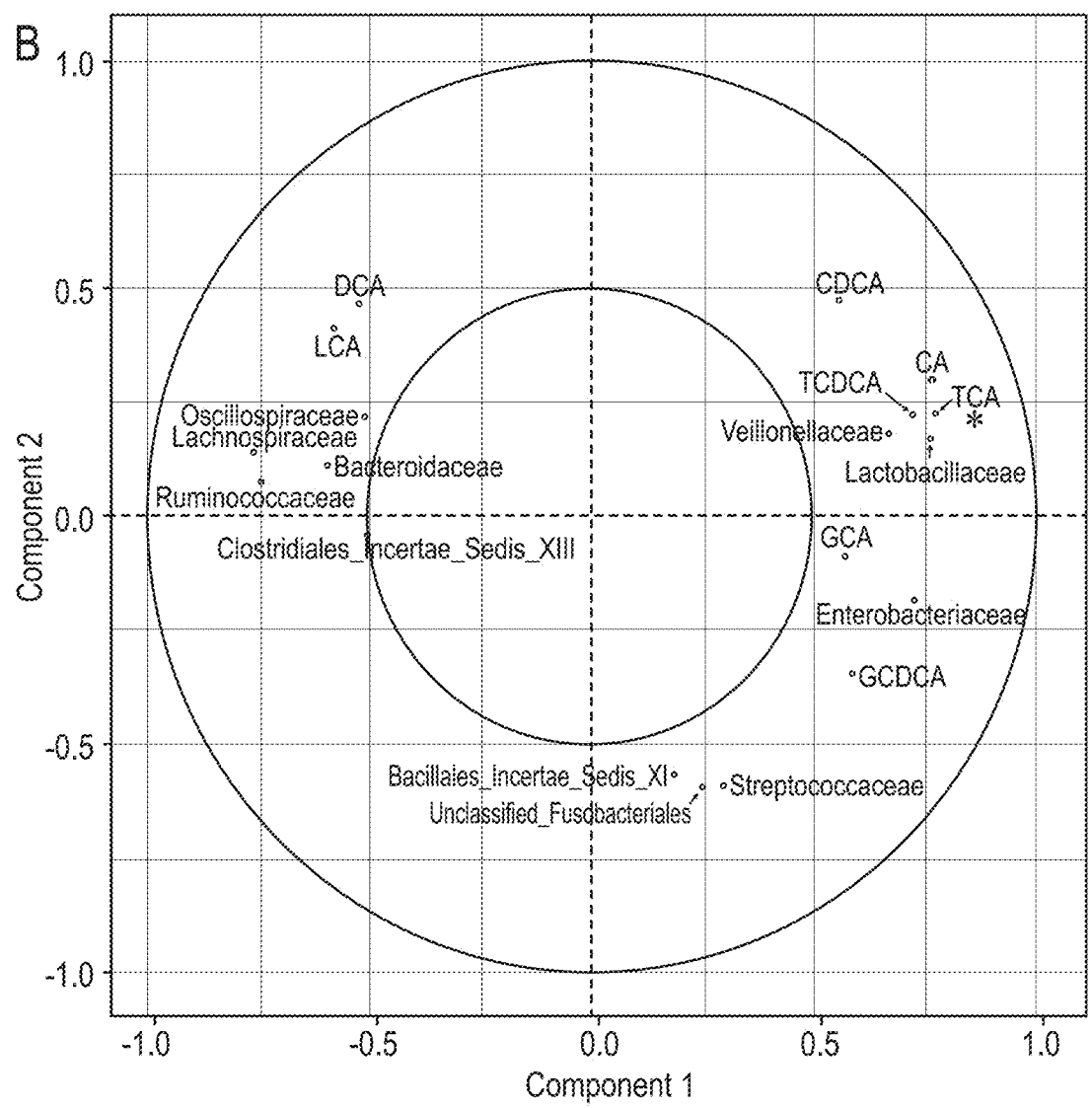

Correlation Between Bacterial Families and Bile Acid Profiles rCCA modelling was used to integrate metataxonomic and bile acid profiling data. The unit representation plot demonstrated marked separation of pre- and post-FMT samples, but considerable overlap between donor and post-FMT samples (FIG. 19A). A correlation circle plot demonstrated strong positive correlation (r>0.5) between levels of the secondary bile acids DCA and lithocholic acid (LCA) and the abundance of the bacterial families Lachnospiraceae, Ruminococcaceae, Bacteroidaceae, Oscillospiraceae and Clostridiales Incertae Sedis XII (FIG. 19B). Secondary bile acids correlated negatively with primary bile acids, both conjugated (including TCA) and unconjugated (FIG. 19B). Lachnospiraceae, Ruminococcaceae and Bacteroidaceae are all bacterial families known to include BSH-producing organisms[22], with Lachnospiraceae and Clostridiales Incertae Sedis XIII both containing 7-α-dehydroxylase-producers[23-24].

Figure 20:
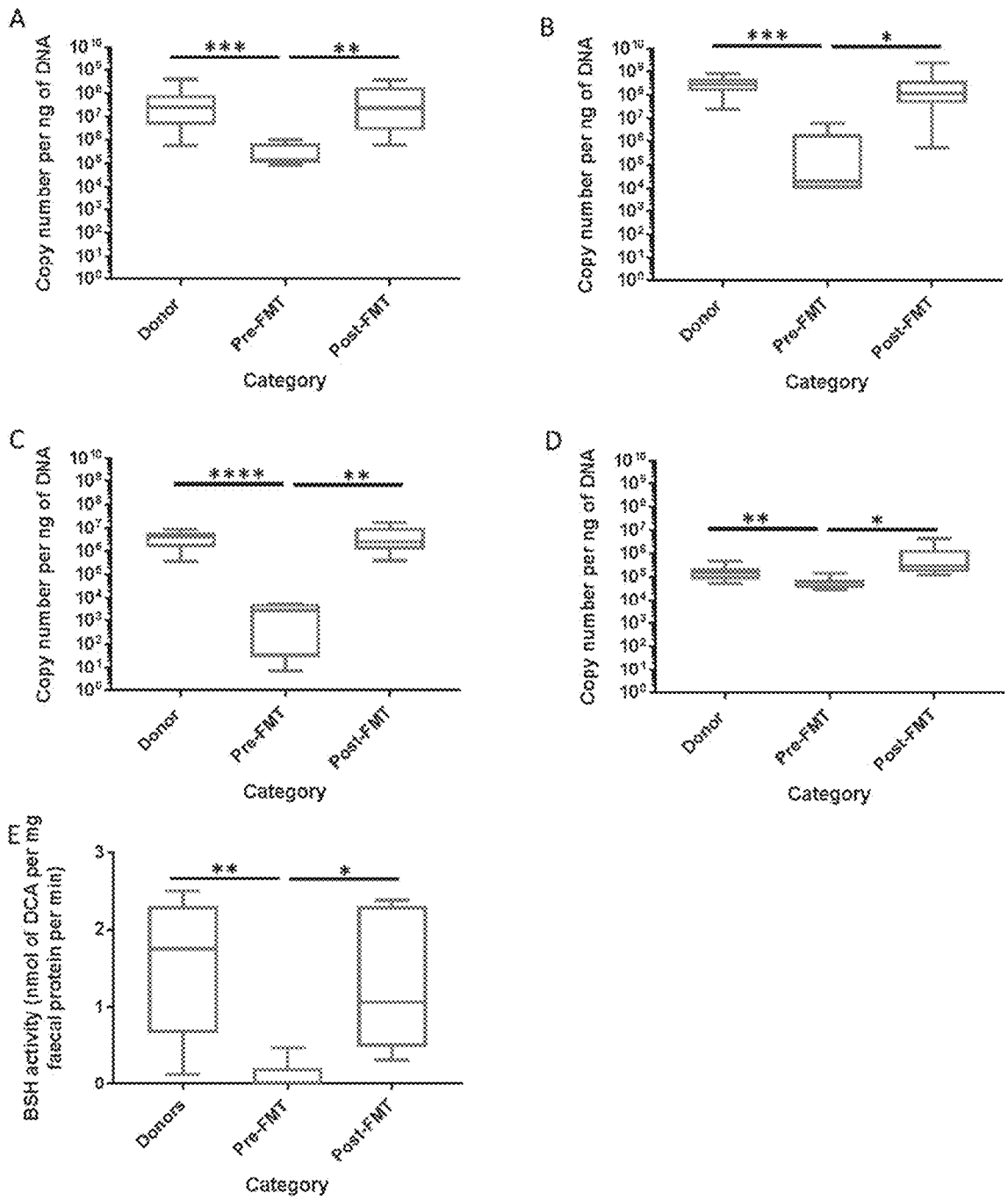

Gut bile-metabolising functionality is restored through FMT Bsh gene copy number was significantly reduced in pre-FMT samples compared to healthy donors across a range of bsh gene groups (p<0.001, Mann-Whitney U test, FIG. 20A-C). Successful FMT was associated with significant enrichment in copy number of all bsh gene groups assayed (p<0.05, Wilcoxon rank sum test, FIG. 20A-C) to levels similar to that of healthy donors. Copy number was also assessed for the baiCD operon; whilst this operon is not found in all bacteria with 7-α-dehydroxylating ability, it is present within the two bacterial species with high activity of this enzyme, *Clostridium scindens* and *Clostridium hiranonis*, and good correlation has been found between baiCD number and 7-α-dehydroxylase activity[25,27]. Copy numbers of the baiCD operon were significantly lower in pre-FMT samples compared to those of healthy donors (p<0.01), but were also significantly enriched post-FMT (p<0.05, FIG. 20D). Gene copy number for baiCD in donors and post-FMT was noted to be markedly lower than for each bsh gene assayed for the same participants.

Stool BSH activity showed a comparable pattern. Specifically, pre-FMT levels of BSH activity within faecal supernatant were significantly lower than that of healthy donors (p<0.01, Mann-Whitney test, FIG. 20E), but after successful FMT activity was significantly increased to levels comparable to that of donors (p<0.05, Wilcoxon rank sum test, FIG. 20E).

Taurocholic Acid-Mediated *C. difficile* Germination is Fully Reversed Through Introduction of BSH The inventor's data demonstrated an association between successful FMT, breakdown of TCA, and restoration of gut BSH-producing microorganisms and BSH functionality.

To further explore whether these changes were purely associative or represented a causative pathway for CDI pathogenesis, the inventors performed *C. difficile* batch culture germination experiments.

The inventors prepared spent culture supernatants by incubating bacteria of interest in broth containing 1% w/v TCA (~19 mM). After an overnight incubation, the cultures were centrifuged and filter sterilised. *C. difficile* spores were incubated in supplemented brain-heart infusion (sBHI) broth supplemented with the spent culture supernatant. Using this setup, *C. difficile* spores incubated with spent culture supernatants without BSH activity would have TCA available to stimulate germination and therefore grow, while *C. difficile* spores incubated with spent culture supernatants with BSH activity would not have TCA available to stimulate germination and would not grow.

For initial experiments, strains of interest included wild type *E. coli* (which lacks a bsh gene), or two forms of *E. coli* into which bsh genes had been cloned (i.e. '*E. coli* $BSH_{low}$', containing a gene for BSH with narrow substrate range against conjugated bile acids; and '*E. coli* $BSH_{high}$', containing a gene for BSH with high glycine and taurine-deconjugating activity). While spent supernatant from the culture of wild type *E. coli* did not affect the ability of *C. difficile* to undergo germination, that from both forms of bsh gene-expressing *E. coli* significantly reduced *C. difficile* germination across all ribotypes tested (q<0.0001, ANOVA with multiple group testing, Benjamini-Hochberg correction) (FIG. 21A). *C. difficile* germination was significantly lower for all three ribotypes when incubated in TCA-supplemented supernatant from an *E. coli* $BSH_{high}$ batch culture as compared to *E. coli* $BSH_{low}$ (p<0.05).

Figure 21:
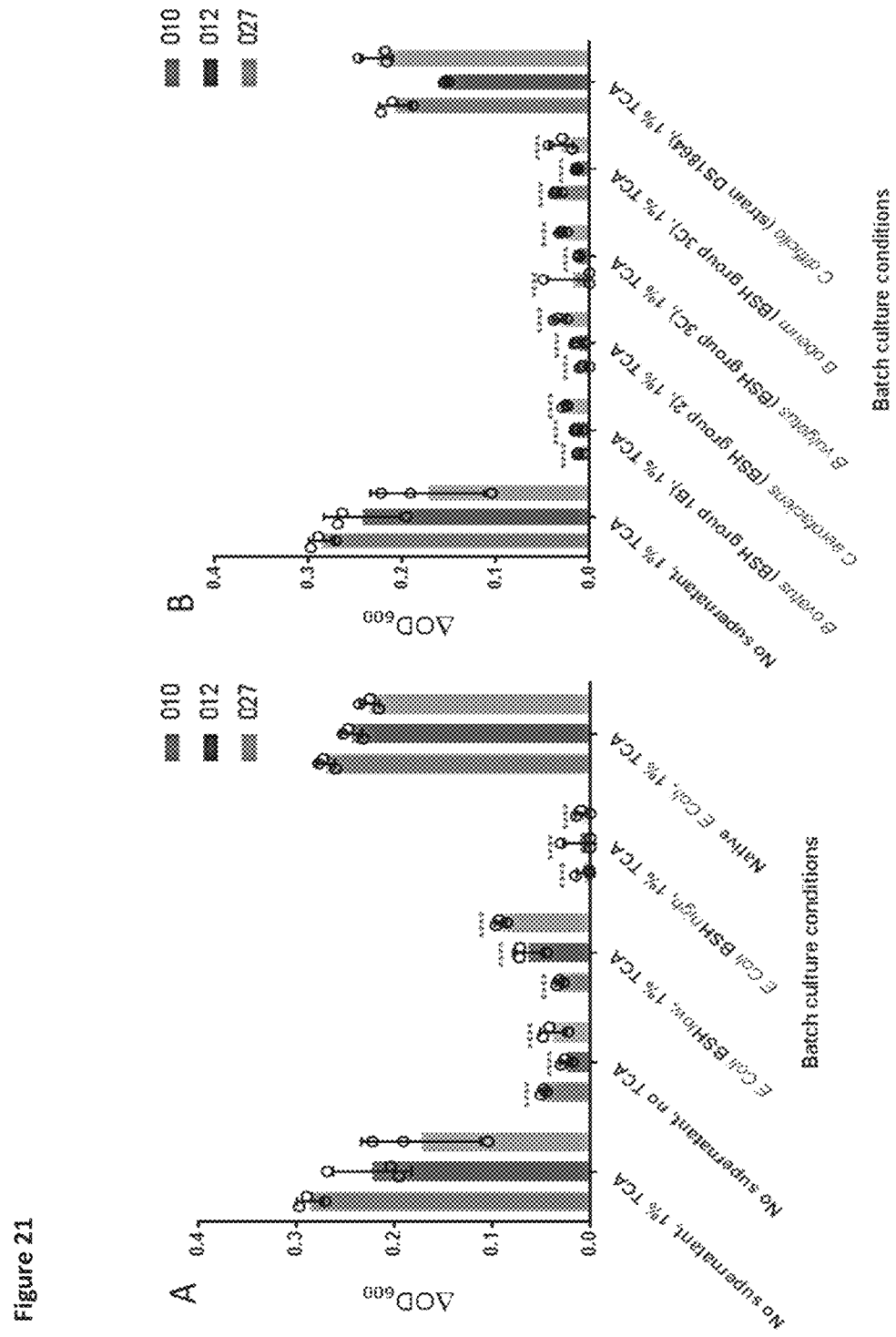
Figure 21:
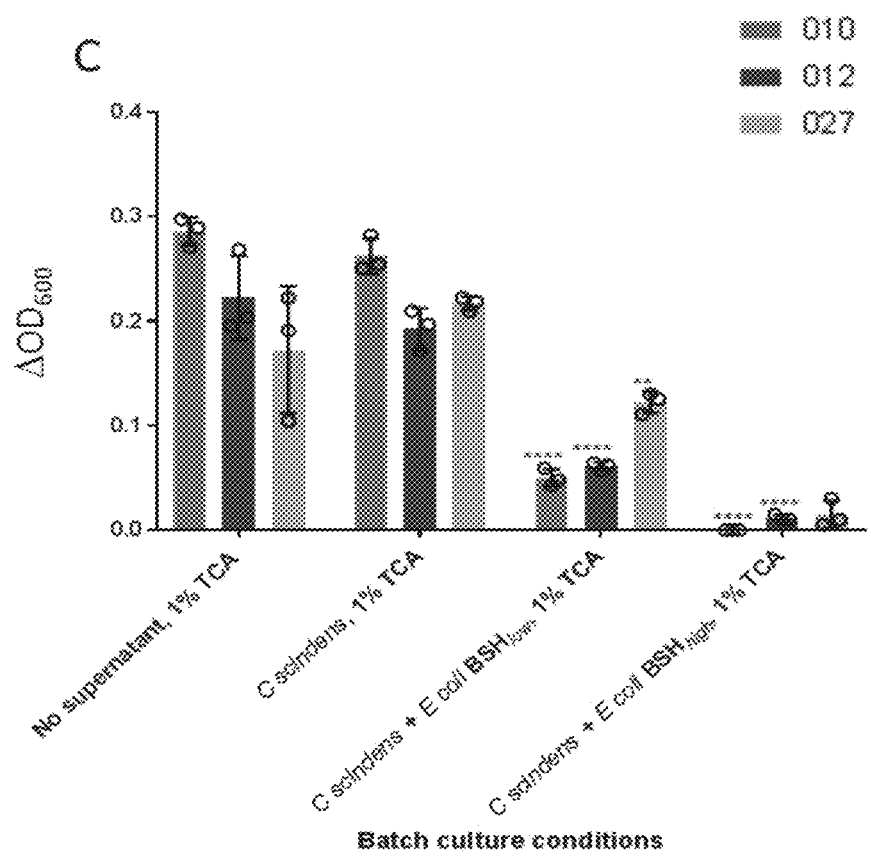
Figure 22:
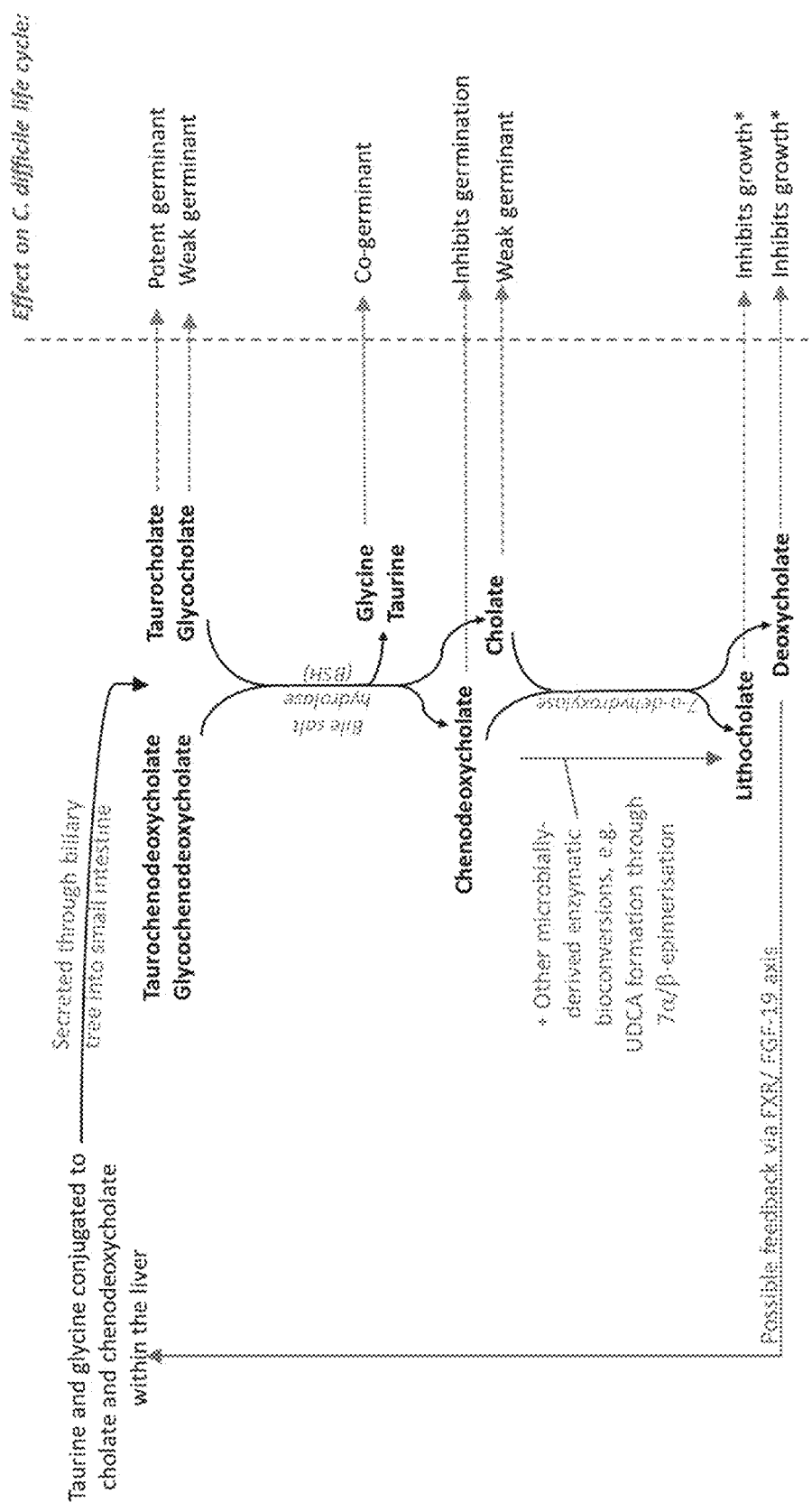

Subsequently, *C. difficile* spores were incubated with spent supernatant from BSH-expressing microbial organisms that had been incubated with TCA. The microorganisms selected were those which had been shown to be reduced in mean proportion in the gut microbiota of pre-FMT patients in comparison to donors and/or post-FMT samples, and which collectively represented most BSH groups. For all *C. difficile* ribotypes assayed, supernatant from the broth of each of the BSH-producing microbe assayed significantly reduced *C. difficile* germination ($p<0.0001$) (FIG. 21B). As a control, spent supernatant from TCA-supplemented broth in which vegetative *C. difficile* had been cultured (strain DS1864) failed to affect *C. difficile* germination. *C. difficile* spores were cultured in spent supernatant from *Clostridium scindens* which had been incubated with TCA, either by itself or also in co-culture with BSH-expressing *E. coli*. Spent supernatant from *C. scindens* did not affect *C. difficile* germination ability by itself, but germination was significantly reduced when *C. scindens* was co-incubated with BSH-expressing *E. coli* ($p<0.01$) (FIG. 21C).

Analysis by UPLC-MS confirmed that TCA-supplemented batch culture media which included supernatant from native *E. coli*, vegetative *C. difficile*, and *C. scindens* culture had high TCA:CA ratios, consistent with little/absent BSH activity within these batch cultures (FIG. 29A). Low TCA:CA ratios were noted for all other batch cultures, indicating the presence of BSH activity. All batch culture experiments in which *C. difficile* germination was suppressed were characterised by low levels of DCA within supernatant (although levels of DCA were somewhat higher in those batch cultures containing *C. scindens* and bsh-expressing *E. coli* than batch cultures containing BSH-producing organisms alone). More specifically, relative intensities of DCA within these batch cultures were ~1000 times lower than those of CA (FIG. 29B). Collectively, these batch culture results show that suppression of *C. difficile* germination reflected degradation of the pro-germinant TCA by BSH, rather than via the production of growth-inhibiting DCA.

Figure 31:
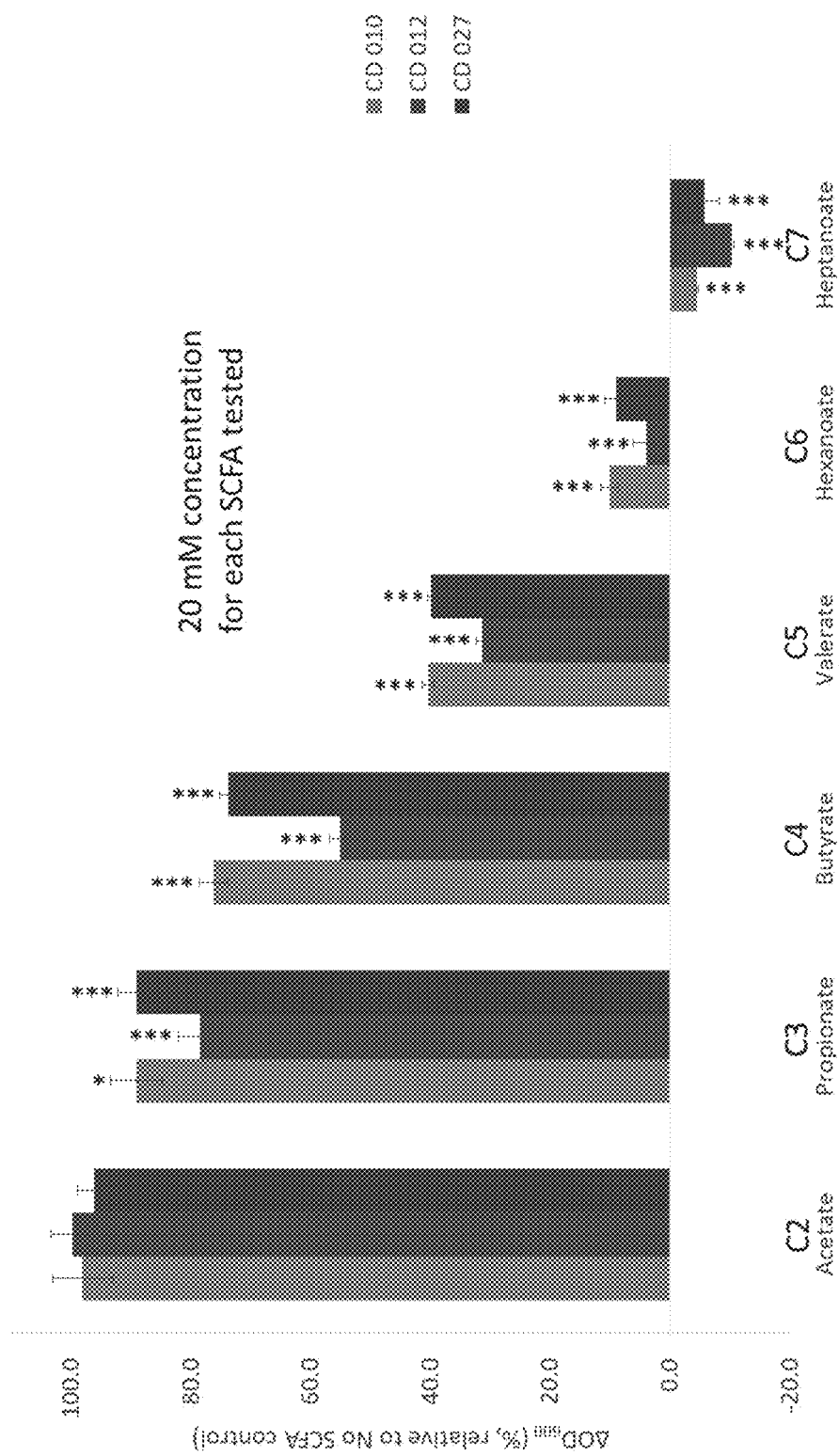
FIG. 31 shows growth inhibition of *C. difficile* when incubated with 20 mM short or medium chain fatty acids. Acetate is a C2 chain and they increase by one carbon until heptanoate is reached which is C7.

Assessment of Growth Inhibition of *C. difficile* with Short or Medium Chain Fatty Acids The inventors assessed a range of short/medium chain fatty acids (S/MCFA). Their results show that numerous short/medium chain fatty acids are inhibitors *C. difficile*. In particular, valerate (aka pentanoate—a 5 carbon acid) and the 6 carbon and 7 carbon MCFA, hexanoate and heptanoate, respectively (FIG. 31) are all potent inhibitors of *C. difficile*. Furthermore, hexanoate and heptanoate, the two longer chain versions, are significantly more potent at inhibiting growth the *C. difficile* pathogen than valerate.

Figure 32:
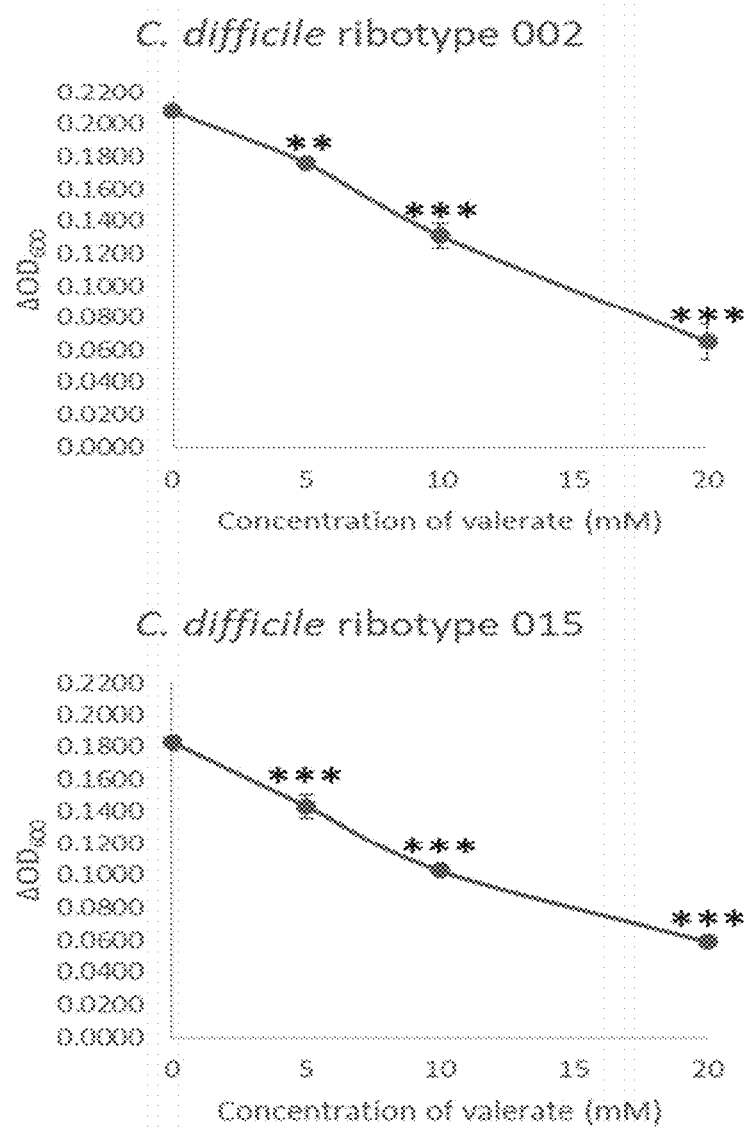
FIG. 32 shows plots of the change in OD600 against different concentrations of valerate (0, 5, 10, and 20 mM) and 6 strains of *C. difficile*. Error bars represent mean±SD. **$p<0.01$;*$p<_{0.001}$ (ANOVA and Tukey post hoc test), N=12.
Figure 32:
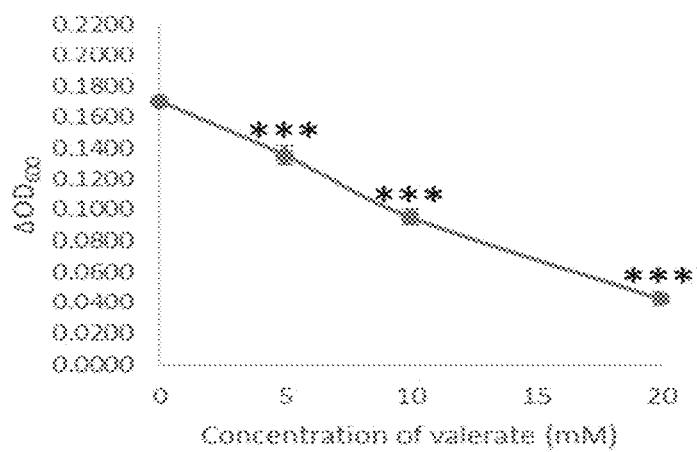
Figure 32:
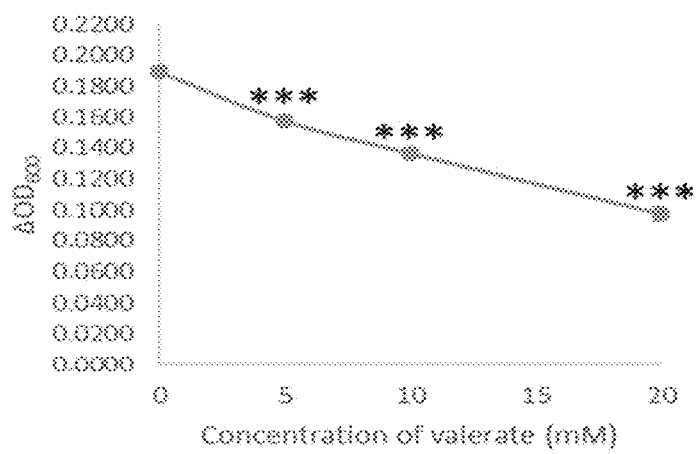
Figure 32:
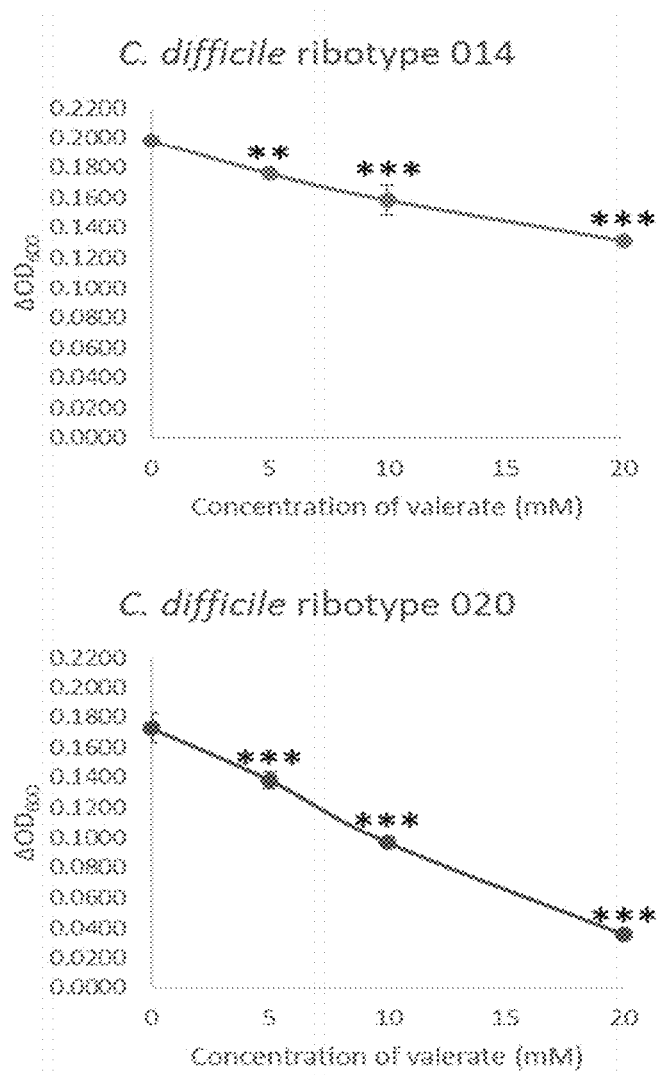
Figure 33:
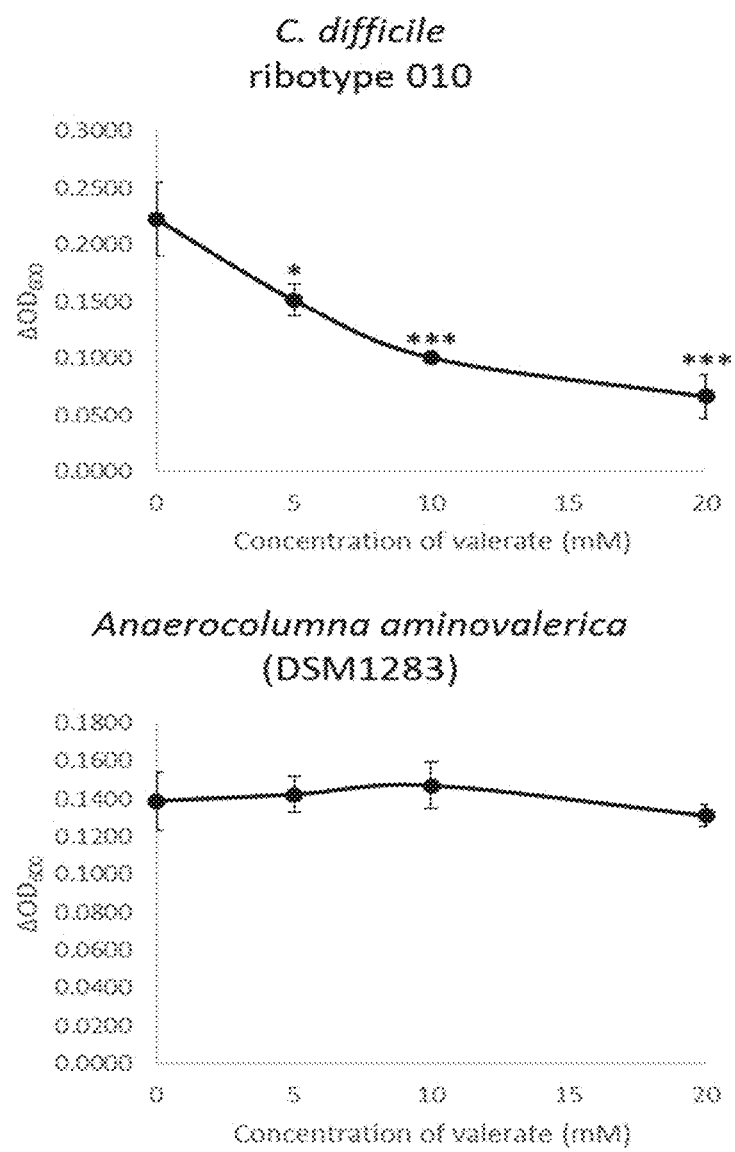
FIG. 33 shows plots of the change in OD600 against different concentrations of valerate (0, 5, 10, and 20 mM) and gut commensal bacteria. Error bars represent mean±SD. *$p<0.05$; $p<0.01$; *$p<0.001$ (ANOVA and Tukey post hoc test), N=12.
Figure 33:
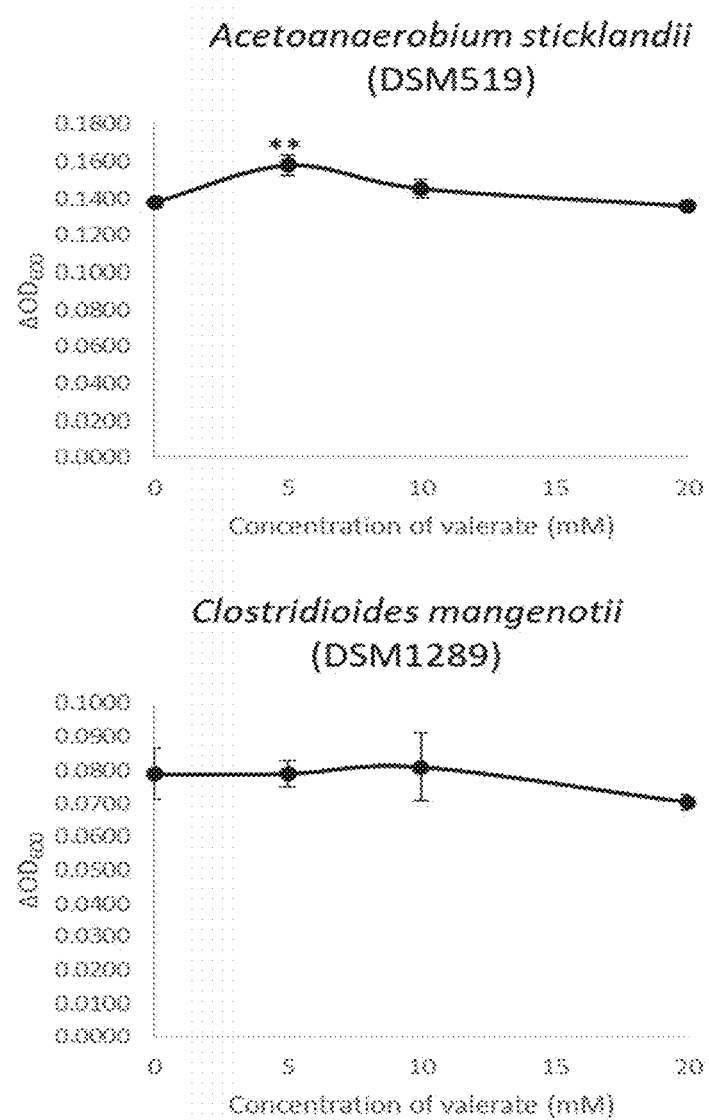
Figure 33:
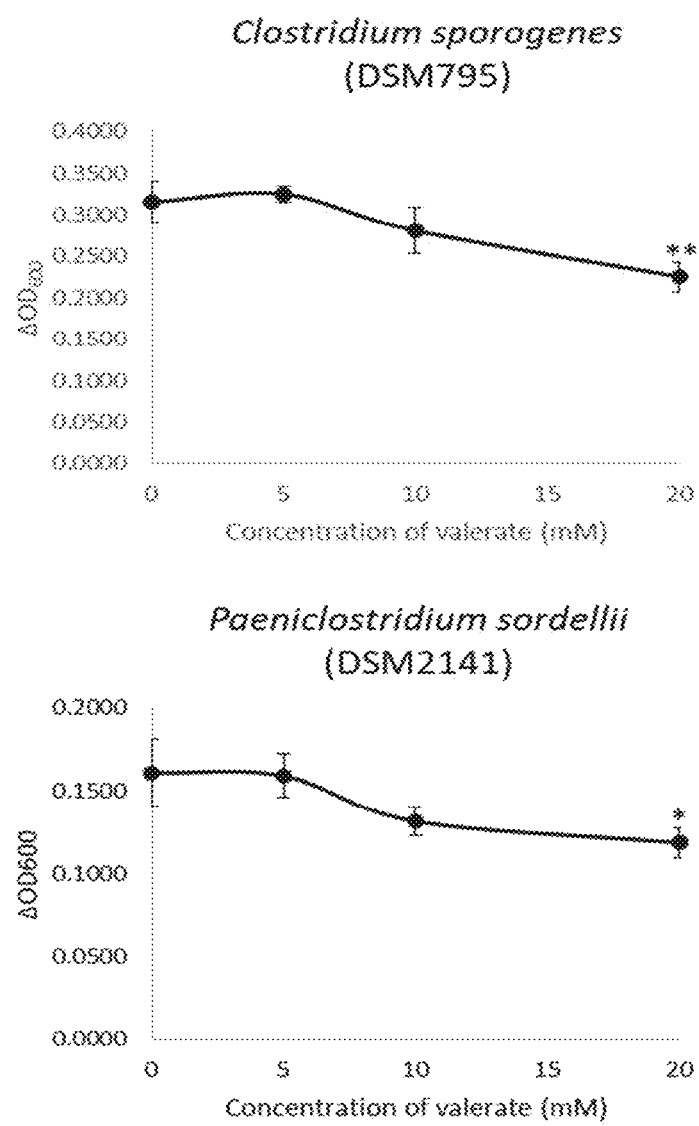
Figure 34:
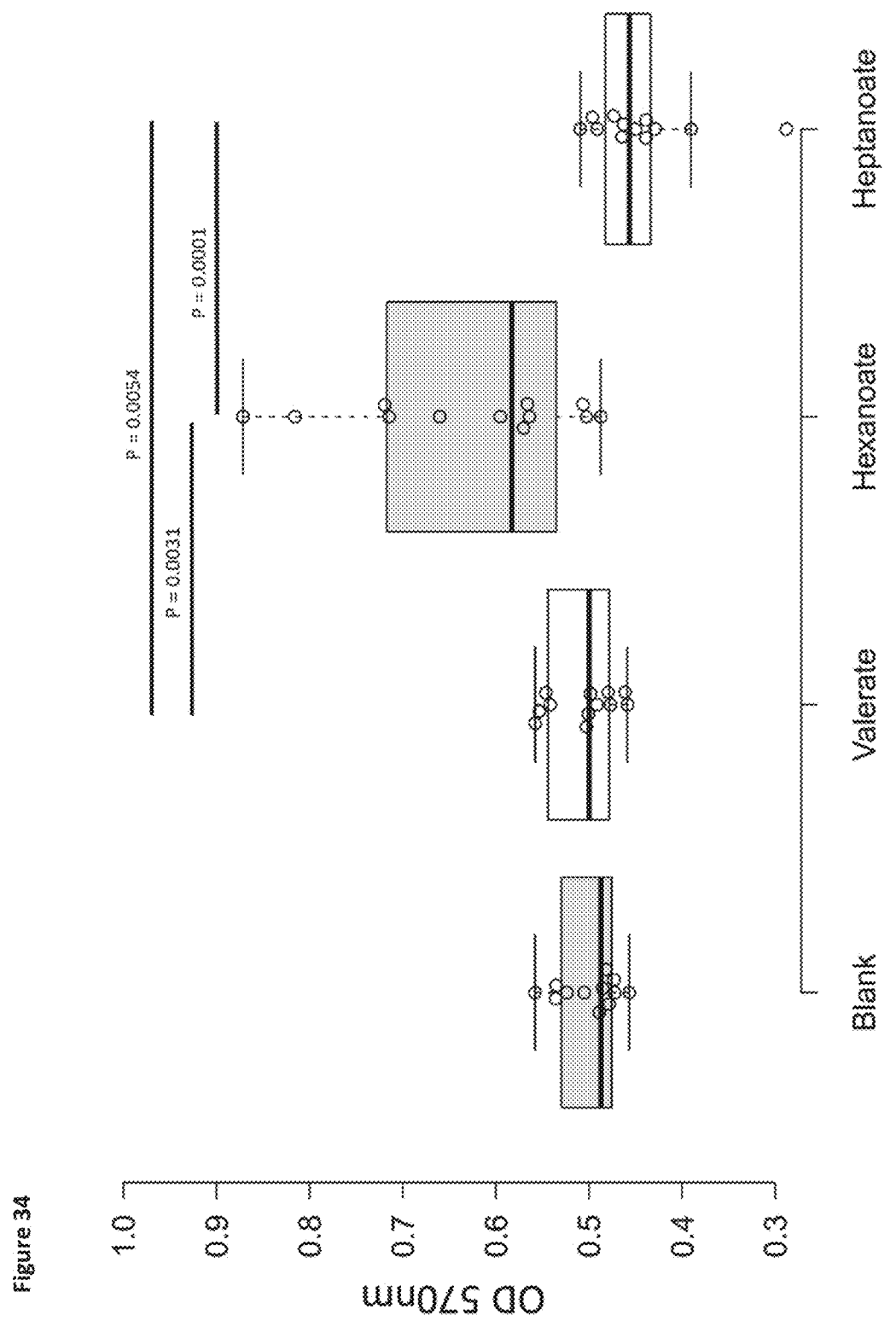
FIG. 34 shows MTT assay of Caco2 cell after a 48-hour incubation with either valerate, hexanoate or heptanoate. A higher OD value represents greater viability.
Figure 35:
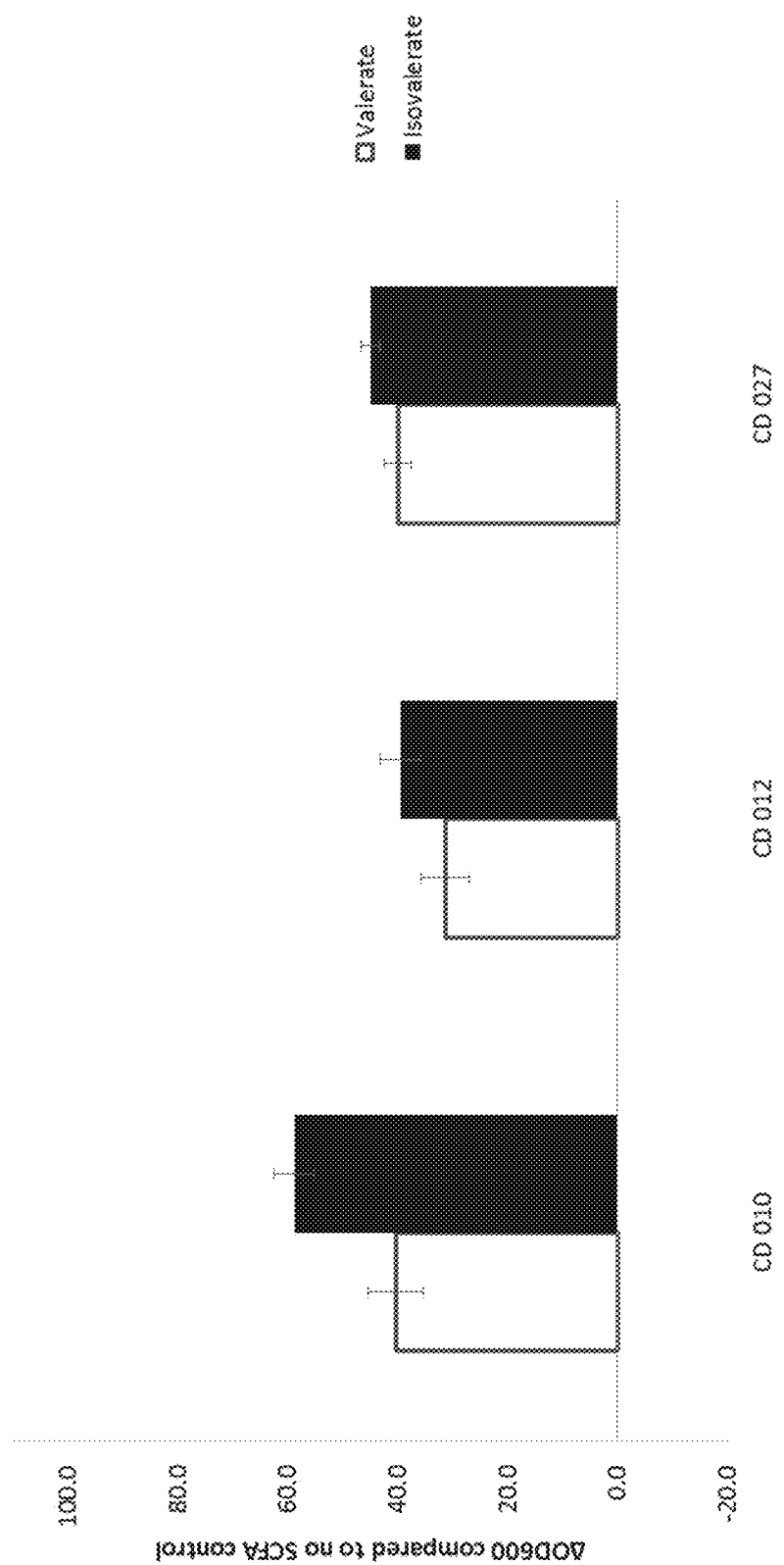
FIG. 35 shows the ability of isovalerate to inhibit the growth of *C. difficile*.

Assessment of Valerate Inhibition of *C. difficile* Strains and Other Bacterial Species Growth As there are many strains of the *C. difficile* pathogen, the inventors extended the range of strains to determine how valerate inhibited growth (FIG. 32), and have also assessed the ability of valerate to target other species of bacteria (FIG. 33). The results show that valerate was effective against all strains of *C. difficile* tested and that valerate has a minimal effect on other species of gut bacteria.

Effect of C5, C6 and C7 Chain Length Fatty Acids on Viability of the Colonocyte Cell Line Caco2

The inventors determined to what extent the C5, C6 and C7 chain length fatty acids affect viability of the colonocyte cell line Caco2. Caco2 cells were grown until confluent in DMEM with serum and then trypsinised and diluted to $10^5$ cells per ml and re-seeded into a 24 well plate and allowed to grow for a further 48 hours. At this point they were exposed to a 45 mM concentration of the SCFA or MCFA for 48 h and viability assessed using an MT assay. The results show that C5, C6 and C7 chain length fatty acids do not significantly decrease the viability of colonocytes. Further, the C6 fatty acid hexanoate significantly increased cell viability.

Effect of Valerate Isomer on *C. difficile* Growth

The inventors tested the ability of isovalerate to inhibit *C. difficile* growth (FIG. 36). While *C. difficile* growth was inhibited to a greater extent by valerate for two of the strains tested (CD010 and CD012), isovalerate still has a significant ability to inhibit growth in these strains. In addition, the isomer was comparable to valerate for inhibiting *C. difficile* growth in the other strain tested (CD 027). The results show that isomers of short and medium chain fatty acids are effective at inhibiting *C. difficile* growth.

DISCUSSION

The inventors used several 'omic' techniques to study the effects of FMT on CDI in a chemostat model under tightly controlled conditions. The aim of the inventors' study was to directly link changes in *C. difficile* counts to changes in the structure and function of the cultured faecal microbiota. They confirmed their findings by analysing human stool samples and by performing *C. difficile* batch culture experiments. The inventors tested valerate, hexanoate and heptanoate, and found that they are all potent inhibitors of *C. difficile*.

In this study, the inventors found that the SCFA valerate was significantly depleted in chemostat culture during clindamycin dosing and did not recover after clindamycin dosing was stopped. Valerate significantly increased with FMT treatment and had a strong negative correlation with *C. difficile* TVC. These findings were corroborated with human data which showed valerate was depleted in recurrent CDI patient stool but was restored following successful FMT. Batch culture experiments confirmed that valerate directly inhibited the vegetative growth of several *C. difficile* ribotypes, but had minimal effects on the growth of other commensal gut bacteria tested. The inventors, not wishing to be held to any particular theory, hypothesise that maintaining the levels of valerate in the gut microbiota of CDI patients will inhibit the vegetative growth of *C. difficile*. This could be accomplished by directly supplying the gut with valerate or by administering bacteria capable of transforming valerate precursors into to valerate.

Advantageously, valerate is not expected to be harmful to host gut cells, as exposure of gut organoids to 5 mM valerate did not result in cell death or cause significant alterations in gene expression (Drs. Lee Parry and Richard Brown of the European Cancer Stem Cell Research Institute, personal communication, 19 Dec. 2017).

There are several different metabolic pathways that lead to valerate production. 5-aminovalerate is a product of the anaerobic degradation of protein hydrolysates by members of the gut microbiota, in particular *Clostridium* species.[31] In this pathway, proline is reduced to 5-aminovalerate by proline reductase in a Stickland-type fermentation.[32-34] 5-aminovalerate is fermented to valerate in a series of reactions mediated by gut bacteria.[31,35] In another metabolic pathway, some *Clostridium* species can ferment ethanol and propionate to valerate.[37] The inventors found ethanol and propionate increased after clindamycin dosing and decreased following FMT treatment. While not wishing to be held to any particular theory, together, the changes in the levels of valerate and valerate precursors (5-aminovalerate, ethanol, and propionate) over the course of the inventor's chemostat experiments suggests disruption of the valerate pathway due to antibiotics created an environment that permitted *C. difficile* vegetative growth.

*C. difficile* spores can persist following the cessation of antibiotics and germinate to vegetative cells which initiate disease relapse. In their study, the inventors found that TCA, a known potent germinant for *C. difficile* spores,[5] was increased during clindamycin dosing, remained elevated for several days after stopping clindamycin, and had a strong positive correlation with *C. difficile* TVC. However, after stopping clindamycin and allowing chemostat communities to recover and stabilise, they found that bile acid levels recovered to pre-clindamycin levels and did not change with FMT treatment. While not wishing to be bound to any theory, the inventors hypothesise that the transient increase in TCA found during and shortly after stopping clindamycin dosing stimulated *C. difficile* spore germination, resulting in vegetative growth. Once clindamycin dosing stopped and the levels of TCA decreased to pre-clindamycin levels, *C. difficile* spores had already germinated and were growing in their vegetative state which is no longer affected by the presence of TCA (as shown by Sorg and Sonnenshein[5], and confirmed in the inventor's study using batch cultures). To prevent CDI initiation and relapse following the cessation of antibiotics, it is important to maintain low levels of TCA in the gut. One way to accomplish this would be to ensure the maintenance of bile salt hydrolase (BSH) enzymes during and after antibiotic exposure. These enzymes are produced by commensal gut bacteria and are responsible for deconjugating tauro- and glyco-conjugated bile acids. It has been proposed that antibiotics kill BSH-producing bacteria, resulting in the accumulation of TCA in the gut. Therefore, re-inoculation of BSH-producing bacteria with FMT may be responsible for degrading TCA present following the cessation of antibiotics, and prevent the germination of *C. difficile* spores. A safer way of restoring BSH activity in the gut microbiomes of CDI patients would be to administer purified BSH enzyme preparations to avoid the administration of live microorganisms.

The inventor's chemostat experiments more closely modelled the first episode of CDI and not recurrent CDI. In first episodes of CDI, human patients are exposed to *C. difficile* spores while taking an inciting antibiotic (e.g. clindamycin). In the inventor's study clindamycin exposure was sufficient to deplete valerate and elevate levels of TCA, allowing *C. difficile* spore germination and vegetative growth. The inventors waited 10 days after stopping clindamycin dosing before administering the FMT preparation to allow the perturbed microbial communities to stabilise following the cessation of antibiotics. This delay allowed the inventors to more easily determine which metabolites were altered only by FMT, and which metabolites were able to recover after antibiotic treatment (in the absence of FMT). This feature is a major advantage of performing chemostat studies, as it would be unethical to withhold treatment from recurrent CDI patients in human studies to determine which metabolites would recover in the absence of FMT. The inventors found no significant difference in *C. difficile* TVC at the end of the clindamycin-dosing period compared to TVC immediately prior to administering FMT or saline treatment. This means the metabolites that recovered following the cessation of clindamycin dosing, but before FMT, did not affect the vegetative growth of *C. difficile* (i.e. bile acids). However, the inventors did see a significant decrease in *C. difficile* TVC and spore counts after FMT. While not wishing to be bound to any theory, this decrease suggests that bacterial metabolites that decreased *C. difficile* counts did not recover after stopping clindamycin, but only recovered with FMT (i.e. valerate).

The first line of therapy for an initial episode of CDI is vancomycin/metronidazole therapy. These antibiotics kill *C. difficile* vegetative cells, but *C. difficile* spores can persist.[38] If vancomycin/metronidazole therapy is stopped while these *C. difficile* spores are present, the elevated levels of TCA (present following the cessation of antibiotics) will cause *C. difficile* spore germination, and low levels of valerate will allow *C. difficile* vegetative growth and therefore recurrent disease.

Most human studies of CDI have focused on recurrent CDI, not first episode of CDI. In this study the inventors showed that valerate was depleted in recurrent CDI patients' pre-FMT, but was restored post-FMT. To the inventor's knowledge this is the first study to measure valerate in the stool of recurrent CDI patients pre- and post-FMT. A previous study by Weingarden and colleagues found that TCA was elevated in the stool of recurrent CDI patients pre-FMT, but was decreased post-FMT.[7] It is important to note that in these human studies recurrent CDI patients were taking vancomycin when pre-FMT samples were collected, and FMT was administered to recurrent CDI patients within 1-2 days of stopping vancomycin therapy. While the inventors could have designed their chemostat experiments to also include a vancomycin dosing regimen, followed by FMT administration 1-2 days later, broad-spectrum vancomycin therapy would have killed more gut bacteria and depleted the chemostat cultures of additional ecosystem functions that were not important for the establishment of the infection, leading to false positives once these functionalities were restored following FMT. In the inventor's chemostat experiments FMT was administered 10 days after stopping clindamycin and pre-FMT samples were collected immediately prior to FMT administration. Had the inventors chosen to administer the FMT preparation within 1-2 days after stopping clindamycin they would expect TCA levels to decrease with FMT.

The inventors found that succinate transiently increased in chemostat cultures with clindamycin dosing, but negatively correlated with *C. difficile* TVC. While not wishing to be bound to any theory, the inventors believe the negative correlation between *C. difficile* TVC and succinate is because *C. difficile* uses succinate for growth. Members of *Bacteroidetes* and the Negativicutes class of *Firmicutes* can degrade succinate to propionate, and as such succinate does not usually accumulate to high levels in the guts of healthy humans.[39] Another strategy to give *C. difficile* vegetative cells a competitive disadvantage would be to maintain succinate metabolism during antibiotic exposure by administering succinate-degrading enzymes, so succinate is no longer available for *C. difficile* growth.

While not wishing to be bound to any theory, the findings from the inventor's study support the hypothesis that antibiotic exposure causes a depletion of specific metabolic pathways normally found in healthy gut microbiotas, resulting in an environment that favours *C. difficile* germination and growth. It also supports the inventor's hypothesis that FMT administration reverses these effects by restoring the bacteria responsible for performing these key metabolic functions. These findings have the potential to directly impact clinical practice in the foreseeable future by developing targeted treatments for CDI by different routes, alone or in combinations: (1) directly supplement the gut with valerate (to inhibit *C. difficile* vegetative growth); (2) directly supplement the gut with bile salt hydrolase (BSH)

enzymes (to degrade taurocholic acid and prevent *C. difficile* spore germination); and (3) directly supplement the gut with succinate-metabolising enzymes (to metabolise succinate and give *C. difficile* vegetative cells a competitive disadvantage). These proposed interventions are well-defined and represent safer options that will avoid all the risks involved with administering live microorganisms to patients and will not promote antimicrobial resistance. These therapies could also be delivered using more patient-friendly methods that do not require the need to preserve live microorganisms. These promising new therapies should be further evaluated in prospective studies in vivo.

The bacterial enzyme 7-α-dehydroxylase is responsible for converting unconjugated primary bile acids CA and CDCA to the secondary bile acids DCA and LCA, respectively. DCA and LCA have been shown to inhibit *C. difficile* vegetative growth at specific concentrations,[30,31] and a previous study has shown that DCA and LCA were depleted in pre-FMT samples from recurrent CDI patients, but were restored in post-FMT samples.[32] These findings led researchers to propose antibiotic exposure results in the loss of bacteria with 7-α-dehydroxylase activity, reducing DCA and LCA production and permitting *C. difficile* vegetative growth. A study by Buffie and colleagues found that administration of *Clostridium scindens* (a bacterium with 7-α-dehydroxylase activity) was associated with resistance to *C. difficile* by restoring the production of the secondary bile acids DCA and LCA.[33] However, in the inventor's study they found that the levels of DCA and LCA recovered in chemostat cultures following the cessation of clindamycin. While they did find strong negative correlations between *C. difficile* TVC and the secondary bile acids DCA and LCA, recovery of these bile acids to pre-clindamycin levels was not enough to decrease vegetative *C. difficile* counts in chemostat cultures.

REFERENCES

1. Mitu-Pretorian O M, Forgacs B, Qumruddin A, et al. Outcomes of patients who develop symptomatic *Clostridium difficile* infection after solid organ transplantation. Transplant Proc 2010; 42:2631-2633.
2. Ma G K, Brensinger C M, Wu Q, et al. Increasing incidence of multiply recurrent *Clostridium difficile* infection in the United States: a cohort study. Ann Intern Med 2017; 167:152-158.
3. van Nood E, Vrieze A, Nieuwdorp M, et al. Duodenal infusion of donor feces for recurrent *Clostridium difficile*. N Engl J Med 2013; 368:407-415.
4. Petrof E O, Gloor G B, Vanner S J, et al. Stool substitute transplant therapy for the eradication of *Clostridium difficile* infection: 'RePOOPulating' the gut. Microbiome 2013; 1:3-2618-1-3.
5. Sorg J A, Sonenshein A L. Bile salts and glycine as cogerminants for *Clostridium difficile* spores. J Bacteriol 2008; 190:2505-2512.
6. Theriot C M, Koenigsknecht M J, Carlson P E, Jr, et al. Antibiotic-induced shifts in the mouse gut microbiome and metabolome increase susceptibility to *Clostridium difficile* infection. Nat Commun 2014; 5:3114.
7. Weingarden A R, Chen C, Bobr A, et al. Microbiota transplantation restores normal fecal bile acid composition in recurrent *Clostridium difficile* infection. Am J Physiol Gastrointest Liver Physiol 2014; 306:G310-9.
8. Ferreyra J A, Wu K J, Hryckowian A J, et al. Gut microbiota-produced succinate promotes *C. difficile* infection after antibiotic treatment or motility disturbance. Cell Host Microbe 2014; 16:770-777.
9. Ott S J, Waetzig G H, Rehman A, et al. Efficacy of sterile fecal filtrate transfer for treating patients with *Clostridium difficile* infection. Gastroenterology 2017; 152:799-811.e7.
10. De Filippo C, Cavalieri D, Di Paola M, et al. Impact of diet in shaping gut microbiota revealed by a comparative study in children from Europe and rural Africa. Proc Natl Acad Sci USA 2010; 107:14691-14696.
11. Morrison D J, Preston T. Formation of short chain fatty acids by the gut microbiota and their impact on human metabolism. Gut Microbes 2016; 7:189-200.
12. McDonald J A K. In vitro models of the human microbiota and microbiome. Emerg Top Life Sci 2017; 1:373-384.
13. Macfarlane G T, Macfarlane S. Models for intestinal fermentation: association between food components, delivery systems, bioavailability and functional interactions in the gut. Curr Opin Biotechnol 2007; 18:156-162.
14. McDonald J A, Schroeter K, Fuentes S, et al. Evaluation of microbial community reproducibility, stability and composition in a human distal gut chemostat model. J Microbiol Methods 2013; 95:167-174.
15. Van den Abbeele P, Grootaert C, Marzorati M, et al. Microbial community development in a dynamic gut model is reproducible, colon region specific, and selective for *Bacteroidetes* and *Clostridium* cluster IX. Appl Environ Microbiol 2010; 76:5237-5246.
16. Freeman J, Baines S D, Jabes D, et al. Comparison of the efficacy of ramoplanin and vancomycin in both in vitro and in vivo models of clindamycin-induced *Clostridium difficile* infection. J Antimicrob Chemother 2005; 56:717-725.
17. Baines S D, O'Connor R, Saxton K, et al. Comparison of oritavancin versus vancomycin as treatments for clindamycin-induced *Clostridium difficile* PCR ribotype 027 infection in a human gut model. J Antimicrob Chemother 2008; 62:1078-1085.
18. Chilton C H, Crowther G S, Freeman J, et al. Successful treatment of simulated *Clostridium difficile* infection in a human gut model by fidaxomicin first line and after vancomycin or metronidazole failure. J Antimicrob Chemother 2014; 69:451-462.
19. Chilton C H, Crowther G S, Baines S D, et al. In vitro activity of cadazolid against clinically relevant *Clostridium difficile* isolates and in an in vitro gut model of *C. difficile* infection. J Antimicrob Chemother 2014; 69:697-705.
20. Meader E, Mayer M J, Steverding D, et al. Evaluation of bacteriophage therapy to control *Clostridium difficile* and toxin production in an in vitro human colon model system. Anaerobe 2013; 22:25-30.
21. Chilton C H, Crowther G S, Spiewak K, et al. Potential of lactoferrin to prevent antibiotic-induced *Clostridium difficile* infection. J Antimicrob Chemother 2016; 71:975-985.
22. Freeman J, Baines S D, Saxton K, et al. Effect of metronidazole on growth and toxin production by epidemic *Clostridium difficile* PCR ribotypes 001 and 027 in a human gut model. J Antimicrob Chemother 2007; 60:83-91.
23. Mullish B H, Marchesi J R, Thursz M R, et al. Microbiome manipulation with faecal microbiome transplantation as a therapeutic strategy in *Clostridium difficile* infection. QJM 2015; 108:355-359.

24. Illumina I. 16S Metagenomic Sequencing Library Preparation (Part #15044223 Rev. B); 2013. Available at: https://support.illumina.com/content/dam/illumina-support/documents/documentation/chemistrydocumentation/16s/16s-metagenomic-library-prep-guide-15044223-b.pdf, 2017.
25. Weljie A M, Newton J, Mercier P, et al. Targeted profiling: quantitative analysis of 1H NMR metabolomics data. Anal Chem 2006; 78:4430-4442.
26. Sarafian M H, Lewis M R, Pechlivanis A, et al. Bile acid profiling and quantification in biofluids using ultra-performance liquid chromatography tandem mass spectrometry. Anal Chem 2015; 87:9662-9670.
27. Kao D, Roach B, Silva M, et al. Effect of oral capsule-vs colonoscopy-delivered fecal microbiota transplantation on recurrent Clostridium difficile infection: a randomized clinical trial. JAMA 2017; 318:1985-1993.
28. Garcia-Villalba R, Gimenez-Bastida J A, Garcia-Conesa M T, et al. Alternative method for gas chromatography-mass spectrometry analysis of short-chain fatty acids in faecal samples. J Sep Sci 2012; 35:1906-1913.
29. Wolfer A. SANTA-App: Interactive package for Short AsyNchronous Time-series Analysis (SANTA) in R, implemented in Shiny; 2017. Available at: https://github.com/adwolfer/SANTA-App, 2017.
30. Le Cao K, Rohart F, Gonzalez I, et al. mixOmics: Omics Data Integration Project. R package version 6.1.2.; 2017. Available at: https://CRAN.R-project.org/package=mixOmics, 2017.
31. Barker H A, D'Ari L, Kahn J. Enzymatic reactions in the degradation of 5-aminovalerate by Clostridium aminovalericum. J Biol Chem 1987; 262:8994-9003.
32. Seto B, Stadtman T C. Purification and properties of proline reductase from Clostridium sticklandii. J Biol Chem 1976; 251:2435-2439.
33. Hodgins D S, Abeles R H. Studies of the mechanism of action of D-proline reductase: the presence on covalently bound pyruvate and its role in the catalytic process. Arch Biochem Biophys 1969; 130:274-285.
34. Seto B. The Stickland reaction. In: Knowles C J, ed. Diversity of Bacterial Respiratory Systems (Vol. II). Boca Raton, FL: CRC Press, 1980:49-64.
35. Buckel W. Unusual enzymes involved in five pathways of glutamate fermentation. Appl Microbiol Biotechnol 2001; 57:263-273.
36. Savidge T, Dann S. Methods and uses for metabolic profiling for Clostridium difficile infection. 2013; PCT/US2012/064218.
37. Bornstein B T, Barker H A. The energy metabolism of Clostridium kluyveri and the synthesis of fatty acids. J Biol Chem 1948; 172:659-669.
38. Borody T J, Khoruts A. Fecal microbiota transplantation and emerging applications. Nat Rev Gastroenterol Hepatol 2011; 9:88-96.
39. Louis P, Flint H J. Formation of propionate and butyrate by the human colonic microbiota. Environ Microbiol 2017; 19:29-41.

The invention claimed is:

1. A method of treating, preventing or ameliorating a *Clostridioides difficile* infection by selectively inhibiting the growth of *Clostridioides difficile*, the method comprising administering, to a subject in need thereof, a therapeutically effective amount of a compound of Formula (I):

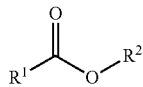

Formula (I)

wherein $R^1$ is a $C_4$ to $C_6$ alkyl or fluorinated alkyl; and $R^2$ is hydrogen or a $C_1$ to $C_4$ alkyl or halogenated alkyl, and the $C_1$ to $C_4$ alkyl or halogenated alkyl is optionally substituted with between 1 and 5 substituents, wherein each substituent has the formula:

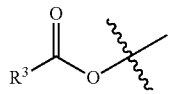

wherein each $R^3$ is independently a $C_2$ to $C_{10}$ alkyl or halogenated alkyl;

or a pharmaceutically acceptable salt of the compound of Formula I, solvate of the compound of Formula I, tautomeric form of the compound of Formula I or polymorphic form of the compound of Formula I.

2. The method according to claim 1, wherein the compound is of the Formula (Ia):

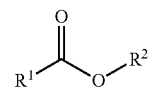

Formula (Ia)

wherein $R^1$ is a $C_4$ to $C_6$ alkyl or fluorinated alkyl; and $R^2$ is hydrogen or a $C_1$ to $C_4$ alkyl or halogenated alkyl;

or a pharmaceutically acceptable salt of the compound Formula (Ia), solvate of the compound Formula (Ia), tautomeric form of the compound Formula (Ia) or polymorphic form of the compound Formula (Ia).

3. The method according to claim 1, wherein $R^2$ is hydrogen.

4. The method according to claim 1, wherein $R^1$ is a $C_4$ alkyl or fluorinated alkyl.

5. The method according to claim 1, wherein $R^1$ is butyl.

6. The method according to claim 1, wherein $R^1$ is pentyl or a fluorinated pentyl.

7. The method according to claim 1, wherein $R^1$ is hexyl or a fluorinated hexyl.

* * * * *

SEQUENCE LISTING

```
<160> NUMBER OF SEQ ID NOS: 18

<210> SEQ ID NO 1
<211> LENGTH: 316
<212> TYPE: PRT
<213> ORGANISM: Bifidobacterium adolescentis

<400> SEQUENCE: 1

Met Cys Thr Gly Val Arg Phe Ser Asp Glu Glu Gly Asn Met Tyr Phe
1               5                   10                  15

Gly Arg Asn Leu Asp Trp Ser Phe Ser Tyr Gly Glu Ser Ile Leu Ala
            20                  25                  30

Thr Pro Arg Gly Tyr His Tyr Asp Asn Val Phe Gly Ala Ser Gly Lys
        35                  40                  45

Ala Thr Pro Asn Ala Val Ile Gly Val Gly Val Val Met Ala Asp Arg
    50                  55                  60

Pro Met Tyr Phe Asp Cys Ala Asn Glu His Gly Leu Ala Ile Ala Gly
65                  70                  75                  80

Leu Asn Phe Pro Gly Tyr Ala Glu Phe Val His Glu Pro Val Glu Gly
                85                  90                  95

Thr Asp Asn Val Ala Thr Phe Glu Phe Pro Leu Trp Val Ala Arg Asn
            100                 105                 110

Phe Asp Ser Val Asp Glu Val Glu Lys Ala Leu Lys Asn Val Thr Ile
        115                 120                 125

Val Ser Gln Ile Val Pro Gly Gln Gln Glu Ser Leu Leu His Trp Ile
    130                 135                 140

Ile Gly Asp Ser Glu Arg Ser Ile Val Val Glu Gln Met Ala Asp Gly
145                 150                 155                 160

Met His Val His His Asp Asp Val Asp Val Leu Thr Asn Gln Pro Thr
                165                 170                 175
```

Phe Gly Phe His Met Glu Asn Leu Arg Asn Tyr Met Cys Val Gly Asn
            180                 185                 190

Glu Met Ala Glu Pro Ala Thr Trp Gly Lys Ala Ser Leu Ser Ala Trp
        195                 200                 205

Gly Ala Gly Val Ser Met His Gly Ile Pro Gly Asp Val Ser Ser Pro
    210                 215                 220

Ser Arg Phe Val Arg Val Ala Tyr Ala Asn Thr His Tyr Pro Gln Gln
225                 230                 235                 240

Glu Gly Glu Ala Ala Asn Val Ser Arg Leu Phe His Thr Leu Gly Ser
                245                 250                 255

Val Gln Met Val Asp Gly Met Ala Lys Met Gly Asn Gly Gln Phe Glu
            260                 265                 270

Arg Thr Leu Phe Thr Ser Gly Tyr Ser Ser Lys Thr Asn Thr Tyr Tyr
        275                 280                 285

Met Asn Thr Tyr Asp Asp Pro Ala Ile Arg Ser Tyr Ala Met Ala Asp
    290                 295                 300

Phe Asp Met Asp Ser Ser Glu Leu Ile Thr Ala Ala
305                 310                 315

<210> SEQ ID NO 2
<211> LENGTH: 948
<212> TYPE: DNA
<213> ORGANISM: Bifidobacterium adolescentis

<400> SEQUENCE: 2
atgtgtaccg tgttcgttt tagtgatgaa gagggcaata tgtattttgg tcgtaatctg        60
gattggagct ttagctatgg tgaaagcatt ctggcaacac cgcgtggtta tcactatgat       120
aatgtttttg gtgcaagcgg taaagcaacc ccgaatgcag ttattggtgt tggtgttgtt       180
atggcagatc gtccgatgta tttcgattgt gcaaatgaac atggtctggc aattgcaggt       240
ctgaattttc cgggttatgc agaatttgtg catgaaccgg ttgaaggcac cgataatgtt       300
gcaacctttg aatttccgct gtgggttgca cgtaattttg atagcgttga tgaagttgag       360
aaagccctga aaatgttac cattgtgagc cagattgttc cgggtcagca agaaagcctg       420
ctgcattgga ttattggtga tagcgaacgt agcattgttg ttgagcagat ggcagatggt       480
atgcatgttc atcacgatga tgttgatgtt ctgaccaatc agccgacctt tggttttcat       540
atggaaaatc tgcgcaacta tatgtgcgtg gtaatgaaa tggcagaacc ggcaacctgg       600
ggtaaagcca gcctgagcgc atggggtgcc ggtgttagca tgcatggtat tccgggtgat       660
gttagcagcc cgagccgttt tgttcgtgtt gcctatgcaa atacccatta tccgcagcaa       720
gagggtgaag cagcaaatgt tagccgtctg tttcataccc tgggtagcgt tcagatggtt       780
gatggcatgg caaaaatggg taatggtcag tttgaacgta ccctgtttac cagcggttat       840
agcagcaaaa ccaacaccta ttatatgaac acctatgacg atccggcaat tcgtagctat       900
gcaatggcag attttgatat ggatagcagc gaactgatta ccgcagca                    948

<210> SEQ ID NO 3
<211> LENGTH: 16
<212> TYPE: DNA
<213> ORGANISM: Artificial Sequence
<220> FEATURE:
<223> OTHER INFORMATION: BactQUANT forward primer

<400> SEQUENCE: 3
cctacgggag gcagca                                                        16

<210> SEQ ID NO 4
<211> LENGTH: 20
<212> TYPE: DNA
<213> ORGANISM: Artificial Sequence
<220> FEATURE:
<223> OTHER INFORMATION: BactQUANT reverse primer

<400> SEQUENCE: 4
ggactaccgg gtatctaatc                                              20

<210> SEQ ID NO 5
<211> LENGTH: 14
<212> TYPE: DNA
<213> ORGANISM: Artificial Sequence
<220> FEATURE:
<223> OTHER INFORMATION: probe (6FAM)

<400> SEQUENCE: 5
cagcagccgc ggta                                                    14

<210> SEQ ID NO 6
<211> LENGTH: 52
<212> TYPE: DNA
<213> ORGANISM: Artificial Sequence
<220> FEATURE:
<223> OTHER INFORMATION: 28F-YM (forward primer)

<400> SEQUENCE: 6
tcgtcggcag cgtcagatgt gtataagaga caggagtttg atymtggctc ag          52

<210> SEQ ID NO 7
<211> LENGTH: 52
<212> TYPE: DNA
<213> ORGANISM: Artificial Sequence
<220> FEATURE:
<223> OTHER INFORMATION: 28F-Borrellia (forward primer)

<400> SEQUENCE: 7
tcgtcggcag cgtcagatgt gtataagaga caggagtttg atcctggctt ag          52

<210> SEQ ID NO 8
<211> LENGTH: 52
<212> TYPE: DNA
<213> ORGANISM: Artificial Sequence
<220> FEATURE:
<223> OTHER INFORMATION: 28FChloroflex (forward primer)

<400> SEQUENCE: 8
tcgtcggcag cgtcagatgt gtataagaga caggaatttg atcttggttc ag          52

<210> SEQ ID NO 9
<211> LENGTH: 52
<212> TYPE: DNA
<213> ORGANISM: Artificial Sequence
<220> FEATURE:
<223> OTHER INFORMATION: 28F-Bifdo (forward primer)

<400> SEQUENCE: 9
tcgtcggcag cgtcagatgt gtataagaga caggggttcg attctggctc ag          52

<210> SEQ ID NO 10
<211> LENGTH: 53
<212> TYPE: DNA
<213> ORGANISM: Artificial Sequence
<220> FEATURE:

<223> OTHER INFORMATION: 388R (reverse primer)

<400> SEQUENCE: 10
gtctcgtggg ctcggagatg tgtataagag acagtgctgc ctcccgtagg agt    53

<210> SEQ ID NO 11
<211> LENGTH: 31
<212> TYPE: DNA
<213> ORGANISM: Artificial Sequence
<220> FEATURE:
<223> OTHER INFORMATION: 1a forward

<400> SEQUENCE: 11
cacatattgt ggcacgaaca athgartggg g    31

<210> SEQ ID NO 12
<211> LENGTH: 31
<212> TYPE: DNA
<213> ORGANISM: Artificial Sequence
<220> FEATURE:
<223> OTHER INFORMATION: 1a Reverse

<400> SEQUENCE: 12
ctgtgcccgg atacagatta acrtarttrt t    31

<210> SEQ ID NO 13
<211> LENGTH: 24
<212> TYPE: DNA
<213> ORGANISM: Artificial Sequence
<220> FEATURE:
<223> OTHER INFORMATION: 1b forward

<400> SEQUENCE: 13
cggcgttccg catttytayg araa    24

<210> SEQ ID NO 14
<211> LENGTH: 31
<212> TYPE: DNA
<213> ORGANISM: Artificial Sequence
<220> FEATURE:
<223> OTHER INFORMATION: 1b Reverse

<400> SEQUENCE: 14
gttcaatgcc aatcggaata tcraarttrt t    31

<210> SEQ ID NO 15
<211> LENGTH: 27
<212> TYPE: DNA
<213> ORGANISM: Artificial Sequence
<220> FEATURE:
<223> OTHER INFORMATION: 3c/e Forward

<400> SEQUENCE: 15
ttttggccga acactggayt aygartt    27

<210> SEQ ID NO 16
<211> LENGTH: 29
<212> TYPE: DNA
<213> ORGANISM: Artificial Sequence
<220> FEATURE:
<223> OTHER INFORMATION: 3c/e Reverse

<400> SEQUENCE: 16
tcaacggagc ccagaatatg raaraaytg    29

```
<210> SEQ ID NO 17
<211> LENGTH: 25
<212> TYPE: DNA
<213> ORGANISM: Artificial Sequence
<220> FEATURE:
<223> OTHER INFORMATION: baiCD Forward

<400> SEQUENCE: 17
ggwttcagcc crcagatgtt ctttg                                     25

<210> SEQ ID NO 18
<211> LENGTH: 30
<212> TYPE: DNA
<213> ORGANISM: Artificial Sequence
<220> FEATURE:
<223> OTHER INFORMATION: baiCD Reverse

<400> SEQUENCE: 18
gaattccggg ttcatgaaca ttctkckaag                                30
```